(12) United States Patent
Contreras et al.

(10) Patent No.: US 6,803,225 B2
(45) Date of Patent: Oct. 12, 2004

(54) **PROTEIN GLYCOSYLATION MODIFICATION IN *PICHIA PASTORIS***

(75) Inventors: Roland Contreras, Merelbeke (BE); Nico L. M. Callewaert, Lichtervelde (BE); Steven C. J. Geysens, Kruishoutem (BE)

(73) Assignee: Flanders Interuniversity Institute for Biotechnology, Zwijnaarde (BE)

( * ) Notice: Subject to any disclaimer, the term of this patent is extended or adjusted under 35 U.S.C. 154(b) by 0 days.

(21) Appl. No.: 09/896,594

(22) Filed: Jun. 29, 2001

(65) Prior Publication Data

US 2002/0188109 A1 Dec. 12, 2002

Related U.S. Application Data

(60) Provisional application No. 60/215,676, filed on Jun. 30, 2000.

(51) Int. Cl.[7] .............................. C12N 1/14; C12N 1/16; C12N 15/00; C12N 15/74
(52) U.S. Cl. .............................. 435/254.2; 435/254.22; 435/254.23; 435/320.1; 435/483
(58) Field of Search .............................. 435/320.1, 471, 435/69.1, 62.7, 476–478, 483, 375, 254.1–254.11, 255.1–255.2, 255.4, 255.5, 255.6; 536/231, 23.2, 23.74

(56) References Cited

U.S. PATENT DOCUMENTS

| | | | |
|---|---|---|---|
| 5,135,854 A | 8/1992 | MacKay et al. | ............ 435/69.1 |
| 5,705,616 A | 1/1998 | Lehle et al. | ................ 530/395 |
| 2002/0137134 A1 * | 9/2002 | Gerngross | .................. 435/69.1 |

FOREIGN PATENT DOCUMENTS

JP        8-336387        12/1996

OTHER PUBLICATIONS

Inoue et al. Molecular cloning and nucleotide sequence of the 1,2–alpha–D–mannosidase gene, msdS, from *Aspergillus saitoi* and expression of the gene in yeast cells. Biochim. Biophys. Acta 1253:141–145, 1995.*
Herscovics et al. Isolation of a mouse Golgi mannosidase cDNA, a member of a gene family consdrved from yeast to mammals. J. Biol. Chem. 269: 9864–9871, 1994.*
Lal et al. Isolation and expression of murine and rabbit cDNAs encoding an alpha1,2–mannosidase involved in the processing of asparagine–linked oligosaccharides. J. Biol. Chem. 269:9872–9881, 1995.*
Trombetta et al. Endoplasmic recticulum glucosidase II is composed of a catalytic subunit, conserved from yeast to mammals, and a tightly bound noncatalytic HDEL–containing subunit. J. Biol. Chem. 271:27509–27516, 1996.*

Ngo et al. Computational complexity, protein structure prediction, and the Levinthal Paradox. In: The protein folding problem and tertiary structure prediction (Merz et al., Eds.), Birkhauser, Boston, 1994, pp. 491–495.*
Rudinger, J. Characteristics of the amino acids as components of a peptide hormone sequence. In: Peptdie hormones (Parsons, J.A., Ed.), University Park Press, Baltimore, 1976, pp. 1–7.*
Invitrogen catalog, 1998. Yeast expression, p. 22.*
Maras, M., et al. (2000) "Molecular Cloning and Enzymatic Characterization of a *Trichoderma Reesi*, 1,2—αD–Mannosidase", *Journal of Biotechnology* 77: 255–263.
Bretthauer, R. K., et al. (1999) "Glycosylation of *Pichia pastoris*–derviced Proteins", *Biotechnol. Appl Biochem 30*: 193–200.
Kukuruzinska, M. A., et al. (1987) "Protein Glycosylation in Yeast", *Ann. Rev. Biochem 56*: 915–944.
Chiba, Y., et al. (1998) "Production of Human Cpmpatible High Mannse–Type ($Man_5GlcNAc_2$) Sugar Chains in *Saccharomyces cerevisiae*", *The Journal of Biological Chemistry 273 (41)*: 26298–26304.
Maras, M., et al. (1999) In Vivo Synthesis of Complex N–Glycans by Expression of Human N–Acetylglucosaminyltransferase I in the Filamentous Fungus *Trichoderma Reesei*, *FEBS Letters 452*: 365–370.
Nakanishi–Shindo, Y., et al. (1993) "Structure of the N–Linked Oligosaccharides That Show the Complete Loss of α–1, 6–Polymannose Outer Chain from och1, och1 mnn1, and och1 mnn1 alg3 Mutants of *Saccharomyces cerevisiae*", *The Journal of Biological Chemistry 268 (35)*: 26338–26345.
Martinet, W., et al. (1998) "Modification of the Protein Glycosylation Pathway in the Methylotrophic Yeast *Pichia pastoris*", *Biotechnoogy Letters 20 (12)*:1171–1177.
Maras, M., et al. (1997) "In Vitro Conversation of the Carbohydrate Moiety of Fungal Glycoproteins to Mammalian–Type Oligosaccharides", *Eur. J. Biochem.* 249:701–7707.
Laroy,W., et al. (2000) "Cloning of *Trypanosoma cruzi* trans–Sialidase and Expression in *Pichia pastoris*", *Protein Expression and Purification 20*: 389–393.

* cited by examiner

Primary Examiner—David Guzo
Assistant Examiner—Quang Nguyen
(74) Attorney, Agent, or Firm—Scully, Scott, Murphy & Presser

(57) ABSTRACT

The present invention provides genetically engineered strains of Pichia capable of producing proteins with reduced glycosylation. In particular, the genetically engineered strains of the present invention are capable of expressing either or both of an (α-1,2-mannosidase and glucosidase II. The genetically engineered strains of the present invention can be further modified such that the OCH1 gene is disrupted. Methods of producing glycoproteins with reduced glycosylation using such genetically engineered stains of Pichia are also provided.

28 Claims, 23 Drawing Sheets

Glucosidase II assay on commercially available alpha-glucosidase

Glucosidase II assay on heterologously expressed Pichia protein

PROTEIN GLYCOSYLATION MODIFICATION IN *PICHIA PASTORIS*

CROSS REFERENCE TO RELATED APPLICATION

This application claims the benefit of U.S. Provisional Application Ser. No. 60/215,676, filed Jun. 30, 2000.

FIELD OF THE INVENTION

The present invention relates to methods and vectors useful for genetically modifying the glycosylation process in methylotrophic yeast strains for the purpose of producing glycoproteins with reduced glycosylation. The present invention further relates to methylotrophic yeast strains generated using the present methods and vectors, as well as glycoproteins produced from such genetically modified strains.

BACKGROUND OF THE INVENTION

The methylotrophic yeasts including *Pichia pastoris* have been widely used for production of recombinant proteins of commercial or medical importance. However, production and medical applications of some therapeutic glycoproteins can be hampered by the differences in the protein-linked carbohydrate biosynthesis between these yeasts and the target organism such as a mammalian subject.

Protein N-glycosylation originates in the endoplasmic reticulum (ER), where an N-linked oligosaccharide ($Glc_3Man_9GlcNAc_2$) assembled on dolichol (a lipid carrier intermediate) is transferred to the appropriate Asn of a nascent protein. This is an event common to all eukaryotic N-linked glycoproteins. The three glucose residues and one specific α-1,2-linked mannose residue are removed by specific glucosidases and an (α-1,2-mannosidase in the ER, resulting in the core oligosaccharide structure, $Man_8GlcNAc_2$. The protein with this core sugar structure is transported to the Golgi apparatus where the sugar moiety undergoes various modifications. There are significant differences in the modifications of the sugar chain in the Golgi apparatus between yeast and higher eukaryotes.

In mammalian cells, the modification of the sugar chain proceeds via 3 different pathways depending on the protein moiety to which it is added. That is, (1) the core sugar chain does not change; (2) the core sugar chain is changed by adding the N-acetylglucosamine-1-phosphate moiety (GlcNAc-1-P) in UDP-N-acetyl glucosamine (UDP-GlcNAc) to the 6-position of mannose in the core sugar chain, followed by removing the GlcNAc moiety to form an acidic sugar chain in the glycoprotein; or (3) the core sugar chain is first converted into $Man_5GlcNAc_2$ by removing 3 mannose residues with mannosidase I; $Man_5GlcNAc_2$ is further modified by adding GlcNAc and removing 2 more mannose residues, followed by sequentially adding GlcNAc, galactose (Gal), and N-acetylneuraminic acid (also called sialic acid (NeuNAc)) to form various hybrid or complex sugar chains (R. Kornfeld and S. Kornfeld, *Ann. Rev. Biochem.* 54: 631–664, 1985; Chiba et al *J. Biol. Chem.* 273: 26298–26304, 1998).

In yeast, the modification of the sugar chain in the Golgi involves a series of additions of mannose residues by different mannosyltransferases ("outer chain" glycosylation). The structure of the outer chain glycosylation is specific to the organisms, typically with more than 50 mannose residues in *S. cerevisiae*, and most commonly with structures smaller than $Man_{14}GlcNAc_2$ in *Pichia pastoris*. This yeast-specific outer chain glycosylation of the high mannose type is also denoted hyperglycosylation.

Hyperglycosylation is often undesired since it leads to heterogeneity of a recombinant protein product in both carbohydrate composition and molecular weight, which may complicate the protein purification. The specific activity (units/weight) of hyperglycosylated enzymes may be lowered by the increased portion of carbohydrate. In addition, the outer chain glycosylation is strongly immunogenic which is undesirable in a therapeutic application. Moreover, the large outer chain sugar can mask the immunogenic determinants of a therapeutic protein. For example, the influenza neuraminidase (NA) expressed in *P. pastoris* is glycosylated with N-glycans containing up to 30–40 mannose residues. The hyperglycosylated NA has a reduced immunogenicity in mice, as the variable and immunodominant surface loops on top of the NA molecule are masked by the N-glycans (Martinet et al. *Eur J. Biochem.* 247: 332–338, 1997).

Therefore, it is desirable to genetically engineer methylotrophic yeast strains in which glycosylation of proteins can be manipulated and from which recombinant proteins can be produced that would not be compromised in structure or function by large N-glycan side chains.

SUMMARY OF THE INVENTION

The present invention is directed to methods and vectors useful for genetically modifying the glycosylation process in methylotrophic yeast strains to produce glycoproteins with reduced glycosylation. Methylotrophic yeast strains generated using the present methods and vectors, as well as glycoproteins produced from such genetically modified strains are also provided.

In one embodiment, the present invention provides vectors useful for making genetically engineered methylotrophic yeast strains which are capable of producing glycoproteins with reduced glycosylation.

In one aspect, the present invention provides "knock-in" vectors which are capable of expressing in a methylotrophic yeast strain one or more proteins whose enzymatic activities lead to a reduction of glycosylation in glycoproteins produced by the methylotrophic yeast strain.

In a preferred embodiment, the knock-in vectors of the present invention include a nucleotide sequence coding for an α-1,2-mannosidase or a functional part thereof and are capable of expressing the α-1,2-mannosidase or the functional part in a methylotrophic yeast strain. A preferred nucleotide sequence is a nucleotide sequence encoding the α-1,2-mannosidase of a fungal species, and more preferably, *Trichoderma reesei*. Preferably, the α-1,2-mannosidase expression vector is engineered such that the α-1,2-mannosidase or a functional part thereof expressed from the vector includes an ER-retention signal. A preferred ER-retention signal is HDEL (SEQ ID NO: 1). The α-1,2-mannosidase coding sequence can be operable linked to a constitutive or inducible promoter, and a 3' termination sequence. The vectors can be integrative vectors or replicative vectors. Particularly preferred α-1,2-mannosidase expression vectors include pGAPZMFManHDEL, pGAPZMFManMycHDEL, pPICZBMFManMycHDEL, pGAPZmManHDEL, pGAPZmMycManHDEL, pPIC9mMycManHDEL and pGAPZmMycManHDEL.

In another preferred embodiment, the knock-in vectors of the present invention include a sequence coding for a glucosidase II or a functional part thereof and are capable of expressing the glucosidase II or the functional part in a methylotrophic yeast strain. A preferred nucleotide sequence is a nucleotide sequence encoding the glucosidase II of a fungal species, and more preferably, *Saccharomyces cerevisiae*. Preferably, the glucosidase II expression vector is engineered such that the glucosidase II or a functional part thereof expressed from the vector includes an ER-retention signal. A preferred ER-retention signal is HDEL (SEQ ID NO: 1). The glucosidase II coding sequence can be operable linked to a constitutive or inducible promoter, and a 3' termination sequence. The vectors can be integrative vectors or replicative vectors. Particularly preferred glucosidase II expression vectors include pGAPZAGLSII, pPICZAGLSII, pAOX2ZAGLSII, pYPTIZAGLSII, pGAPADEglsII, pPICADEglsII, pAOX2ADEglsII, pYPTIADEglsII, pGAPZAglsIIHDEL and pGAPADEglsIIHDEL.

Expression vectors which include both of an α-1,2-mannosidase expression unit and a glucosidase II expression unit are also provided by the present invention.

In another aspect, the present invention provides "knock-out" vectors which, when introduced into a methylotrophic yeast strain, inactivate or disrupt a gene thereby facilitating the reduction in the glycosylation of glycoproteins produced in the methylotrophic yeast strain.

In one embodiment, the present invention provides a "knock-out" vector which, when introduced into a methylotrophic yeast strain, inactivates or disrupts the Och1 gene. A preferred Och1 knock-out vector is pBLURA5'PpOCH1.

Still another embodiment of the present invention provides vectors which include both a knock-in unit and a knock-out unit.

Furthermore, any of the knock-in or knock-out vectors of the present invention can also include a nucleotide sequence capable of expressing a heterologous protein of interest in a methylotrophic yeast.

Another embodiment of the present invention provides methods of modifying the glycosylation in a methylotrophic yeast by transforming the yeast with one or more vectors of the present invention.

Strains of a methylotrophic yeast which can be modified using the present methods include, but are not limited to, yeast strains capable of growth on methanol such as yeasts of the genera Candida, Hansenula, Torulopsis, and Pichia. Preferred methylotrophic yeasts are of the genus Pichia. Especially preferred are *Pichia pastoris* strains GS115 (NRRL Y-15851), GS190 (NRRL Y-18014), PPF1 (NRRL Y-18017), PPY120H, yGC4, and strains derived therefrom. Methylotrophic yeast strains which can be modified using the present methods also include those methylotrophic yeast strains which have been engineered to express one or more heterologous proteins of interest. The glycosylation on the heterologous proteins expressed from these previously genetically engineered strains can be reduced by transforming such strains with one or more of the vectors of the present invention Methylotrophic yeast strains which are modified by practicing the present methods are provided in another embodiment of the present invention.

A further aspect of the present invention is directed to methods of producing glycoproteins with a reduced glycosylation.

In accordance with such methods, a nucleotide sequence capable of expressing a glycoprotein can be introduced into a methylotrophic yeast strain which has previously been transformed with one or more of the vectors of the present invention. Alternatively, a methylotrophic yeast strain which has been genetically engineered to express a glycoprotein can be transformed with one or more of the vectors of the present invention. Moreover, if a methylotrophic yeast strain is not transformed with a nucleotide sequence encoding a glycoprotein of interest or any of the vectors of the present invention, such yeast strain can be transformed, either consecutively or simultaneously, with both a nucleotide sequence capable of expressing the glycoprotein and one or more vectors of the present invention. Additionally, a methylotrophic yeast strain can be transformed with one or more of the present knock-in and/or knock-out vectors which also include a nucleotide sequence capable of expressing a glycoprotein in the methylotrophic yeast strain.

Glycoproteins products produced by using the methods of the present invention, i.e., glycoproteins with reduced N-glycosylation, are also part of the present invention.

Kits which include one or more of the vectors of the present invention, or one or more strains modified to produce glycoproteins with reduced glycosylation, are also provided.

DETAILED DESCRIPTION OF THE INVENTION

Figure 1:
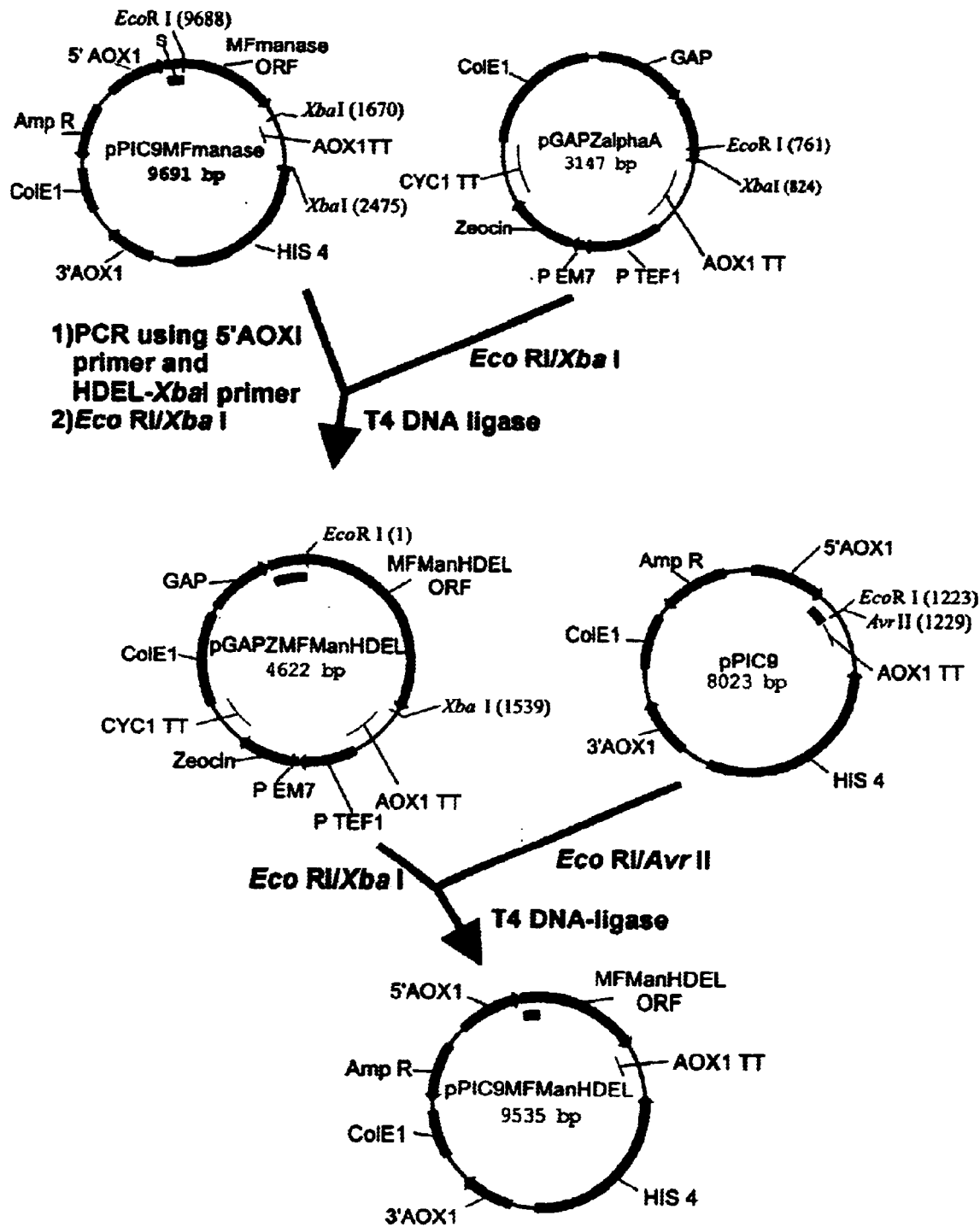
FIG. 1 depicts vectors carrying an HDEL (SEQ ID NO: 1)-tagged *Trichoderma reesei* (α-1,2-mannosidase expression cassette and describes the way in which these vectors were constructed according to methods known in the art. Abbreviations used throughout construction schemes: 5' AOX1 or AOX1 P: *Pichia pastoris* AOX1 promoter sequence; Amp R: ampicillin resistance gene; ColE1: ColE1 origin of replication; 3' AOX1:3' sequences of the *Pichia pastoris* AOX1 gene; HIS4: HIS4 gene of *Pichia pastoris*. AOX TT: transcription terminator sequence of the *Pichia pastoris* AOX1 gene; ORF: open reading frame; S: secretion signal; P TEF1: the promoter sequence of the *Saccharomyces cerevisiae* transcription elongation factor 1 gene; P EM7: synthetic constitutive prokaryotic promotor EM7; Zeocin: Zeocin resistance gene; CYC1 TT: 3' end of the *S. cerevisiae* CYC1 gene; GAP: promoter sequence of the *Pichia pastoris* glyceraldehyde-3-phosphate dehydrogenase gene; PpURA3: *Pichia pastoris* URA3 gene. As can be seen in this figure, the *Trichoderma reesei* α-1,2-mannosidase was operably linked to the coding sequence for the *S. cerevisiae* α-mating factor secretion signal sequence and further operably linked at the 3' terminus of the coding sequence to the coding sequence for an HDEL (SEQ ID NO: 1) peptide. The whole fusion construct was operably linked to either the *P. pastoris* AOX1 promoter (in pPIC9MFManHDEL) or to the *P. pastoris* GAP promotor (in pGAPZMFManHDEL).
Figure 2:
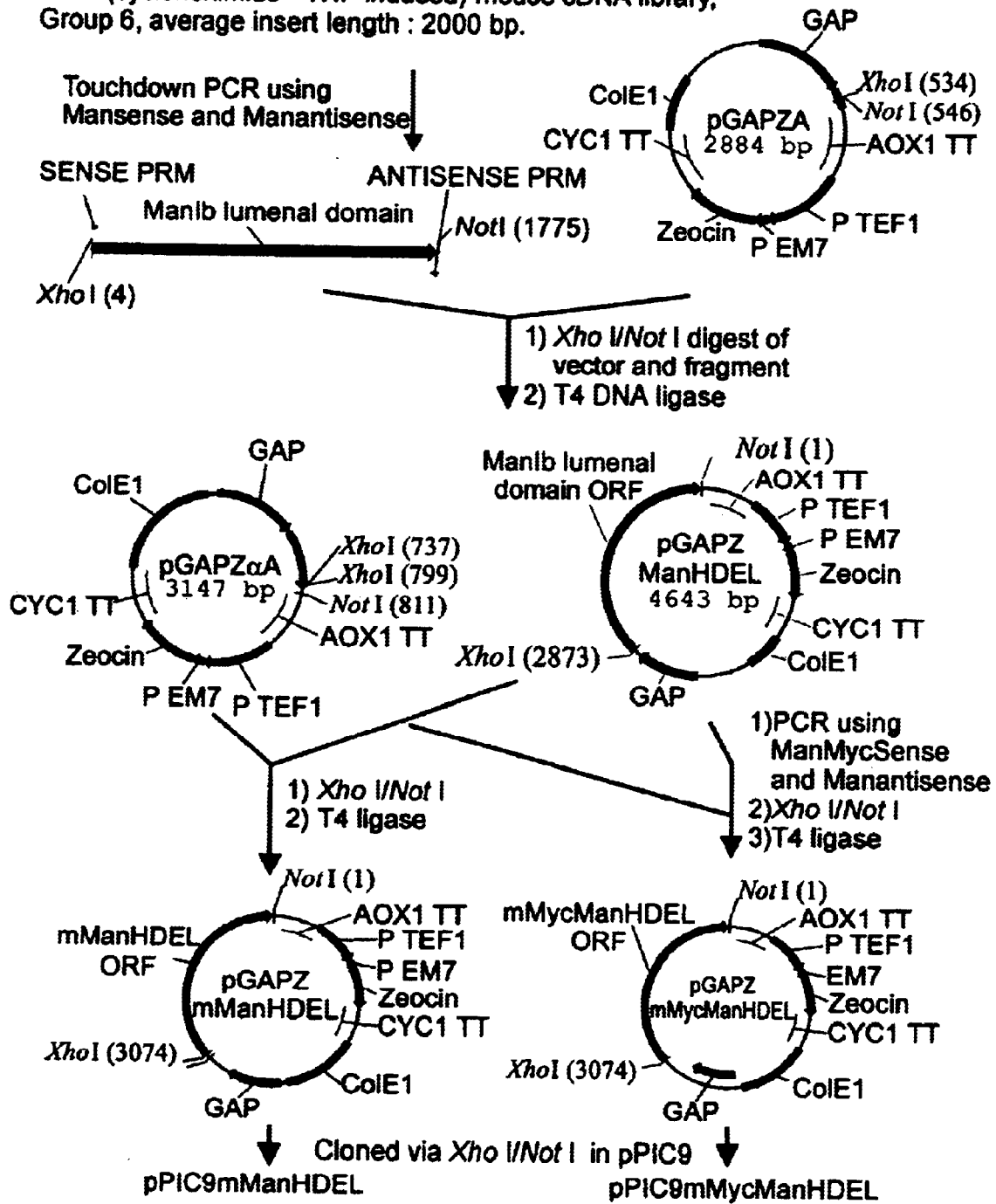
FIG. 2 depicts vectors carrying an HDEL (SEQ ID NO: 1)-tagged *Mus musculus* α-1,2-mannosidase IB expression cassette and describes the way in which these vectors were constructed according to methods known in the art. As can be seen in this figure, the catalytic domain of the *Mus musculus* α-1,2-mannosidase IB was operably linked to the coding sequence for the *S. cerevisiae* α-mating factor secretion signal sequence and further operably linked at the 3' terminus of the coding sequence to the coding sequence for an HDEL (SEQ ID NO: 1) peptide. The whole fission construct was operably linked to either the *P. pastoris* AOX1 promoter (in pPIC9mManHDEL) or to the *P. pastoris* GAP promotor (in pGAPZmManHDEL). Furthermore, variants of the expression cassette were made in which the coding sequence for a cMyc epitope tag was inserted between the coding sequence for the *S. cerevisiae* α-Mating Factor secretion signal sequence and the coding sequence for the catalytic domain of the *Mus musculus* α-1,2-mannosidase IB. This expression cassette was also operably linked to either the *P. pastoris* AOX1 promoter (in pPIC9mMycManHDEL) or the *P. pastoris* GAP promotor (in pGAPZmMycManHDEL).
Figure 3:
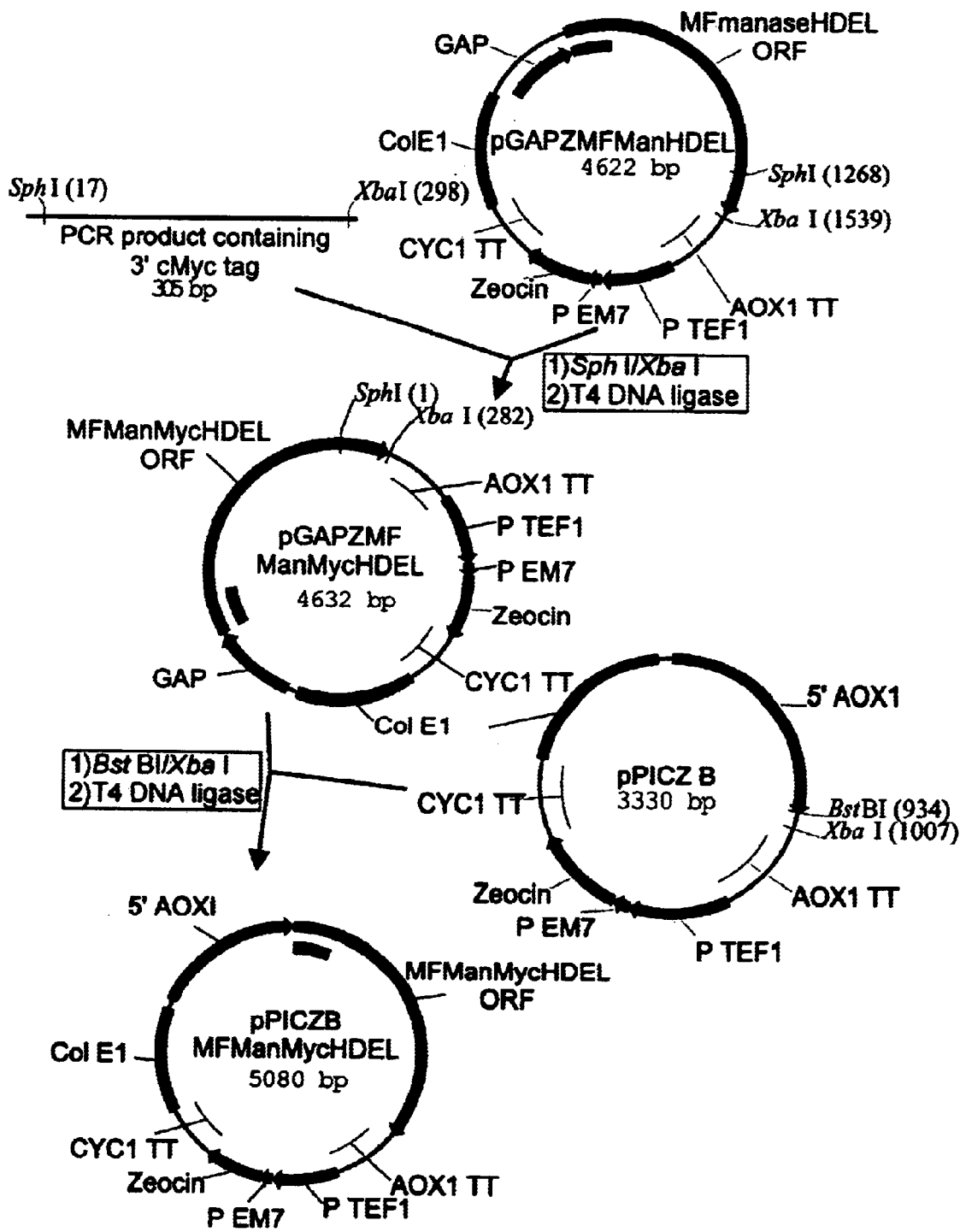
FIG. 3 depicts vectors carrying a MycHDEL tagged *Trichoderma reesei* α-1,2-mannosidase and the way in which these vectors were obtained. The resulting fission construction was again operably linked to either the *P. pastoris* AOX1 promoter (in pPICZBMFManMycHDEL) or to the *P. pastoris* GAP promotor (in pGAPZMFManMycHDEL).

It has been established that the majority of N-glycans on glycoproteins leaving the endoplasmic reticulum (ER) of Pichia have the core $Man_8GlcNAc_2$ oligosaccharide structure. After the proteins are transported from the ER to the Golgi apparatus, additional mannose residues are added to this core sugar moiety by different mannosyltransferases, resulting in glycoproteins with large mannose side chains. Such hyperglycosylation of recombinant glycoproteins is undesirable in many instances. Accordingly, the present invention provides methods and vectors for genetically modifying methylotrophic yeast strains to produce glycoproteins with reduced glycosylation. Methylotrophic yeast strains generated using the present methods and vectors, as well as glycoproteins produced from such genetically modified strains are also provided.

In one embodiment, the present invention provides vectors useful for genetically modifying methylotrophic yeast strains to produce glycoproteins with reduced glycosylation.

In one aspect, the present invention provides "knock-in" vectors which are capable of expressing in a methylotrophic yeast strain one or more proteins whose enzymatic activities lead to a reduction of glycosylation in glycoproteins produced by the methylotrophic yeast strain. According to the present invention, such proteins include, e.g., an α-1,2-mannosidase, a glucosidase II, or functional parts thereof.

In a preferred embodiment, the vectors of the present invention include a sequence coding for an α-1,2-mannosidase or a functional part thereof and are capable of expressing the α-1,2-mannosidase or the functional part in a methylotrophic yeast strain.

An α-1,2-mannosidase cleaves the α-1,2-linked mannose residues at the non-reducing ends of $Man_8GlcNAc_2$, and converts this core oligosaccharide on glycoproteins to $Man_5GlcNAc_2$. In vitro, $Man_5GlcNAc_2$ is a very poor substrate for any Pichia Golgi mannosyltransferase, i.e., mannose residues can not be added to this sugar structure. On the other hand, $Man_5GlcNAc_2$ is the acceptor substrate for the mammalian N-acetylglucosaminyl-transferase I and is an intermediate for the hybrid- and complex-type sugar chains characteristic of mammalian glycoproteins. Thus, by way of introducing an α-1,2-mannosidase into methylotrophic yeasts such as Pichia, glycoproteins with reduced mannose content can be produced.

According to the present invention, the nucleotide sequence encoding an α-1,2-mannosidase for use in the expression vector of the present invention can derive from any species. A number of α-1,2-mannosidase genes have been cloned and are available to those skilled in the art, including mammalian genes encoding, e.g., a murine α-1,2-mannosidase (Herscovics et al. *J. Biol. Chem.* 269: 9864–9871, 1994), a rabbit α-1,2-mannosidase (Lal et al. *J. Biol. Chem.* 269: 9872–9881, 1994) or a human α-1,2-mannosidase (Tremblay et al. *Glycobiology* 8: 585–595, 1998), as well as fungal genes encoding, e.g., an Aspergillus α-1,2-mannosidase (msdS gene), a *Trichoderma reesei* α-1,2-mannosidase (Maras et al. *J. Biotechnol.* 77: 255–263, 2000), or a *Saccharomyces cerevisiae* α-1,2-mannosidase. Protein sequence analysis has revealed a high degree of conservation among the eukaryotic α-1,2-mannosidases identified so far.

Preferably, the nucleotide sequence for use in the present vectors encodes a fungal α-1,2-mannosidase, more preferably, a *Trichoderma reesei* α-1,2-mannosidase, and more particularly, the *Trichoderma reesei* α-1,2-mannosidase described by Maras et al. *J. Biotechnol.* 77: 255–63 (2000).

According to the present invention, the nucleotide sequence can also code for only a functional part of an α-1,2-mannosidase.

By "functional part" is meant a polypeptide fragment of an α-1,2-mannosidase which substantially retains the enzymatic activity of the full-length protein. By "substantially" is meant at least about 40%, or preferably, at least 50% or more of the enzymatic activity of the full-length α-1,2-mannosidase is retained. For example, as illustrated by the present invention, the catalytic domain of the murine α-1,2-mannosidase IB constitutes a "functional part" of the murine α-1,2-mannosidase IB. Those skilled in the art can readily identify and make functional parts of an α-1,2-mannosidase using a combination of techniques known in the art. Predictions of the portions of an α-1,2-mannosidase essential to or sufficient to confer the enzymatic activity can be made based on analysis of the protein sequence. The activity of a portion of an α-1,2-mannosidase of interest, expressed and purified from an appropriate expression system, can be verified using in vitro or in vivo assays described hereinbelow.

In accordance with the present invention, an α-1,2-mannosidase or a functional part thereof expressed in a methylotrophic yeast strain preferably is targeted to a site in the secretory pathway where $Man_8GlcNAc_2$ (the substrate of α-1,2-mannosidase) is already formed on a glycoprotein, but has not reached a Golgi glycosyltransferase which elongates the sugar chain with additional mannose residues.

Accordingly, in a preferred embodiment of the present invention, the α-1,2-mannosidase expression vector is engineered as such that the α-1,2-mannosidase or a functional part thereof expressed from the vector includes an ER-retention signal.

"An ER retention signal" refers to a peptide sequence which directs a protein having such peptide sequence to be transported to and retained in the ER. Such ER retention sequences are often found in proteins that reside and function in the ER.

Multiple choices of ER retention signals are available to those skilled in the art, e.g., the first 21 amino acid residues of the *S. cerevisiae* ER protein MNS1 (Martinet et al. *Biotechnology Letters* 20: 1171–1177, 1998). A preferred ER retention signal for use in the present invention is peptide HDEL (SEQ ID NO: 1). The HDEL (SEQ ID NO: 1) peptide sequence, found in the C-terminus of a number of yeast proteins, acts as a retention/retrieval signal for the ER (Pelham *EMBO J.* 7: 913–918, 1988). Proteins with an HDEL (SEQ ID NO: 1) sequence are bound by a membrane-bound receptor (Erd2p) and then enter a retrograde transport pathway for return to the ER from the Golgi apparatus.

According to the present invention, an ER retention signal can be placed anywhere in the protein sequence of an α-1,2-mannosidase, but preferably at the C-terminus of the α-1,2-mannosidase.

The α-1,2-mannosidase for use in the present invention can be further modified, e.g., by insertion of an epitope tag to which antibodies are available, such as Myc, HA, FLAG and His6 tags well-known in the art. An epitope-tagged α-1,2-mannosidase can be conveniently purified, or monitored for both expression and intracellular localization.

An ER retention signal and an epitope tag can be readily introduced into a protein of interest by inserting nucleotide sequences coding for such signal or tag into the nucleotide sequence encoding the protein of interest, using any of the molecular biology techniques known in the art.

In another preferred embodiment, the vectors of the present invention include a sequence coding for a glucosidase II or a functional part thereof and are capable of expressing the glucosidase II or the functional part in the methylotrophic yeast strain.

It has been established that the initial N-linked oligosaccharide ($Glc_3Man_9GlcNAc_2$), transferred in the ER onto a protein, is cleaved in the ER by specific glucosidases to remove the glucose residues, and by a mannosidase to remove one specific α-1,2-linked mannose. It has been observed by the present inventors that some recombinant proteins expressed in Pichia have residual glucose residues on the sugar moiety when such proteins leave the ER for the Golgi apparatus. The residual glucose molecules present on the sugar structure prevent the complete digestion of the sugar moiety by an α-1,2-mannosidase, and the introduction of an exogenous glucosidase can facilitate the removal of these glucose residues.

According to the present invention, the nucleotide sequence encoding a glucosidase II can derive from any species. Glucosidase II genes have been cloned from a number of mammalian species including rat, mouse, pig and human. The glucosidase II protein from these mammalian species consists of an alpha and a beta subunit. The alpha subunit is about 110 kDa and contains the catalytic activity of the enzyme, while the beta subunit has a C-terminal HDEL (SEQ ID NO: 1) ER-retention sequence and is believed to be important for the ER localization of the enzyme. The glucosidase II gene from *S. cerevisiae* has also been cloned (ORF YBR229c, located on chromosome II). This gene encodes a protein of about 110 kDa, which shows a high degree of homology to the mammalian alpha subunits.

A preferred glucosidase II gene for use in the present vectors is from a fungal species such as *Pichia pastoris* and *S. cerevisiae*. An example of a fungal glucosidase II gene is the *S. cerevisiae* glucosidase II alpha subunit gene.

According to the present invention, the nucleotide sequence can also encode only a functional part of a glucosidase II. By "functional part" is meant a polypeptide fragment of a glucosidase II which substantially retains the enzymatic activity of the full-length protein. By "substantially" is meant at least about 40%, or preferably, at least 50% or more of the enzymatic activity of the full-length glucosidase II is retained. Functional parts of a glucosidase II can be identified and made by those skilled in the art using a variety of techniques known in the art.

In a preferred embodiment of the present invention, the glucosidase II protein is engineered to include an ER retention signal such that the protein expressed in a methylotrophic yeast strain is targeted to the ER and retains therein for function. ER retention signals are as described hereinabove, e.g., the HDEL (SEQ ID NO: 1) peptide sequence.

The glucosidase II for use in the present invention can be further modified, e.g., by insertion of an epitope tag to which antibodies are available, such as Myc, HA, FLAG, and His6 tag, which are well-known in the art.

According to the present invention, the "knock-in" vectors can include either or both of an α-1,2-mannosidase coding sequence and a glucosidase II coding sequence.

Further according to the present invention, the nucleotide sequence coding for the enzyme to be expressed (e.g., an α-1,2-mannosidase or a functional part thereof, or a glucosidase II or a functional part thereof) can be placed in an operable linkage to a promoter and a 3' termination sequence.

Promoters appropriate for expression of a protein in a methylotrophic yeast can include both constitutive promoters and inducible promoters. Constitutive promoters include e.g., the *Pichia pastoris* glyceraldehyde-3-phosphate dehydrogenase promoter ("the GAP promoter"). Examples of inducible promoters include, e.g., the *Pichia pastoris* alcohol oxidase I promoter ("the AOX1 promoter") (U.S. Pat. No. 4,855,231), or the *Pichia pastoris* formaldehyde dehydrogenase promoter ("the FLD promoter") (Shen et al. Gene 216: 93–102, 1998).

3' termination sequences are sequences 3' to the stop codon of a structural gene which function to stabilize the mRNA transcription product of the gene to which the sequence is operably linked, such as sequences which elicit polyadenylation. 3' termination sequences can be obtained from Pichia or other methylotrophic yeast. Examples of *Pichia pastoris* 3' termination sequences useful for the practice of the present invention include termination sequences from the AOX1 gene, p40 gene, HIS4 gene and FLD1 gene.

The vectors of the present invention preferably contain a selectable marker gene. The selectable marker may be any gene which confers a selectable phenotype upon a methylotrophic yeast strain and allows transformed cells to be identified and selected from untransformed cells. The selectable marker system may include an auxotrophic mutant methylotrophic yeast strain and a wild type gene which complements the host's defect. Examples of such systems include the *Saccharomyces cerevisiae* or *Pichia pastoris* HIS4 gene which may be used to complement his4 Pichia strains, or the *S. cerevisiae* or *Pichia pastoris* ARG4 gene which may be used to complement *Pichia pastoris* arg mutants. Other selectable marker genes which function in *Pichia pastoris* include the $Zeo^R$ gene, the $G418^R$ gene, and the like.

The vectors of the present invention can also include an autonomous replication sequence (ARS). For example, U.S. Pat. No. 4,837,148 describes autonomous replication sequences which provide a suitable means for maintaining plasmids in *Pichia pastoris*. The disclosure of U.S. Pat. No. 4,837,148 is incorporated herein by reference.

The vectors can also contain selectable marker genes which function in bacteria, as well as sequences responsible for replication and extrachromosomal maintenance in bacteria. Examples of bacterial selectable marker genes include ampicillin resistance ($Amp^r$), tetracycline resistance ($Tet^r$), neomycin resistance, hygromycin resistance, and zeocin resistance ($Zeo^R$) genes.

According to the present invention, the nucleotide sequence encoding the protein to be expressed in a methylotrophic yeast can be placed in an integrative vector or a replicative vector (such as a replicating circular plasmid).

Integrative vectors are disclosed, e.g., in U.S. Pat. No. 4,882,279 which is incorporated herein by reference. Integrative vectors generally include a serially arranged sequence of at least a first insertable DNA fragment, a selectable marker gene, and a second insertable DNA fragment. The first and second insertable DNA fragments are each about 200 nucleotides in length and have nucleotide sequences which are homologous to portions of the genomic DNA of the species to be transformed. A nucleotide sequence containing a structural gene of interest for expression is inserted in this vector between the first and second insertable DNA fragments whether before or after the marker gene. Integrative vectors can be linearized prior to yeast transformation to facilitate the integration of the nucleotide sequence of interest into the host cell genome.

Replicative and integrative vectors carrying either or both of an α-1,2-mannosidase coding sequence or a glucosidase II coding sequence can be constructed by standard techniques known to one of ordinary skill in the art and found, for example, in Sambrook et al. (1989) in Molecular Cloning: *A Laboratory Manual*, or any of a myriad of laboratory manuals on recombinant DNA technology that are widely available.

Preferred vectors of the present invention carrying an α-1,2-mannosidase expression sequence include pGAPZMFManHDEL, pGAPZMFManMycHDEL, pPICZBMFManMycHDEL, pGAPZmManHDEL, pGAPZmMycManHDEL, pPIC9mMycManHDEL and pGAPZmMycManHDEL, which are further described in the Examples hereinbelow.

Preferred vectors of the present invention carrying a glucosidase II expression sequence include pGAPZAGLSII, pPICZAGLSII, pAOX2ZAGLSII, pYPTIZAGLSII, pGAPADE1glsII, pPICADE1glsII, pAOX2ADE1glsII, pYPTIADE1glsII, pGAPZAglsIIHDEL and pGAPADE1glsIIHDEL, which are further described in the Examples hereinbelow.

In another aspect, the present invention provides "knock-out" vectors which, when introduced into a methylotrophic yeast strain, inactivate or disrupt a gene thereby facilitating the reduction in the glycosylation of glycoproteins produced in the methylotrophic yeast strain.

In one embodiment, the present invention provides a "knock-out" vector which, when introduced into a methylotrophic yeast strain, inactivates or disrupts the Och1 gene.

The *S. cerevisiae* OCH1 gene has been cloned (Nakayama et al. *EMBO J.* 11: 2511–2519, 1992). It encodes a membrane bound α-1,6-mannosyltransferase, localized in the early Golgi complex, that is functional in the initiation of α-1,6-polymannose outer chain addition to the N-linked core oligosaccharide (Man$_5$GlcNAc$_2$ and Man$_8$GlcNAc$_2$) (Nakanishi-Shindo et al. *J. Biol Chem.* 268: 26338–26345, 1993).

A Pichia sequence has been described in Japanese Patent Application No. 07145005 that encodes a protein highly homologous to the *S. cerevisiae* OCH1. For purpose of the present invention, this sequence is denoted herein as "the Pichia OCH1 gene". Those skilled in the art can isolate the OCH1 genes from other methylotrophic yeasts using techniques well known in the art.

According to the present invention, a disruption in the OCH1 gene of a methylotrophic yeast can result in either the production of an inactive protein product or no product. The disruption may take the form of an insertion of a heterologous DNA sequence into the coding sequence and/or the deletion of some or all of the coding sequence. Gene disruptions can be generated by homologous recombination essentially as described by Rothstein (in *Methods in Enzymology*, Wu et al., eds., vol 101:202–211, 1983).

To disrupt the Och1 gene by homologous recombination, an Och1 knock-out vector can be constructed in such a way to include a selectable marker gene. The selectable marker gene is operably linked, at both 5' and 3' end, to portions of the Och1 gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance on yeast cells, or the lacZ gene, which results in blue colonies due to the expression of active β-galactosidase. Linearized DNA fragments of an Och1 knock-out vector are then introduced into host methylotrophic yeast cells using methods well known in the art. Integration of the linear fragments into the genome and the disruption of the Och1 gene can be determined based on the selection marker and can be verified by, for example, Southern Blot analysis.

Alternatively, an Och1 knock-out vector can be constructed in such a way to include a portion of the Och1 gene to be disrupted, which portion is devoid of any Och1 promoter sequence and encodes none or an inactive fragment of the Och1protein. By "an inactive fragment", it is meant a fragment of the Och1 protein which has, preferably, less than about 10% and most preferably, about 0% of the activity of the full-length OCH1 protein. Such portion of the OCH1 gene is inserted in a vector in such a way that no known promoter sequence is operably linked to the OCH1 sequence, but that a stop codon and a transcription termination sequence are operably linked to the portion of the Och1 gene. This vector can be subsequently linearized in the portion of the OCH1 sequence and transformed into a methylotrophic yeast strain using any of the methods known in the art. By way of single homologous recombination, this linearized vector is then integrated in the OCH1 gene. Two Och1sequences are produced in the chromosome as a result of the single homologous recombination. The first Och1 sequence is the portion of the Och1 gene from the vector, which is now under control of the OCH1 promoter of the host methylotrophic yeast, yet cannot produce an active OCH1 protein as such Och 1 sequence codes for no or an inactive fragment of the OCH1 protein, as described hereinabove. The second Och1 sequence is a full OCH1 coding sequence, but is not operably linked to any known promoter sequence and thus, no active messenger is expected to be formed for synthesis of an active OCH1 protein. Preferably, an inactivating mutation is introduced in the OCH1 sequence, to the 5' end of the site of linearization of the vector and to the 3' end of the translation initiation codon of OCH1. By "inactivating mutation" it is meant a mutation introducing a stop codon, a frameshift mutation or any other mutation causing a disruption of the reading frame. Such mutation can be introduced into an Och1 sequence using any of the site directed mutagenesis methods known in the art. Such inactivating mutation ensures that no functional OCH1 protein can be formed even if there exist some promoter sequences 5' to the Och1 sequence in the knock-out vector.

A preferred Och1 knock-out vector of the present invention is pBLURA5 'PpOCH1.

If desired, either or both of a mannosidase expression sequence and a glucosidase expression sequence can be carried on the same plasmid used to disrupt the OCH1 gene to create a "knock-in-and-knock-out" vector.

Additionally, any of the above-described vectors can further include a nucleotide sequence capable of expressing a glycoprotein of interest in a methylotrophic yeast strain.

Another aspect of the present invention is directed to methods of modifying methylotrophic yeast strains to reduce glycosylation on proteins produced by the methylotrophic yeast strains. In accordance with the present methods, methylotrophic yeast strains are modified by transforming into these yeast strains with one or more, i.e., at least one, knock-in and/or knock-out vectors of the present invention as described herein above.

Methylotrophic yeast strains which can be modified using the present methods include but are not limited to yeast capable of growth on methanol such as yeasts of the genera Candida, Hansenula, Torulopsis, and Pichia. A list of species which are exemplary of this class of yeasts can be found in C. Anthony (1982), *The Biochemistry of Methylotrophs*, 269. *Pichia pastoris, Pichia methanolica, Pichia anomola, Hansenula polymorpha* and *Candida boidinii* are examples of methylotrophic yeasts useful in the practice of the present invention. Preferred methylotrophic yeasts are of the genus Pichia. Especially preferred are *Pichia pastoris* strains GS115 (NRRL Y-15851); GS190 (NRRL Y-18014) disclosed in U.S. Pat. No. 4,818,700; PPF1 (NRRL Y-18017) disclosed in U.S. Pat. No. 4,812,405; PPY120H and yGC4; as well as strains derived therefrom.

Methylotrophic yeast strains which can be modified using the present methods also include those methylotrophic yeast strains which have been genetically engineered to express one or more heterologous glycoproteins of interest. The glycosylation on the heterologous glycoproteins expressed from these previously engineered strains can be reduced by transforming such strains with one or more of the vectors of the present invention.

The vectors of the present invention can be introduced into the cells of a methylotrophic yeast strain using known methods such as the spheroplast technique, described by Cregg et al. 1985, or the whole-cell lithium chloride yeast transformation system, Ito et al. *Agric. Biol. Chem.* 48:341, modified for use in Pichia as described in EP 312,934. Other published methods useful for transformation of the plasmids or linear vectors include U.S. Pat. No. 4,929,555; Hinnen et al. *Proc. Nat. Acad. Sci. USA* 75:1929 (1978); Ito et al. *J. Bacteriol.* 153:163 (1983); U.S. Pat. No. 4,879,231; Sreekrishna et al. *Gene* 59:115 (1987). Electroporation and PEG1000 whole cell transformation procedures may also be used. Cregg and Russel *Methods in Molecular Biology: Pichia Protocols,* Chapter 3, Humana Press, Totowa, N.J., pp. 27–39 (1998).

Transformed yeast cells can be selected by using appropriate techniques including but not limited to culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by e.g., Southern Blot or PCR analysis.

In one embodiment, a methylotrophic yeast strain is transformed with a vector which includes a nucleotide sequence coding for an α-1,2-mannosidase or a functional part thereof. The nucleotide sequence is capable of expressing the α-1,2-mannosidase or the functional part in the methylotrophic yeast strain, and is, preferably, integrated into the genome of the methylotrophic yeast strain.

The expression of an α-1,2-mannosidase introduced in a methylotrophic yeast strain can be verified both at the mRNA level, e.g., by Northern Blot analysis, and at the protein level, e.g., by Western Blot analysis. The intracellular localization of the protein can be analyzed by using a variety of techniques, including subcellular fractionation and immunofluorescence experiments. An ER localization of an α-1,2-mannosidase can be determined by co-sedimentation of this enzyme with a known ER resident protein (e.g., Protein Disulfide Isomerase) in a subcellular fractionation experiment. An ER localization can also be determined by an immunofluorescence staining pattern characteristic of ER resident proteins, typically a perinuclear staining pattern.

To confirm that an α-1,2-mannosidase or a functional part thereof expressed in a methylotrophic yeast strain has the expected mannose-trimming activity, both in vitro and in vivo assays can be employed. Typically, an in vitro assay involves digestion of an in vitro synthesized substrate, e.g., $Man_8GlcNAc_2$, with the enzyme expressed and purified from a methylotrophic yeast strain, and assessing the ability of such enzyme to trim $Man_8GlcNAc_2$ to, e.g., $Man_5GlcNAc_2$. In in vivo assays, the α-1,2-mannosidase or a part thereof is co-expressed in a methylotrophic yeast with a glycoprotein known to be glycosylated with N-glycans bearing terminal α-1,2-linked mannose residues in such yeast. The enzymatic activity of such an α-1,2-mannosidase or a part thereof can be measured based on the reduction of the number of α-1,2-linked mannose residues in the structures of the N-glycans of the glycoprotein. In both in vitro and in vivo assays, the composition of a carbohydrate group can be determined using techniques that are well known in the art and are illustrated in the Examples hereinbelow.

In another embodiment, a methylotrophic yeast strain is transformed with a vector which includes a nucleotide sequence coding for a glucosidase II or a functional part thereof. The nucleotide sequence is capable of expressing the glucosidase II or the functional part in the methylotrophic yeast strain, and is, preferably, integrated into the genome of the methylotrophic yeast strain.

The enzymatic activity of a glucosidase II or a functional part thereof expressed in a transformed methylotrophic yeast strain can be assessed using a variety of assays. For example, methylotrophic yeast cells transformed with a sequence encoding a glucosidase II or a part thereof can be set to grow on solid medium containing a substrate of the glucosidase, e.g., 5-bromo-4-chloro-3-indolyl-α-D-glucopyranoside or 4-MU-α-D-Glc. When the enzyme is expressed by the Pichia and secreted extracellularly, the substrate is acted upon by the enzyme, giving rise to detectable signals around the colonies such as blue color or fluorescent glow. Alternatively, liquid culture medium containing the expressed protein molecules can be collected and incubated in test tubes with a substrate, e.g., p-nitrophenyl-α-D-glucopyranoside. The enzymatic activity can be determined by measuring the specific product released. Moreover, in vivo assays can be employed, where a glucosidase II is co-expressed in yeast with a glycoprotein known to be N-glycosylated with glucose residues, e.g., influenza neuraminidase. The enzymatic activity of the glucosidase II can be measured based on the reduction of the glucose content in the sugar chain(s) of the glycoprotein.

In still another embodiment of the present invention, a methylotrophic yeast strain is transformed with an Och1 knock-out vector. As a result of the transformation and integration of the vector, the genomic Och1 gene in the yeast strains is disrupted.

In a further embodiment of the present invention, a methylotrophic yeast strain is transformed with any combination of an α-1,2-mannosidase expression vector, a glucosidase II expression vector, and an Och1 knock-out vector. Such modification can be achieved by serial, consecutive transformations, i.e., introducing one vector at a time, or alternatively by co-transformation, i.e., introducing the vectors simultaneously.

The modified methylotrophic yeast strains described herein above can be further modified if desired. For example, additional disruption of genes encoding any other Pichia mannosyltransferases can be made. Genes encoding mammalian enzymes can also be introduced to produce glycoproteins having hybrid- or complex-type N-glycans, if desired.

Methylotrophic yeast strains which are modified by using the present methods, i.e., by transforming with one or more of the vectors of the present invention, form another embodiment of the present invention.

It should be understood that certain aspects of the present invention, especially the introduction of an intracellularly expressed α-1,2-mannosidase activity, are also useful to obtain a reduced glycosylation of the O-linked glycans on glycoproteins produced in a methylotrophic yeast, as it is known in the art that these O-linked glycans consist mainly of α-1,2-linked mannose residues. O-linked glycans as used herein refers to carbohydrate structures linked to serine or threonine residues of glycoproteins.

A further aspect of the invention is directed to methods of producing a glycoprotein with reduced glycosylation in a methylotrophic yeast, especially a glycoprotein heterologous to the methylotrophic yeast.

"A glycoprotein" as used herein refers to a protein which, in methylotrophic yeasts, is either glycosylated on one or more asparagines residues or on one or more serine or threonine residues, or on both asparagines and serine or threonine residues.

The term "reduced glycosylation" refers to a reduced size of the carbohydrate moiety on the glycoprotein, particularly with fewer mannose residues, when the glycoprotein is expressed in a methylotrophic yeast strain which has been modified in accordance with the present invention, as compared to a wild type, unmodified strain of the methylotrophic yeast.

In accordance with the present invention, the production of a glycoprotein of interest with reduced glycosylation can be achieved in a number of ways. A nucleotide sequence capable of expressing a glycoprotein can be introduced into a methylotrophic yeast strain which has been previously modified in accordance with the present invention, i.e., a strain transformed with one or more of the vectors of the present invention and capable of producing glycoproteins with reduced glycosylation. Alternatively, a methylotrophic yeast strain which has already been genetically engineered to express a glycoprotein can be transformed with one or more of the vectors of the present invention. Otherwise, if a methylotrophic yeast strain does not express a glycoprotein of interest, nor is the strain transformed with any of the vectors of the present invention, such yeast strain can be transformed, either consecutively or simultaneously, with both a nucleotide sequence capable of expressing the glycoprotein and one or more vectors of the present invention. Additionally, a methylotrophic yeast strain can be transformed with one or more of the present knock-in and/or knock-out vectors which also include a nucleotide sequence capable of expressing a glycoprotein in the methylotrophic yeast strain.

The nucleotide sequence capable of expressing a glycoprotein in a methylotrophic yeast can be made to include from 5' to 3', a promoter, a sequence encoding the glycoprotein, and a 3' termination sequence. Promoters and 3' termination sequences which are suitable for expression of a glycoprotein can include any of those promoters and 3' termination sequences described hereinabove.

The nucleotide sequence for expression of a glycoprotein can include additional sequences, e.g., signal sequences coding for transit peptides when secretion of a protein product is desired. Such sequences are widely known, readily available and include Saccharomyces cerevisiae alpha mating factor prepro (αmf), Pichia pastoris acid phosphatase (PHO1) signal sequence and the like.

The nucleotide sequence for expression of a glycoprotein can be placed on a replicative vector or an integrative vector. The choice and construction of such vectors are as described hereinabove.

The nucleotide sequence capable of expressing a glycoprotein can be carried on the same replicative plasmid as a plasmid-borne α-1,2-mannosidase or glucosidase II expression unit. Alternatively, the nucleotide sequence containing the glycoprotein coding sequence is carried on a separate plasmid or integrated into the host genome.

Glycoproteins produced can be purified by conventional methods. Purification protocols can be determined by the nature of the specific protein to be purified. Such determination is within the ordinary level of skill in the art. For example, the cell culture medium is separated from the cells and the protein secreted from the cells can be isolated from the medium by routine isolation techniques such as precipitation, immunoadsorption, fractionation or a variety of chromatographic methods.

Glycoproteins which can be produced by the methods of the present invention include, e.g., Bacillus amyloliquefaciens α-amylase, S. cerevisiae invertase, Trypanosoma cruzi trans-sialidase, HIV envelope protein, influenza virus A haemagglutinin, influenza neuraminidase, Bovine herpes virus type-1 glycoprotein D, human angiostatin, human B7-1, B7-2 and B-7 receptor CTLA-4, human tissue factor, growth factors (e.g., platelet-derived growth factor), tissue plasminogen activator, plasminogen activator inhibitor-I, urokinase, human lysosomal proteins such as α-galactosidase, plasminogen, thrombin, factor XIII and immunoglobulins. For additional useful glycoproteins which can be expressed in the genetically engineered Pichia strains of the present invention, see Bretthauer and Castellino, Biotechnol. Appl. Biochem. 30: 193–200 (1999), and Kukuruzinska et al. Ann Rev. Biochem. 56: 915–44 (1987).

Glycoproteins produced by using the methods of the present invention, i.e., glycoproteins with reduced glycosylation, are also part of the present invention.

Still another aspect of the present invention provides kits which contain one or more of the knock-in vectors, knock-out vectors, or knock-in-and-knock-out vectors of the present invention described above. More particularly, a kit of the present invention contains a vector capable of expressing an α-mannosidase I in a methylotrophic yeast, a vector capable of expressing a glucosidase II in a methylotrophic yeast, a vector capable of disrupting the Och1 gene in a methylotrophic yeast, a vector capable of expressing both a glucosidase II and an α-mannosidase, a vector a vector capable of disrupting the Och1 gene and capable of expressing either or both of a glucosidase II and an α-mannosidase, or any combinations thereof.

The kit can also include a nucleotide sequence which encodes and is capable of expressing a heterologous glycoprotein of interest. Such nucleotide sequence can be provided in a separate vector or in the same vector which contains sequences for knocking-in or knocking out as described hereinabove.

In addition, the kit can include a plasmid vector in which a nucleotide sequence encoding a heterologous protein of interest can be subsequently inserted for transformation into and expression in a methylotrophic yeast. Alternatively, the knock-in or knock-out vectors in the kits have convenient cloning sites for insertion of a nucleotide sequence encoding a heterologous protein of interest.

The kit can also include a methylotrophic yeast strain which can be subsequently transformed with any of the knock-in, knock-out or knock-in-and-knock-out vectors described hereinabove. The kit can also include a methylotrophic yeast strain which has been transformed with one or more of the knock-in or knock-out vectors. Furthermore, the kit can include a methylotrophic yeast strain which has been transformed with a nucleotide sequence encoding and capable of expressing a heterologous glycoprotein of interest.

The present invention is further illustrated by the following examples.

EXAMPLE 1

Introduction of α-1,2-Mannosidase to the ER-Golgi Border

1.1 Plasmids

| Plasmid | Promoter | Enzyme | Tag |
|---|---|---|---|
| pGAPZMFManHDEL | GAP | T. reesei α-1,2-mannosidase | — |

-continued 1.1 Plasmids

| Plasmid | Promoter | Enzyme | Tag |
|---|---|---|---|
| pGAPZMFManMycHDEL | GAP | T. reesei α-1,2-mannosidase | Myc |
| pPICZBMFManMycHDEL | AOX1 | T. reesei α-1,2-mannosidase | Myc |
| pGAPZMFmManHDEL | GAP | mouse mannosidase IB catalytic domain | — |
| pGAPZMFmMycManHDEL | GAP | mouse mannosidase IB catalytic domain | Myc |

The *Trichoderma reesei* α-1,2-mannosidase gene has been isolated and described by Maras et al. (*J. Biotechnol.* 77;255–263, 2000). The sequence of this gene is available at NCBI Genbank under Accession No. AF212153. A construction fragment was generated by PCR using the pPIC9MFmanase plasmid (same as pPP1MFmds1 described by Maras et al. (2000)) as the template and using the following oligonucleotide primers: 5'-GACTGGTTCCAATTGACAAGC-3' (SEQ ID NO:2) and 5'-AGTCTAGATTACAACTCGTCGTGAGCAAGGTG GCCGCCCCG TCG-3' (SEQ ID NO:3). The resulting product contained the 3' end of the *Pichia pastoris* AOXI promoter, the prepro-signal sequence of the *S. cerevisiae* α-mating factor, the open reading frame of the *Trichoderma reesei* α-1,2-mannosidase cloned in frame with the signal sequence, the coding sequence for HDEL (SEQ ID NO: 1), a stop codon and an Xba I restriction site. This fragment was digested with Eco RI and Xba I, removing the 5' sequences up to the mannosidase ORF, and then cloned into the vector pGAPZαA (Invitrogen, Baam, The Netherlands) which had been digested with Eco RI and Xba I, thus restoring the fusion with the *S. cerevisiae* α-mating factor signal sequence. The resulting plasmid was named pGAPZMF-ManHDEL and is graphically depicted in FIG. 1. The ORF sequence of the MFManHDEL fusion in pGAPZMFMan-HDEL is set forth in SEQ ID NO: 14.

In order to introduce the coding sequence for a c-Myc tag between the catalytic domain and the HDEL (SEQ ID NO: 1)-signal, the 3' end of the ORF of *T. reesei* α-1,2-mannosidase was PCR-amplified using a sense primer 5'-CCATTGAGGACGCATGCCGCGCC-3' (SEQ ID NO: 4) (containing an Sph I restriction site) and an antisense primer GTATCTAGATTACAACTCGTCGTGCA-GATCCTCTTCTGAGATGAGTTTTTGT TCAGCAAG-GTGGCCGCCCCGTCGTGATGATGAA (SEQ ID NO: 5) (containing the coding sequences of the c-Myc tag and the HDEL (SEQ ID NO: 1) signal, followed by a stop codon and an Xba I restriction site). The resulting PCR product was digested with Sph I and Xba I, purified by agarose gel electrophoresis and inserted into pGAPZMFManHDEL which had been cut with the same restriction enzymes, resulting in plasmid pGAPZMFManMycHDEL. To put the ORF of pGAPZMFManMycHDEL under the control of the inducible AOXI promoter, the entire ORF was liberated from pGAPZMFManMycHDEL with Bst BI and Xba I, and cloned in pPICZB (Invitrogen, Baarn, The Netherlands), resulting in pPICZBMFManMycHDEL.

Cloning of the mouse mannosidase IB catalytic domain with concomitant addition of the coding sequence for a C-terminal HDEL (SEQ ID NO: 1)-tag was done by PCR on a mouse cDNA library (mRNA isolated from the L929 cell line induced with cycloheximide and mouse Tumor Necrosis Factor. Average insert length of the cDNA library was 2000 bp). The PCR oligonucleotide primers used were: 5'AACTCGAGATGGACTCTTCAAAACACAAACGC3' (SEQ ID NO: 6) and 5'TTGCGGCCGCTTA-CAACTCGTCGTGTCGGACAGCAGGATTACCTGA3' (SEQ ID NO: 7). The product contained a 5' Xho I site and the coding sequence for C-terminal HDEL (SEQ ID NO: 1)-site, followed by a stop codon and a Not I site at the 3' end. The product was cloned in pGAPZαA via the Xho I/Not I sites in the PCR product and the vector, resulting in an in frame fusion of the mouse mannosidase catalytic domain with the *S. cerevisiae* α-mating factor signal sequence. The sequence of the entire open reading frame generated is set forth in SEQ ID NO: 15.

TABLE 2

1.2 Yeast Transformation and Genomic Integration

| Parental strain | DNA transformed |
|---|---|
| GS115 (his4) | pGAPZMFManHDEL |
| | pPIC9MFManHDEL |
| | pPIC9mManHDEL |
| | pPIC9mMycManHDEL |
| | pGAPZmManHDEL |
| | pGAPZmMycManHDEL |
| GS115 (his4 complemented by pPIC9InfluenzaHA) | pGAPZMFManHDEL |
| | pGAPZmManHDEL |
| | pGAPZmMycManHDEL |
| PPY120H (his4 complemented by pPIC9sOCH1) | pGAPZMFManMycHDEL |
| | pPICZBMFManMycHDEL |
| yGC4 (his4 arg1 ade2 ura3 complemented by pBLURA5'PpOCH1) | pPIC9InfluenzaNeuraminidase |
| | pGAPZMFManHDEL |
| | pPIC9Glucoseoxidase |

All transformations to *Pichia pastoris* were performed with electroporation according to the directions of Invitrogen. Transformants of vectors carrying the Zeocin resistance gene were selected on YPD containing 100 μg/ml Zeocine (Invitrogen, Baarn, the Netherlands) and 1M sorbitol. Selection of transformants of pPIC9 derivatives was done on minimal medium lacking histidine and containing 1M sorbitol. Genomic integration of the expression cassettes was verified using PCR on genomic DNA purified from the Pichia strains using the Yeast Miniprep method (Nucleon). In all cases concerning the *Trichoderma reesei* gene fusions, the primers used were the sense primer 5'-CCATTGAGGACGCATGCCGCGCC-3' (SEQ ID NO: 8), which annealed to the 3' half of the mannosidase ORF, and the antisense primer 3' AOXI 5'-GCAAATGGCATTCTGACATCCT-3' (SEQ ID NO: 9), which annealed to the AOXI transcription terminator that was present in all our expression constructs. For the control of genomic integration of the mouse mannosidase transgenes, PCR was done using the sense primer 5'GAP 5'GTCCCTATTTCAATCAATTGAA3' (SEQ ID NO: 10, annealing to the GAP promoter or 5'AOXI 5'GACTGGT-TCCAATTGACAAGC3' (SEQ ID NO:11), annealing to AOXI promoter), and the antisense primer 3'AOXI (above). For the expression constructs containing a Myc tagged *Trichoderma reesei* α-1,2-mannosidase expression unit, further evidence for genomic integration was obtained using Southern Blotting with the entire MFManMycHDEL ORF ($^{32}$P labelled using HighPrime, Boehringer Mannheim) as a probe.

1.3 Expression of α-1,2-mannosidase

Expression of an α-1,2-Mannosidase in GS 115 strains expressing influenza virus haemagglutinin was verified by qualitative Northern blot. Expression of an α-1,2-Mannosidase in PPY120H strains was verified by anti-Myc Western blot.

Qualitative Northern Blot—Total RNA was purified from Pichia strains and the yield was determined spectrophotometrically. Northern blotting was performed according to standard procedures and an estimate of the quantity of RNA loaded was made using methylene blue staining of the blot, visualizing the rRNA bands. The blot was probed with a ClaI/NarI fragment of the mannosidase, labelled with $^{32}P$ using HighPrime (Boehringer Manmheim).

SDS-PAGE and Western Blotting—Total yeast cell lysates were prepared by washing the cells twice with PBS, followed by boiling in 1 volume of 2× concentrated Laemmli loading buffer for 5 min. The lysate was spun briefly in a microcentrifuge prior to gel loading and only the supernatant was loaded. For the analysis of proteins secreted into the growth media, the proteins were precipitated from 200 μl of these media using desoxycholate/trichloroacetic acid according to standard procedures. The pellet was redissolved in 2× concentrated Laemmli loading buffer and the solutions were pH-corrected using Tris. SDS-PAGE was performed and followed by semidry electroblotting to nitrocellulose membranes. For Western Blotting, the 9E10 anti-Myc and the anti-HA mouse monoclonals (Boehringer Mannheim) were used at a concentration of 1 μg/ml, and the rabbit anti-PDI antiserum (Stressgen) was used at a dilution of 1/500. The secondary antibodies were goat anti-mouse IgG conjugated to alkaline phosphatase for the monoclonals and goat anti-rabbit IgG conjugated to peroxidase for the polyclonal (secondary antibodies from Sigma). Detection was performed using the NBT/BCIP system for alkaline phosphatase and the Renaissance substrate (NENBiosciences) for peroxidase. Imaging of the latter blot result was done on a Lumilager imaging device (Boehringer Mannheim).

Figure 4:
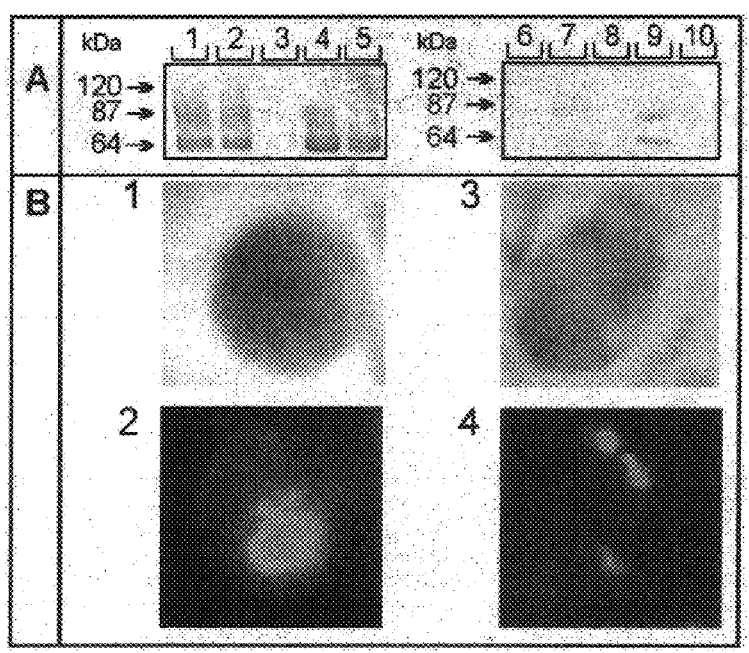
FIG. 4 demonstrates the intracellular localization of the MycHDEL-tagged *Trichoderma reesei* α-1,2-mannosidase and indicates ER-targeting by immunofluorescence analysis. Panel A Western blotting. Yeast strains were grown in 10 ml YPG cultures to an $OD_{600}=10$, diluted fivefold and grown in YPM for 48 h. ⅕₀th of the culture medium and ⅕₅th of the cells were analysed by SDS-PAGE and Western blotting with the mouse monoclonal 9E10 anti-Myc antibody. The position of molecular weight marker proteins are indicated with arrows. Lanes 1–5: cellular lysates. 1,2: pGAPZMF-ManMycHDEL transformants. 3: non-transformed PPY12OH (negative control). 4,5: pPICZBMFManMycH-DEL transformants. Lanes 6–10: culture media. 6: non transformed PPY12OH (negative control). 7,8: pGAPZM-FManMycHDEL transformants. 9,10: pPICZBMFManMycHDEL transformants. Panel B Immunofluorescence microscopy. 1: phase contrast image of a *P. pastoris* cell (strain PPY12OH transformed with pGAPZMFManHDEL) at 1000× magnification. The nucleus is visible as an ellipse in the lower right quadrant of the cell. 2: same cell as in 1, but in fluorescence microscopy mode to show localization of the *T. reesei* mannosidase-Myc-HDEL protein. The protein is mainly localized in a circular distribution around the nucleus (nuclear envelope), which is typical for an endoplasmic reticulum steady-state distribution. 3: phase contrast image of a *P. pastoris* cell (strain PPY12OH transformed with pGAPZMFManHDEL) at 1000× magnification. 4: same cell in fluorescence microscopy to show localization of the Golgi marker protein OCH1-HA in *P. pastoris* strain PPY12OH. The dot-like distribution throughout the cytoplasm, with 3–4 dots per cell is typical for cis-Golgi distribution in *P. pastoris*.

The results shown in FIG. 4 indicated that the great majority of the HDEL (SEQ ID NO: 1)-tagged protein was retained intracellularly, both when expressed from the strong constitutive GAP promoter and when expressed from the strong inducible AOXI promoter.

1.4 Localization of α-1,2-Mannosidase

Isopycnic sucrose density gradient centrifugation—To determine the localization of the HDEL (SEQ ID NO: 1)-tagged mannosidase, subcellular fractionation was carried out using cells expressing the mannosidase-Myc-HDEL from the strong constitutive GAP promoter.

Briefly, 0.5 g of wet weight yeast cells were lysed using 4×1 min vortexing with 4.5 g glass beads in 1 ml lysis-buffer (50 mM Tris-HCL pH 7.5 containing 0.6 M sorbitol, 10 mM β-mercaptoethanol and 5 mM $MgCl_2$). Between vortexing periods, the mixture was placed on ice for 5 min. The supernatant was collected and the glass beads were washed once with lysis-buffer, and the supernatant of this washing step was added to the first supernatant. This lysate was subjected to a differential centrifugation procedure. The P10000 pellet was solubilized in 0.5 ml of a 60% sucrose solution in lysis buffer. This solution was placed at the bottom of an Ultraclear ultracentrifuge tube (Beckman) of 14×89 mm. Subsequently, 1.5 ml each of sucrose solutions of 55, 50, 45, 42.5, 40, and 37.5% were carefully layered over each other. The tube was filled to the edge with 35% sucrose. Isopycnic sucrose gradient centrifugation was performed for 14 h at 180,000 g in a Beckman SW 41 rotor in a Beckman Model L8-70 preparative ultracentrifuge. After completion, 1 ml fractions were collected from the top and partially dialysed from excess sucrose, evaporated to dryness in a vacuum centrifuge. After redissolving the pellet in Laemmli buffer, the samples were subjected to SDS-PAGE in triplicate and the Western blots were treated with anti-HA, anti-Myc or anti-PDI ("PDI" for Protein Disulfide Isomerase), respectively.

Figure 5:
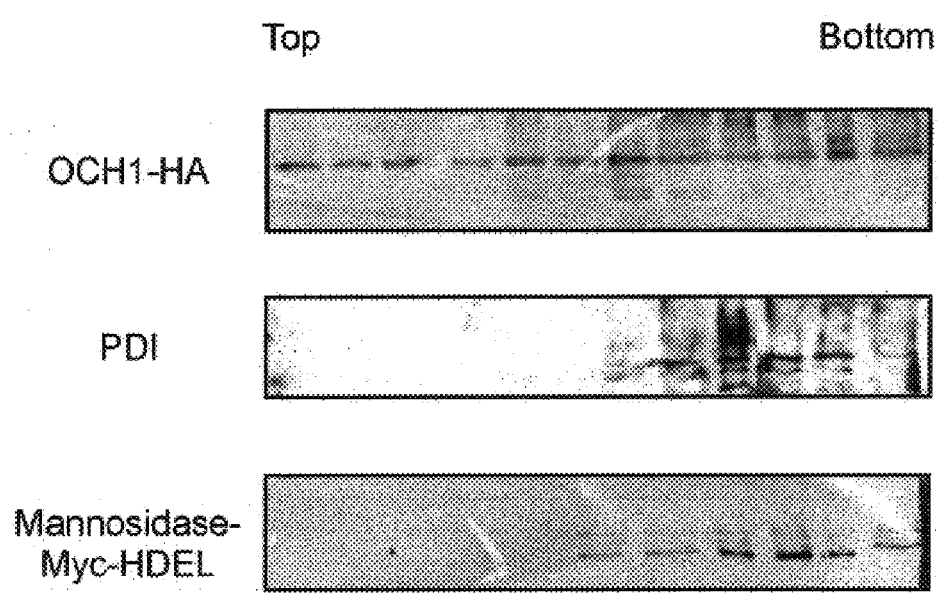
FIG. 5 depicts the co-sedimentation of mannosidase-MycHDEL with Protein Disulfide Isomerase in sucrose density gradient centrifugation. The top panel shows the distribution over the different fractions of the sucrose gradient of the OCH1-HA Golgi marker protein. The middle panel shows this distribution for the Protein Disulfide Isomerase endoplasmic reticulum marker protein. Finally, the bottom panel shows the distribution of the MycHDEL-tagged *Trichoderma reesei* α-1,2-mannosidase over the same fractions. It is concluded that the mannosidase-MycHDEL almost exactly matches the distribution of the ER marker PDI and thus mainly resides in the ER of the *Pichia pastoris* yeast cells.

The results illustrated almost exact cosedimentation of the MFManMycHDEL protein with the Protein Disulfide Isomerase marker protein (which is also targeted with a HDEL (SEQ ID NO: 1) signal sequence) (FIG. 5). In the same assay, the HA-tagged OCH1 was distributed over the whole gradient, with the highest abundance in fractions having a density lower than that of the fractions containing the mannosidase and the PDI. This result indicated that the mannosidase was targeted to the expected location (the ER-Golgi boundary) by the addition of an HDEL (SEQ ID NO: 1) signal. In contrast, the mannosidase without HDEL (SEQ ID NO: 1), expressed from inducible alcohol oxidase I promoter (which was of comparable strength as the GAP promoter), was secreted at a high level of about 20 mg/l.

Immunofluorescence microscopy—To confirm the correct targeting of the mannosidase-Myc-HDEL, an immunofluorescence microscopy experiment was performed.

Briefly, yeast cultures were grown to $OD_{600}$ in YPD (for pGAPZMFManMycHDEL) or in YMP following a YPG-lycerol growth phase for pPICZBMFManMycHDEL. Formaldehyde was added to the yeast cultures to a final concentration of 4% and incubated for 10 min at room temperature. Cells were pelleted and resuspended in 50 mM potassium phosphate buffer pH 6.5 containing 1 mM $MgCl_2$ and 4% formaldehyde and incubated for 2 h at room temperature. After pelleting, the cells were resuspended to an $OD_{600}=10$ in 100 mM potassium phosphate buffer pH 7.5 containing 1 mM $MgCl_2$ and EDTA-free Complete™ protease inhibitor cocktail (Boehringer Mannheim). To 100 μl of cell suspension, 0.6 μl of β-mercapto-ethanol and 20 μl of 20,000 U/ml Zymolyase 100T (ICN) were added, followed by a 25 minute incubation with gentle shaking. The cells were washed twice in the incubation buffer and added to polylysine coated cover slips (these are prepared using adhesive rings normally in use for reinforcing perforations in paper). Excess liquid was blotted with a cotton swab and the cells were allowed to dry at 20° C. All blocking, antibody incubation and washing steps are performed in PBS containing 0.05% bovine serum albumin. Primary antibodies are used at 2 μg/μl and secondary antibodies conjugated to flurophores (Molecular probes) were used at 5 μg/μl. The nucleus was stained with the nucleic acid stain HOECHST 33258. After fixation and cell wall permeabilization, the integrity of the yeast cell morphology was checked in phase contrast microscopy and after immunostaining, the slides were examined under a Zeiss Axiophot fluroresensce microscope equipped with a Kodak digital camera. Images were processed using Macprobe 4.0 software and prepared with Corel Photopaint 9.0.

The Golgi marker protein OCH1-HA gave the typical Golgi staining pattern described in the literature (speckle-like staining). Staining with the 9E 10 monoclonal anti-Myc antibody, recognizing mannosidase-Myc-HDEL, gave a perinuclear staining pattern with some disparate staining in the cytoplasm, highly indicative for an ER targeting (FIG. 4).

Based on the foregoing experiments, it is concluded that the *Trichoderma reesei* mannosidase-Myc-HDEL was targeted to the ER-Golgi boundary.

EXAMPLE 2

Co-expression of Mannosidase-HDEL with Recombinant Glycoproteins

Co-expression of Mannosidase-HDEL with the *Trypanosoma cruzi* trans-Sialidase

The cloning of a *Trypanosoma cruzi* trans-sialidase gene coding for an active trans-sialidase member without the C-terminal repeat domain has been described by Laroy et al. (*Protein Expression and Purification* 20: 389, 2000) which is incorporated herein by reference. The sequence of this *Trypanosoma cruzi* trans-sialidase gene is available through NCBI Genbank under the Accession No. AJ276679. For expression in *P. pastoris*, the entire gene was cloned in pHILD2 (Invitrogen, San Diego, Calif.), creating pHILD2-TS. To allow better secretion, pPIC9-TS was created in which trans-sialidase was linked to the prepro secretion signal of the yeast α-mating factor. Plasmids pPIC9-TSE and pCAGGS-prepro-TSE were created where the epitope E-tag was added to the C-terminal of the trans-sialidase to allow easy detection and purification. The construction of pHILD2-TS, pPIC9-TSE and pCAGGS-prepro-TSE has been described by Laroy et al. (2000), incorporated herein by reference. The vectors used in the construction were made available through BCCM™/LMBP-PLASMID AND cDNA COLLECTION for pCAGGS (No. LMBP 2453), Invitrogen, San Diego, Calif. for pHILD2 and pPIC9, and Pharmacia Biotech for pCANTAB-5E.

Plasmid pPIC9-TSE was linearized with SstI and was transformed into *P. pastoris* GS115 (his4) strain by electroporation according to the manufacturer's instructions (Invitrogen). One of the transformants was further transformed with plasmid pGAPZMFManHDEL, establishing a strain co-expressing Mannosidase-HDEL and the *Trypanosoma cruzi* trans-sialidase.

Fermentation and protein purification was according to the procedures described by Laroy et al. (2000).

Purified trans-sialidase was subject to carbohydrate analysis according to Callewaert et al., *Glycobiology* 11, 4, 275–281, 2001. Briefly, the glycoproteins were bound to the PVDF membrane in the wells of a 96-well plate, reduced, alkylated and submitted to peptide-N-glycosidase F deglycosylation. The glycans were derivatised with 8-amino-1,3, 6-pyrenetrisulfonic acid by reductive amination. Subsequently, the excess free label was removed using Sephadex G10-packed spin columns and the glycans were analysed by electrophoresis on a 36 cm sequencing gel on an ABI 377A DNA-sequencer and detected using the built-in argon laser. Digests with 3 mU/ml purified *T. reesei* α-1,2-mannosidase (described by Maras et al., *J. Biotechnol.* 77, 255–63, 2000) were also performed in 20 mM sodium acetate pH=5.0. The glycans derived from 1 µg of the purifed recombinant glycoproteins were used as the substrate. 1 U of the α-1,2-mannosidase is defined as the amount of enzyme that releases 1 µmol of mannose from baker's yeast mannan per minute at 37° C. and pH=5.0.

Figure 6:
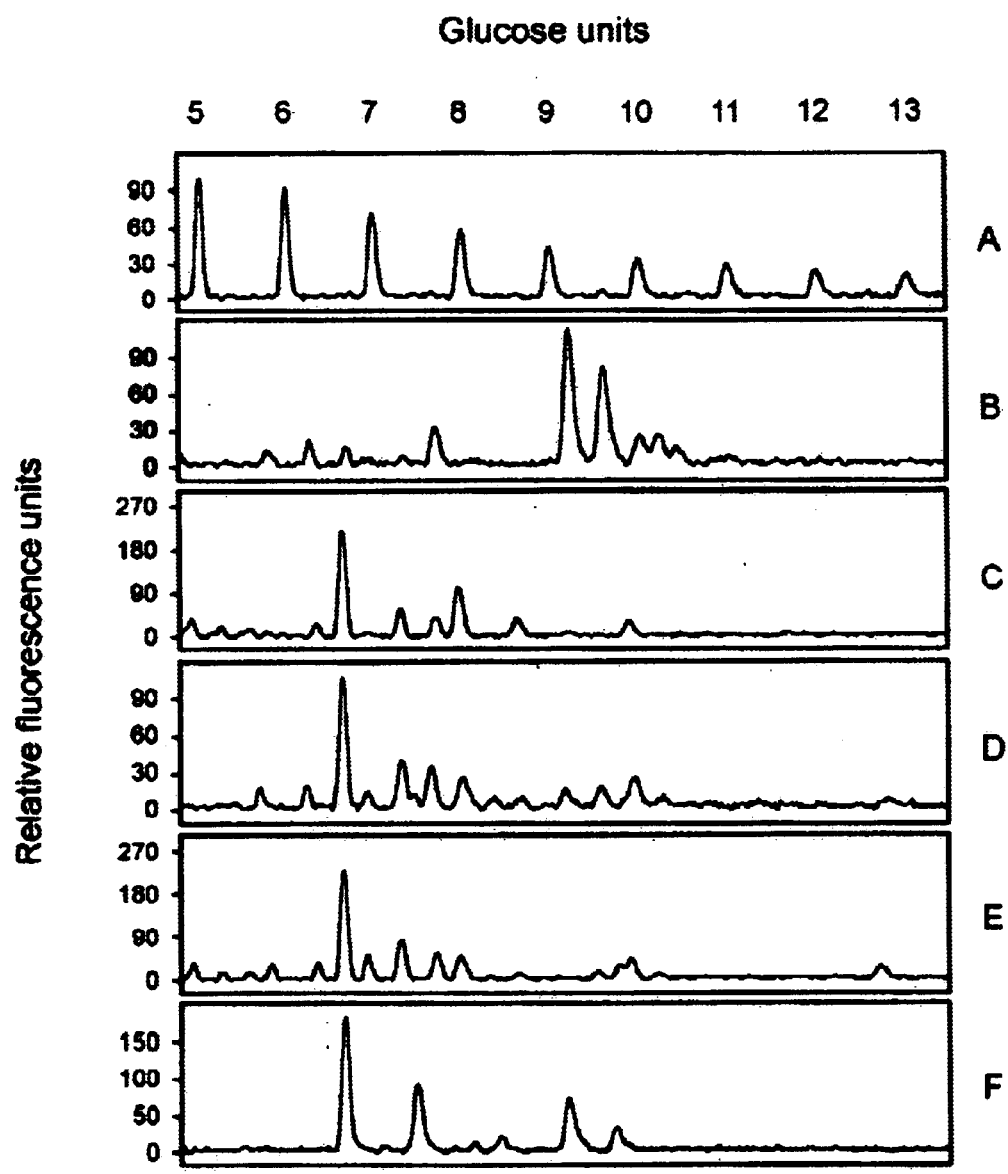
FIG. 6 depicts the N-glycan analysis of *Trypanosoma cruzi* trans-sialidase coexpressed with *Trichoderma reesei* mannosidase-HDEL. Panel A: malto-oligosaccharide size reference ladder. Sizes of the glycans are expressed in Glucose Units (GU) by comparison of their electrophoretic mobility to the mobility of these malto-oligosaccharides. Panel B: N-glycans derived from recombinant *Trypanosoma cruzi* trans-sialidase expressed in *Pichia pastoris*. The peak at GU=9,2 corresponds to $Man_8GlcNAc_2$. Panel C: same analytes as panel 2, but after overnight treatment with 3 U/ml purified recombinant *T. reesei* α-1,2-mannosidase. Panel D: N-glycans derived from recombinant trans-sialidase co-expressed in *Pichia pastoris* with *T. reesei* mannosidase-HDEL (under control of the GAP promotor). The peak at GU=7,6 corresponds to the $Man_5GlcNAc_2$ peak in the profile of RNase B (Panel F). Panel E: same analytes as panel D, but after overnight treatment with 3 mU/ml purified recombinant *T. reesei* α-1,2-mannosidase. Panel F: N-glycans derived from bovine RNase B. These glycans consist of $Man_5GlcNAc_2$ to $Man_8GlcNAc_2$. Different isomers are resolved, accounting for the number of peaks for $Man_7GlcNAc_2$.

As can be seen in FIG. 6, panel B, the major N-glycan on trans-sialidase was $Man_8GlcNAc_2$ (Compare with panel F, representing an analysis of the N-glycans of bovine RNAseB. The one but last peak in this profile is $Man_8GlcNAc_2$, the first peak is $Man_5GlcNAc_2$). In vitro, this glycan was digestible to $Man_5GlcNAc_2$ with α-1,2-mannosidase (FIG. 6, panel C). In the N-glycan profile of the trans-sialidase co-expressed with mannosidase-HDEL, the major peak corresponded to $Man_5GlcNAc_2$ (FIG. 6, panel D).

Co-expression of Mannosidase-HDEL with the Influenza A Virus Haemagglutinin

The Influenza A virus haemagglutinin was known to be glycosylated in *Pichia pastoris* with high-mannose N-glycans containing 9–12 mannose residues (Saelens et al. *Eur. J. Biochem.* 260: 166–175, 1999). The effect of a co-expressed mannosidase on the N-glycans of the haemagglutinin was assessed in an N-glycan profiling method described below. In addition, to compare the efficiency of the Trichoderma enzyme (having a temperature optimum of 60° C.) with a mammalian mannosidase having a temperature optimum of 37° C., the catalytic domain of the mouse mannosidase IB from a mouse cDNA-library was cloned and tagged with a HDEL (SEQ ID NO: 1) signal by PCR amplification. This ORF was cloned after the prepro-signal sequence of the *S. cerevisiae* α-mating factor under the control of the GAP promoter. Expression of the mannosidase-HDEL transgenes on the mRNA level was confirmed by qualitative Northern blotting.

The haemagglutinin was expressed and purified from a non-mannosidase expressing control strain and from a strains co-expressing the *Trichoderma reesei* mannosidase-HDEL or the mouse mannosidase IB-HDEL according to the procedure described by Kulakosky et al. *Glycobiology* 8: 741–745 (1998). The purified haemagglutin was subjected to PNGase F digestion as described by Saelens et al. *Eur. J. Biochem.* 260: 166–175, 1999. The proteins and glycans were precipitated with 3 volumes of ice-cold acetone and the glycans were extracted from the pellet with 60% methanol. Following vacuum evaporation, the glycans were labeled with 8-amino-1,3,6 pyrenetrisulfonic acid by adding 1 µl of a 1:1 mixture of 20 mM APTS in 1.2M citric acid and 1M $N_aCNBH_3$ in DMSO and incubating for 16 h at 37° C. at the bottom of a 250 µl PCR-tube. The reaction was stopped by the addition of 10 µl deionized water and the mixture was loaded on a 1.2 cm Sephadex G10 bed packed to dryness in a microspin-column by centrifugation in a swinging bucket rotor, which provided for a flat resin surface. After loading, 50 µl deionised water was carefully added to the resin bed and the spin column was briefly centrifuged for 5 seconds at 750 g in a tabletop centrifuge. This elution process was repeated twice and all the eluates were pooled and evaporated to dryness in a Speedvac vacuum centrifuge (Savant). The labeled glycans were reconstituted in 1.5 µl gel loading buffer containing 50% formamide and 0.5 µl Genescan 500™, labeled with rhodamine (Perkin Elmer Bioscience), serving as an internal reference standard. This mixture was loaded on a DNA-sequencing gel containing 10% of a 19:1 mixture of acrylamide:bisacrylamide (Biorad, Hercules, Calif., USA) and made up in the standard DNA-sequencing buffer (89 mM Tris, 89 mM borate, 2.2 mM EDTA). Polymerization of the gel was catalyzed by the addition of 200 µl 10% ammononiumpersulfate solution in water and 20 µl TEMED. The gel was of the standard 36 cm well-to-read length and was run on an Applied Biosystems Model 373A DNA-sequencing apparatus. Prerunning of the gel was done at 1000 V for 15 min. and after loading, the gel was electrophoresed for 8 h at 1250 V without heating. This methodology gives a limit of detection of 10 fmol per peak. The data were analysed with Genescan 3.0 software.

Figure 7:
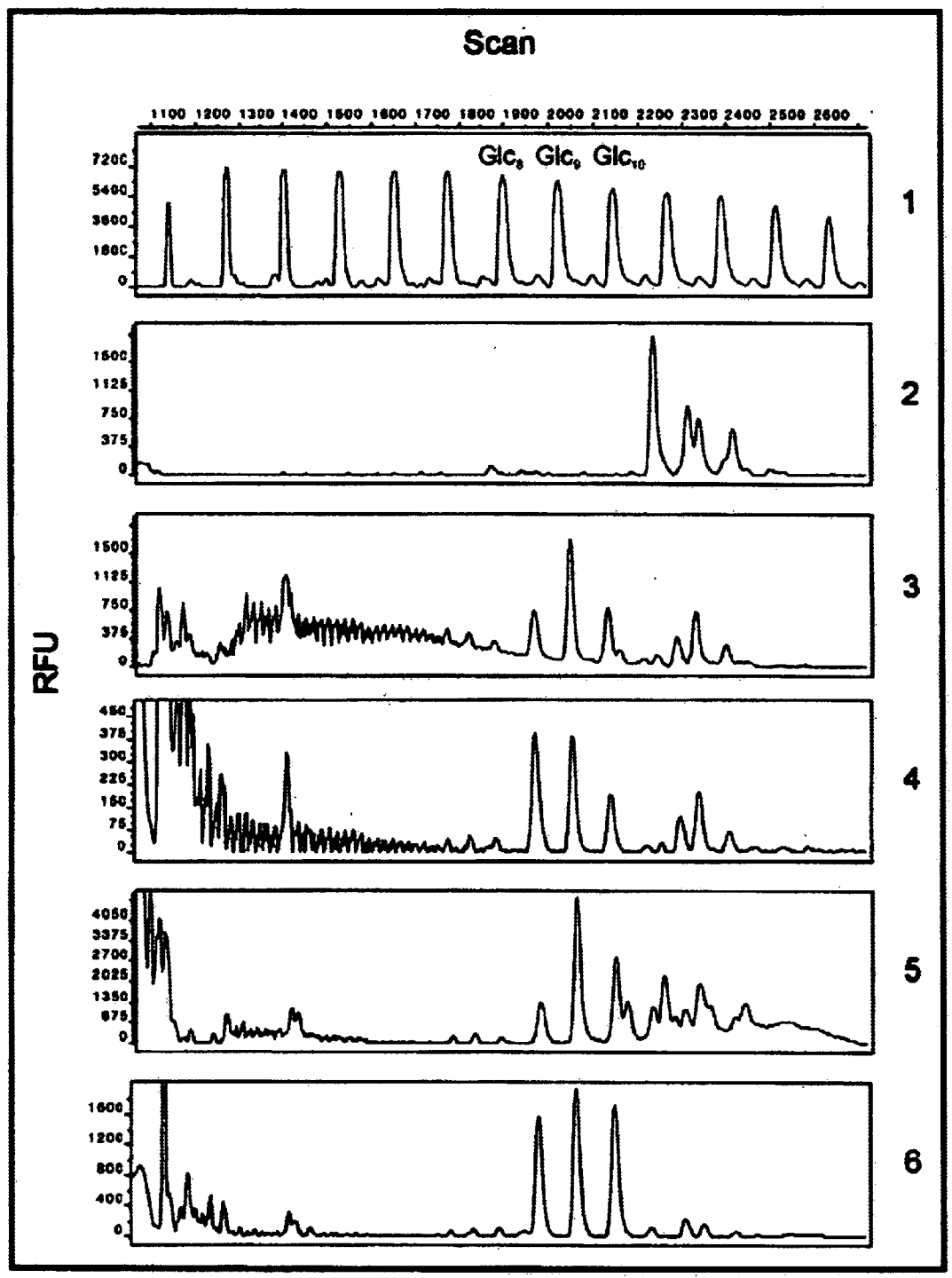
FIG. 7 depicts the processing of influenza haemagglutinin N-glycans by HDEL (SEQ ID NO: 1)-tagged *Trichoderma reesei* α-1,2-mannosidase and the HDEL (SEQ ID NO: 1)-tagged catalytic domain of murine α-1,2-mannosidase IB. The $Man_5GlcNAc_2$ reference oligosaccharide runs at scan 1850 in this analysis (not shown). Panel 1: malto-oligosaccharide size reference ladder. Panel 2: N-glycans derived from recombinant influenza haemagglutinin expressed in *Pichia pastoris*. The peak at scan 2250 corresponds to $Man_9GlcNAc_2$. Panel 3: N-glycans derived from recombinant haemagglutinin co-expressed in *Pichia pastoris* with *T. reesei* mannosidase-HDEL (under control of the GAP promotor). The peak at scan 1950 corresponds to $Man_6GlcNAc_2$. Panel 4: Same analytes as for panel 3, but after overnight treatment with 30 mU purified recombinant *T. reesei* α-1,2-mannosidase. Panel 5: N-glycans derived from recombinant haemagglutinin co-expressed in *Pichia pastoris* with mouse mannosidase IB-HDEL (under control of the GAP promotor). Panel 6: same analytes as for panel 5, but after overnight treatment with 30 mU purified recombinant *T. reesei* α-1,2-mannosidase.

As shown in FIG. 7, the *Trichoderma reesei* α-1,2-mannosidase provided the most complete reduction in the number of α-1,2-mannoses present on the N-glycans. The N-glycan processing by mouse mannosidase IB-HDEL was less efficient than by the *Trichoderma reesei* α-1,2-mannosidase.

Despite the efficient removal of α-1,2-mannoses from the N-glycans of haemagglutinin, no $Man_5GlcNAc_2$ was obtained. Even after digestion of the N-glycans with 3 mU of purified *Trichoderma reesei* α-1,2-mannosidase, only Man$_6$GlcNAc$_2$ was obtained as the smallest sugar chain. These results indicated that the remaining residues were possibly α-1,6-linked mannoses, originating from the initiating OCH1 α-1,6-mannosyltransferase enzymatic activities. OCH1 was observed to be localized to very early part of the Golgi apparatus and could act on the N-glycans of haemagglutinin before complete digestion of the Man$_8$GlcNAc$_2$ precursor to Man$_5$GlcNAc$_2$ by the mannosidases-HDEL. Thus, for proteins whose glycans are efficiently modified by the α-1,6-mannosyltransferase, an inactivation of the OCH1 gene coding for the transferase would be desirable in order to obtain proteins with Man$_5$GlcNAc$_2$.

EXAMPLE 3

Inactivation of the Pichia Och1 Gene

A *Pichia pastoris* sequence was found in the GenBank under Accession No. E12456 and was described in Japanese Patent Application No. 07145005, incorporated herein by reference. This sequence shows all typical features of an α-1,6-mannosyltransferase and is most homologous to the *S. cerevisiae* OCH1, thus referred to herein as the *Pichia pastoris* Och1 gene.

Figure 8:
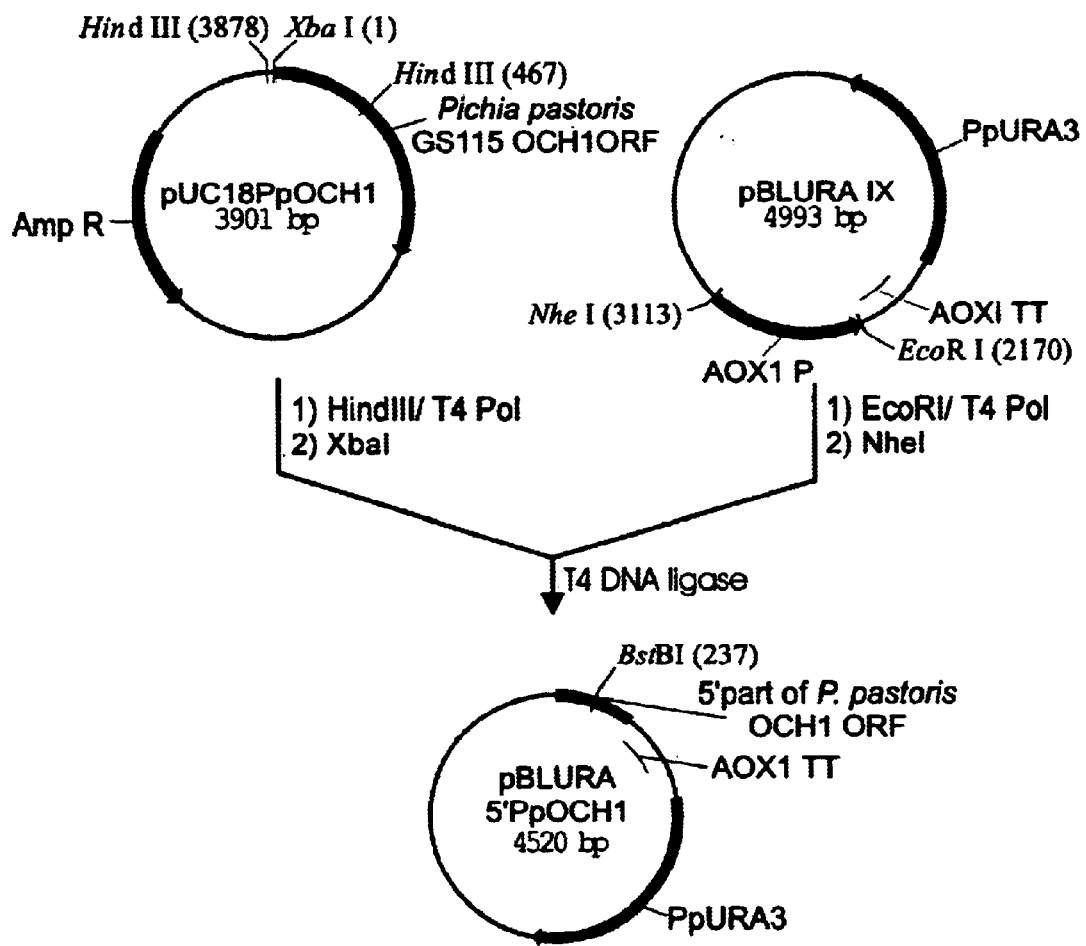
FIG. 8 graphically depicts vector pBLURA5'PpOCH1 and the way in which it was constructed.

First, the full ORF of the *Pichia pastoris* Och1 gene was PCR cloned in pUC18 to obtain plasmid pUC18pOch1. pUC18pOch1 was cut with HindIII, blunt-ended with T4 polymerase, then cut with XbaI, releasing a fragment containing the 5' part of the *Pichia pastoris* OCH1 gene. This fragment was ligated into the vector pBLURA IX (available from the Keck Graduate Institute, Dr. James Cregg, which had been cut with Eco RI, blunt-ended with T4 polymerase, and then cut with Nhe I. This ligation generated pBLURA5'PpPCH1, as shown in FIG. 8.

Figure 9:
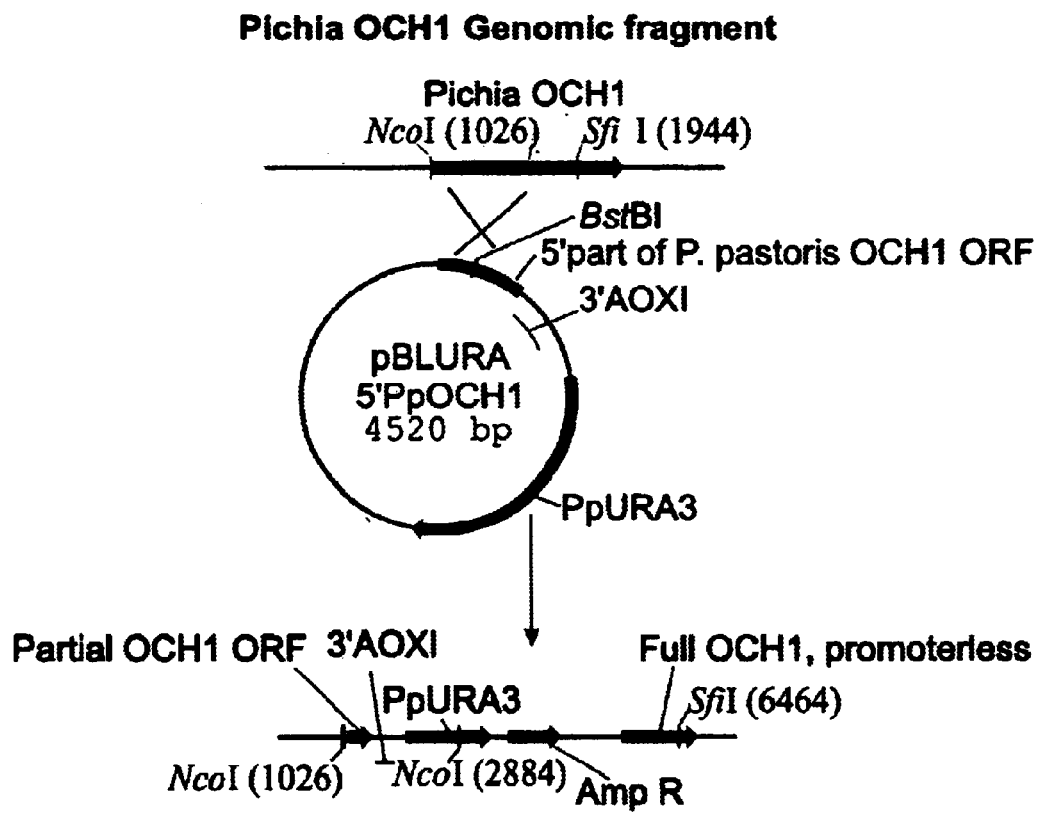
FIG. 9 depicts the scheme for disrupting the *Pichia pastoris* OCH1 gene by single homologous recombination using pBLURA5'PpOCH1.

Disruption of this Pichia OCH1 gene in the Pichia genome was achieved by single homologous recombination using pBLURA5'PpOCH1, as illustrated in FIG. 9. As a result of the single homologous recombination, the Och1 gene on the Pichia chromosome was replaced with two Och1 sequences: one consisted only about the first one third of the full Och1 ORF, the other had a full Och1 ORF without a Och1 promoter. Single homologous recombination was achieved as follows. Cells of the Pichia strain yGC4 were transformed by electroporation with pBLURA5'PpOCH1 which had been linearized with the single cutter Bst BI. About 500 transformants were obtained on minimal medium containing 1M sorbitol, biotin, arginine, adenine and histidine and incubation at 27° C. Thirty-two of these transformants were picked and re-selected under the same conditions. Twelve clones were further analyzed for correct genomic integration of the cassette by PCR. Seven of the twelve URA prototrophic clones contained the cassette in the correct locus.

Figure 10:
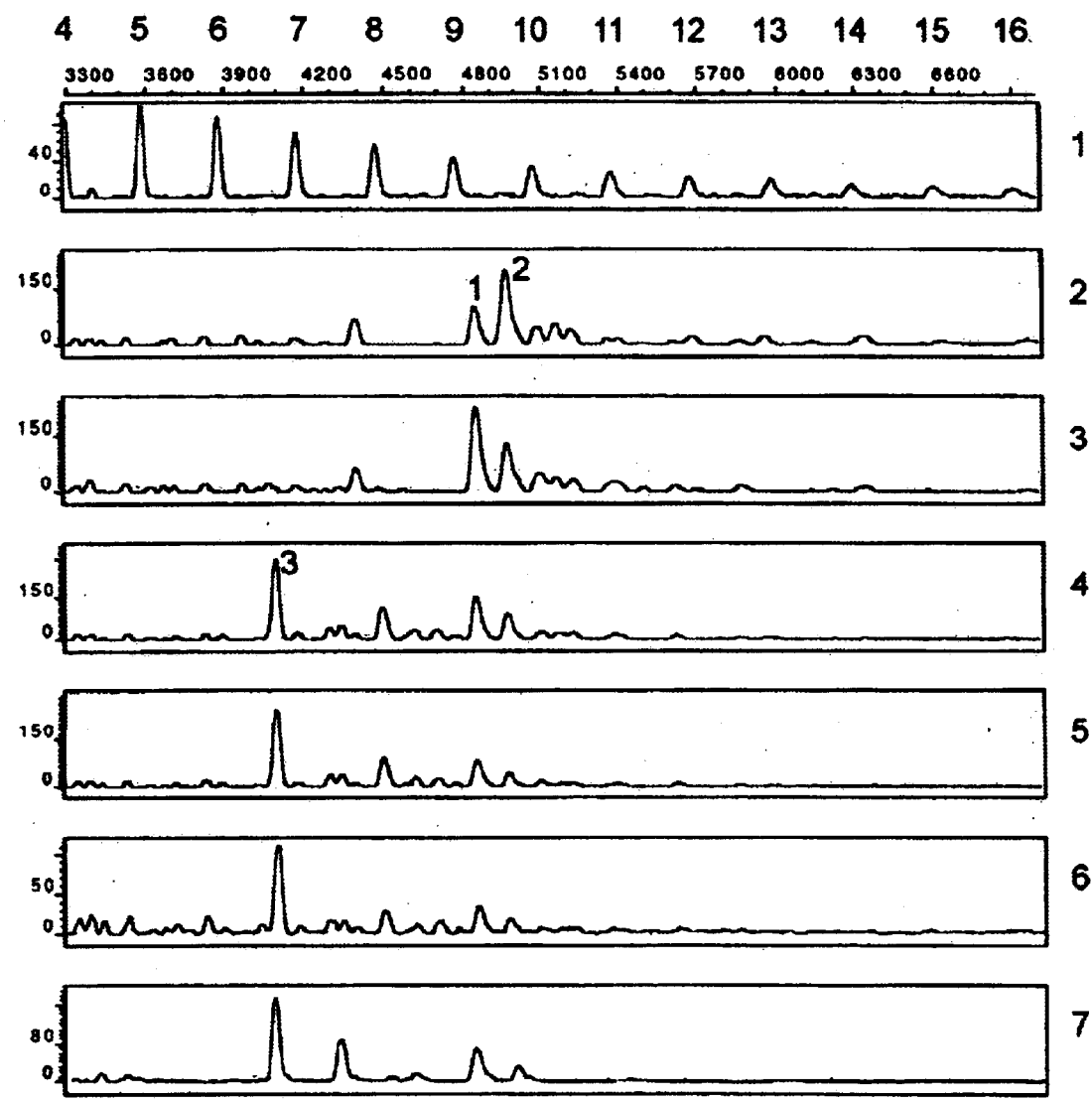
FIG. 10 depicts the cell wall glycoprotein N-glycan analysis of the Och1-inactivated clone and three clones derived from this Och1-inactivated clone by transformation with pGAPZMFManHDEL. Panel 1 shows the analysis of a mixture of malto-oligosaccharides, the degree of polymerisation of which is given by the numbers on the very top of the figure. This analysis serves as a size reference for the other panels. On the vertical axis of all panels, peak intensity in relative fluorescence units is given. Panel 2–6: analysis of the cell wall glycoprotein N-glycans of the following strains: Panel 2, non-engineered *P. pastoris* strain yGC4; Panel 3, yGC4 transformed with pBLURA5'PpOch1; 4–6, three clones of the strain of Panel 3, supplementarily transformed with pGAPZMFManHDEL. Panel 7: the N-glycans derived from bovine RNaseB, consisting of a mixture of $Man_{5-9}GlcNAc_2$. As can be seen from comparison between panel 2 and 3 and reference to panel 7, transformation with pBLURA5'PpOch1 leads to a strongly increased abundance of the $Man_8GlcNAc_2$ substrate N-glycan (named peak 1 in Panel 2) of OCH1p. Peak 2 represents the $Man_9GlcNAc_2$ product of OCH1p. Furthermore, upon supplementary transformation of pGAPZMFManHDEL, the major glycan on the cell wall glycoproteins of three independent clones is the $Man_5GlcNAc_2$ end product (peak 3 in panel 4) of *T. reesei* α-1,2-mannosidase digestion of the $Man_8GlcNAc_2$ substrate.
Figure 11:
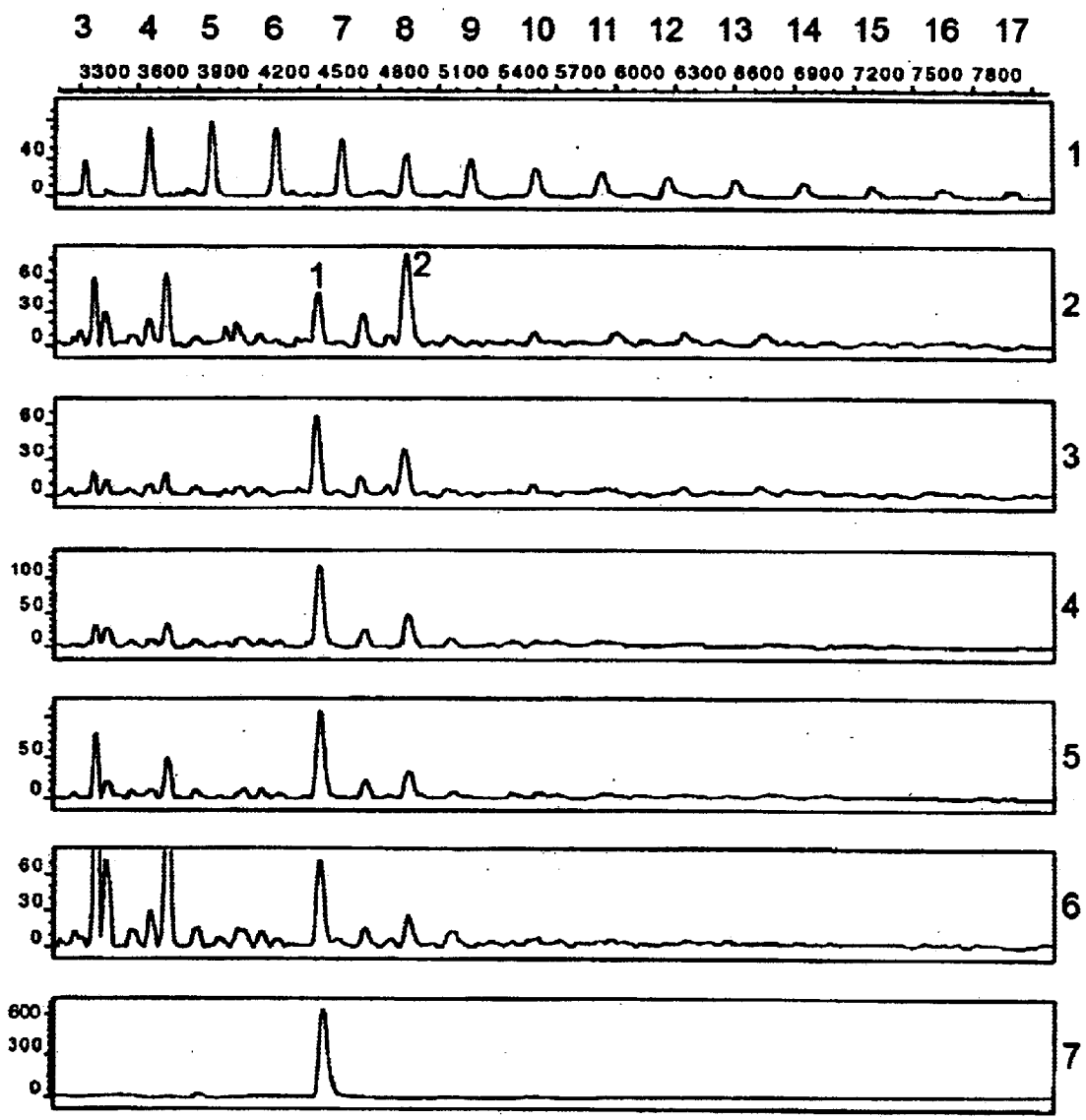
FIG. 11 depicts the analysis of exactly the same glycan mixtures as in FIG. 10, but after an in vitro digest with 3 mU/ml purified *Trichoderma reesei* α-1,2-mannosidase, overnight in 20 mM sodium acetate pH=5.0. Axis assignment is the same as in FIG. 10. More $Man_5GlcNAc_2$ is formed in the pBLURA5'PpOch1 transformed strain (Panel 3) than in the parent strain (Panel 2). Peaks in all panels before scan 3900 come from contaminants and should be ignored in the analysis.
Figure 12:
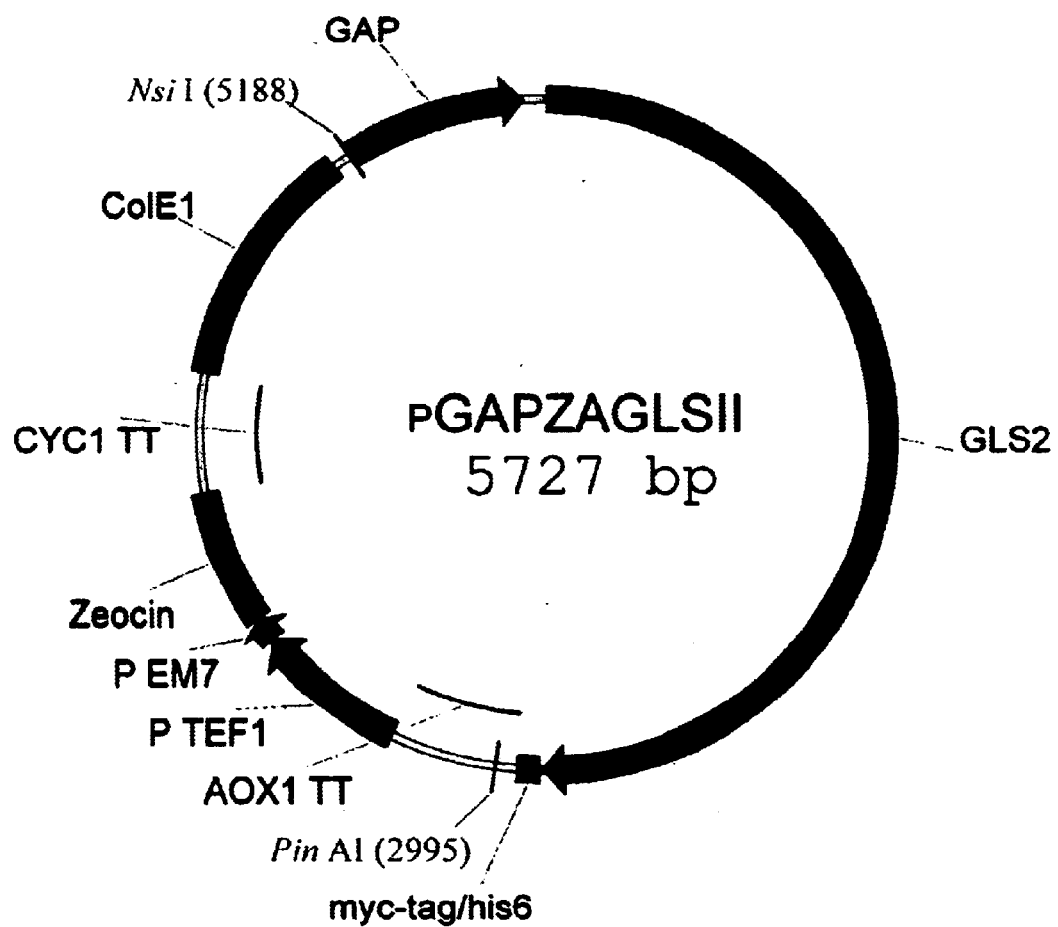
FIG. 12 depicts the expression vector pGAPZAGLSII (SEQ ID NO: 18). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Co1 E1: bacterial origin of replication. GAP: promotor of the *P. pasttoris* GAP gene. GLS2: *S. cerevisiae* glucosidase II gene. AOX1 TT: transcription terminator of the *P. pastoris* AOX1 gene
Figure 13:
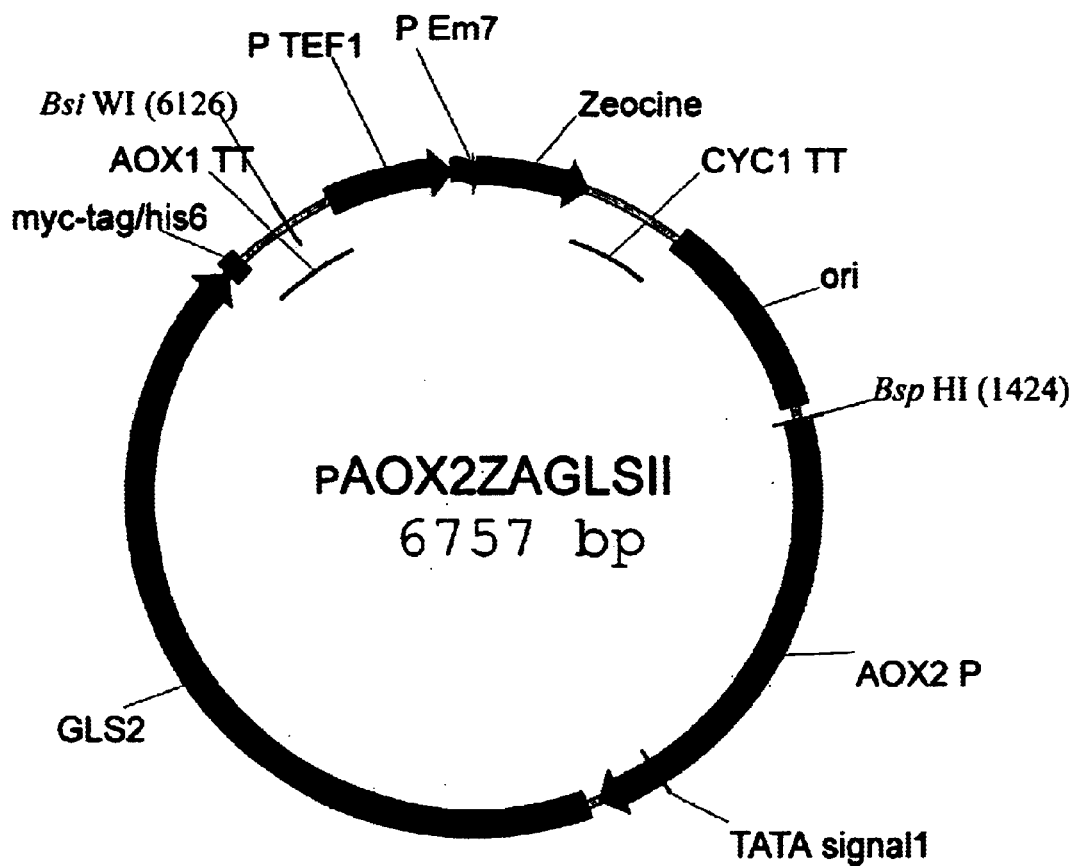
FIG. 13 depicts the expression vector pAOX2ZAGLSII (SEQ ID NO: 16). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Co1 E1: bacterial origin of replication. AOX2 P: promotor of the *P. pastoris* AOX2 gene. GLS2: *S. cerevisiae* glucosidase II gene. AOX1 TT: transcription terminator of the *P. pastoris* AOX1 gene
Figure 14:
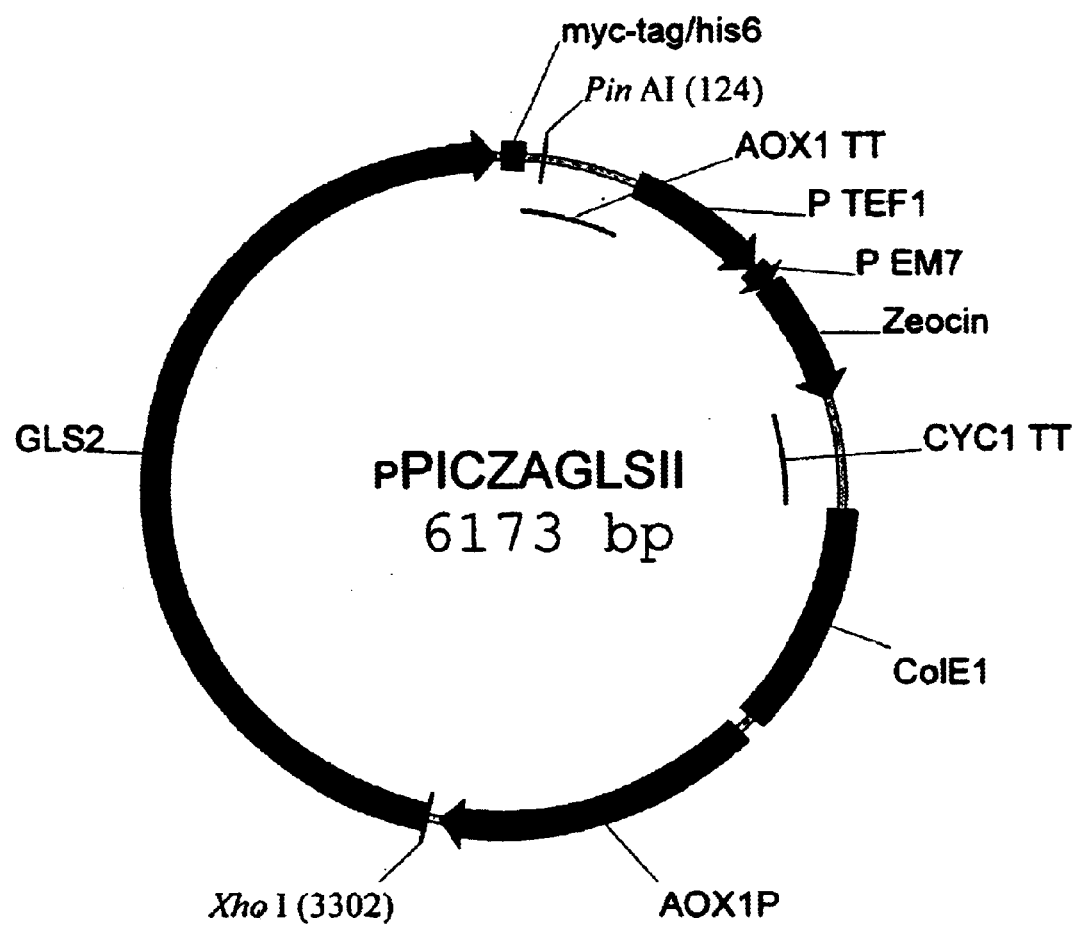
FIG. 14 depicts the expression vector pPICZAGLSII (SEQ ID NO: 20). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Co1 E1: origin of replication. AOX1 P: promotor of the *P. pastoris* AOX1 gene. GLS2: *S. cerevisiae* glucosidase II gene. AOX1 TT: transcription terminator of the *P. pastoris* AOX1 gene
Figure 15:
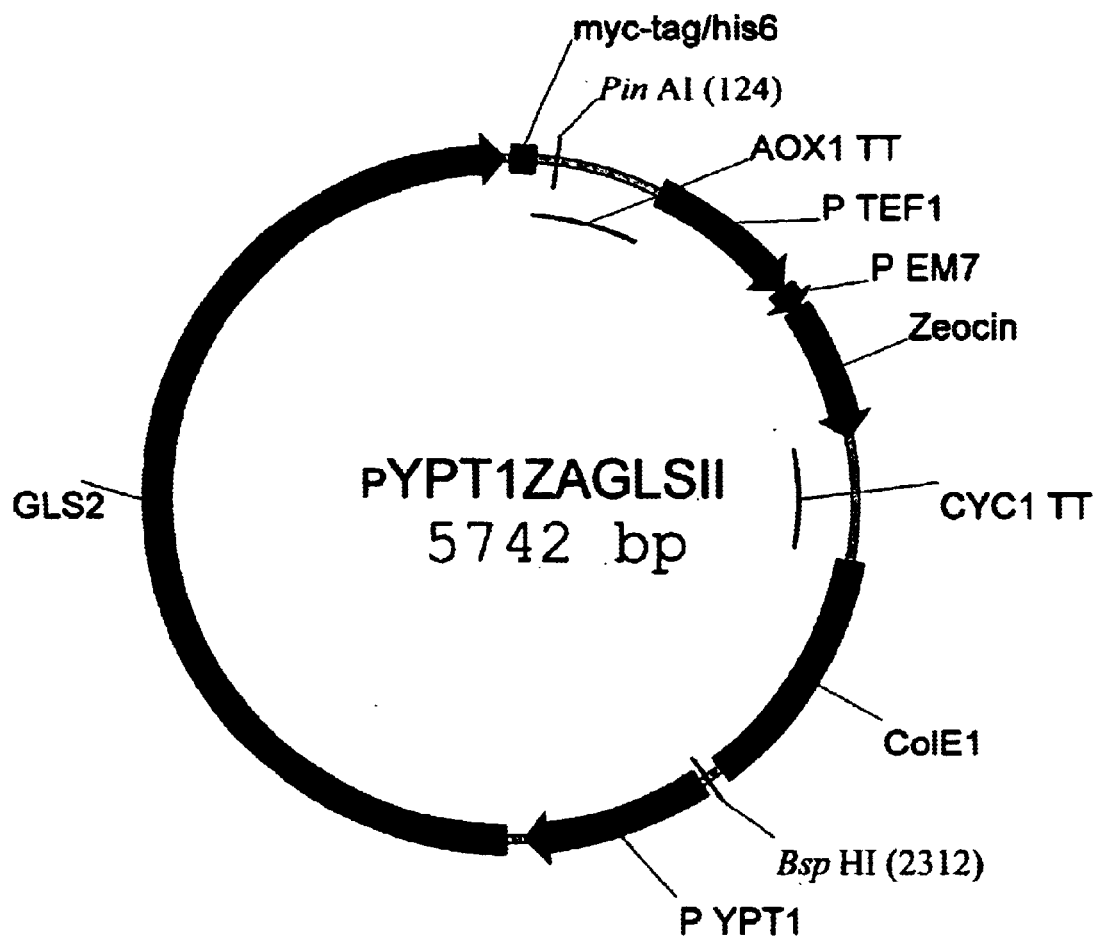
FIG. 15 depicts the expression vector pYPT1ZAGLSII ((SEQ ID NO: 22). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Co1 E1: origin of replication. P YPT1: promotor of the *P. pastoris* YPT1 gene. GLS2: *S. cerevisiae* glucosidase II gene. AOX1 TT: transcription terminator of the *P. pastoris* AOX1 gene.
Figure 16:
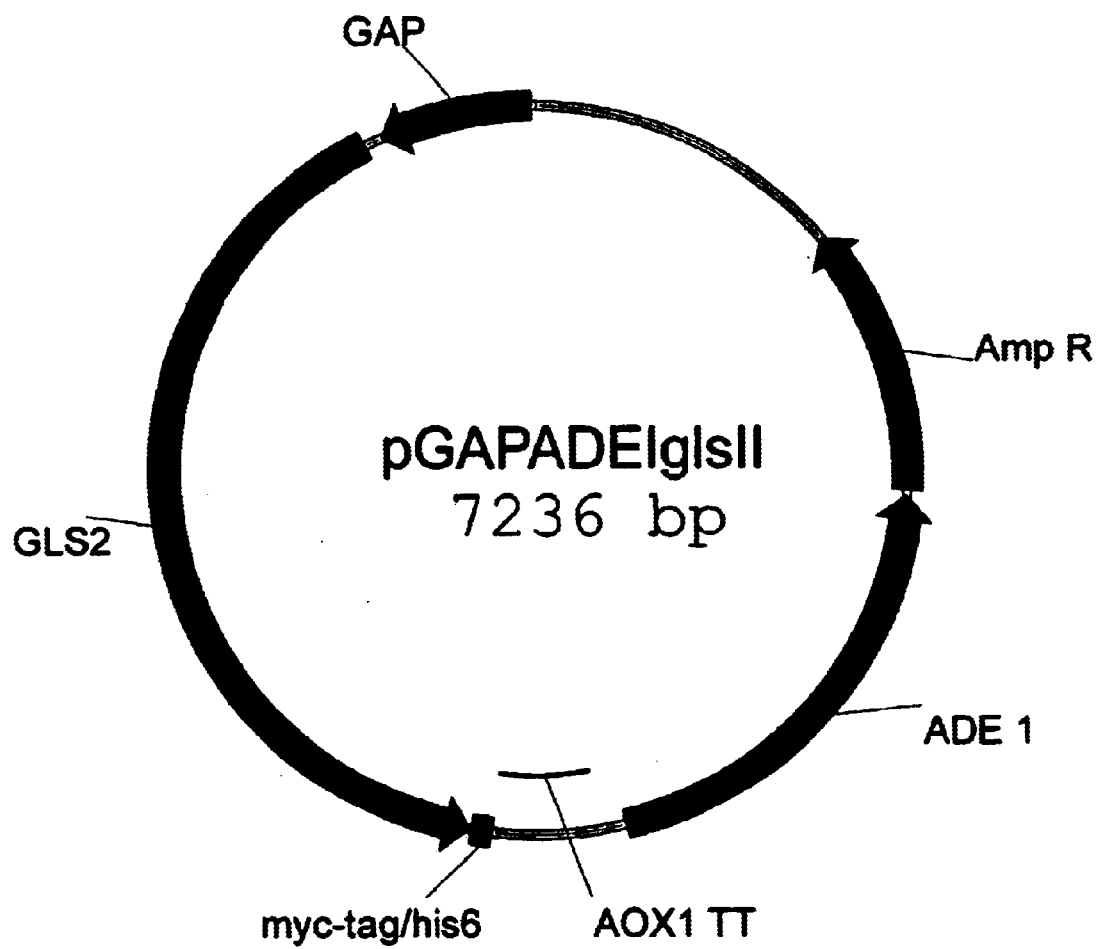
FIG. 16 depicts the expression vector pGAPADE1glsII (SEQ ID NO: 19). Amp R: Ampillicin resistance marker gene. ADE1: *P. pastoris* ADE1 selection marker gene. GAP: promotor of the *P. pastoris* GAP gene. GLS2: *S. cerevisiae* glucosidase II gene. AOX1 TT: transcription terminator of the *P. pastoris* AOX1 gene
Figure 17:
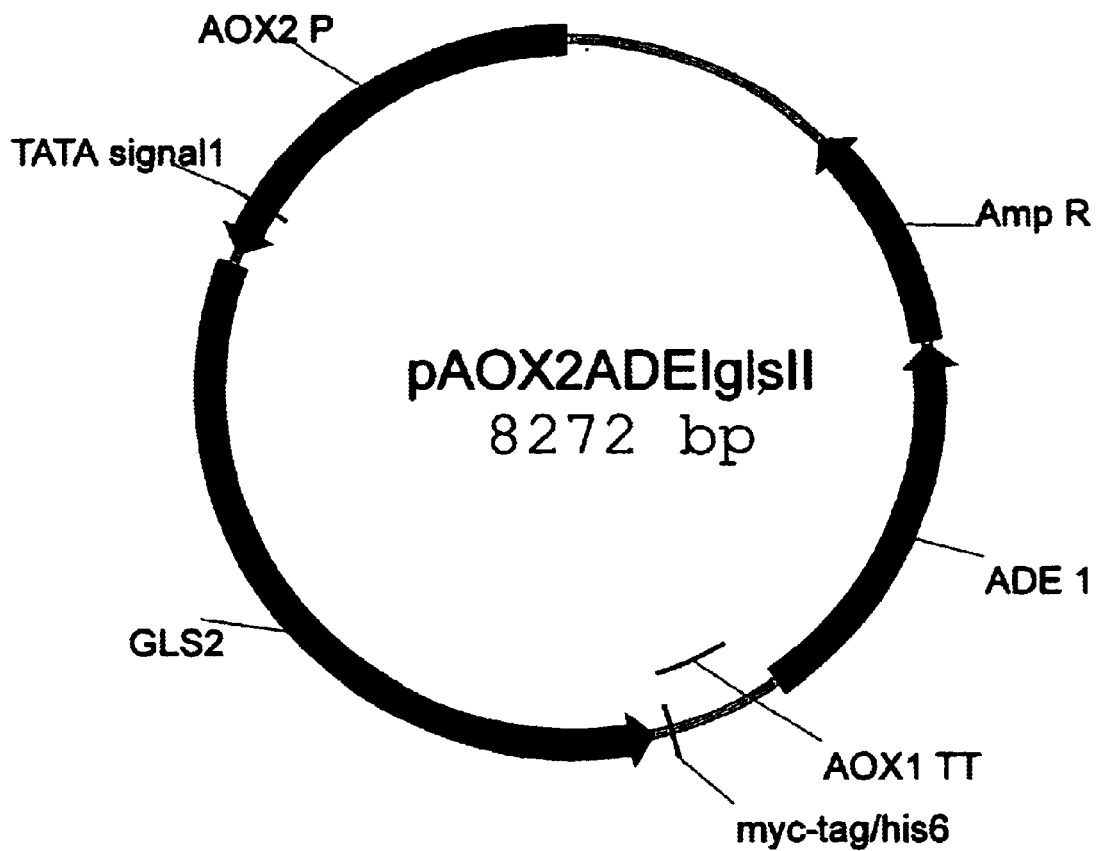
FIG. 17 depicts the expression vector pAOX2ADE1glsII (SEQ ID NO: 17). Amp R: Ampillicin resistance marker gene. ADE1: *P. pastoris* ADE1 selection marker gene. AOX2 P: promotor of the *P. pastoris* AOX2 gene. GLS2: *S. cerevisiae* glucosidase II gene. AOX1 TT: transcription terminator of the *P. pastoris* AOX1 gene.
Figure 18:
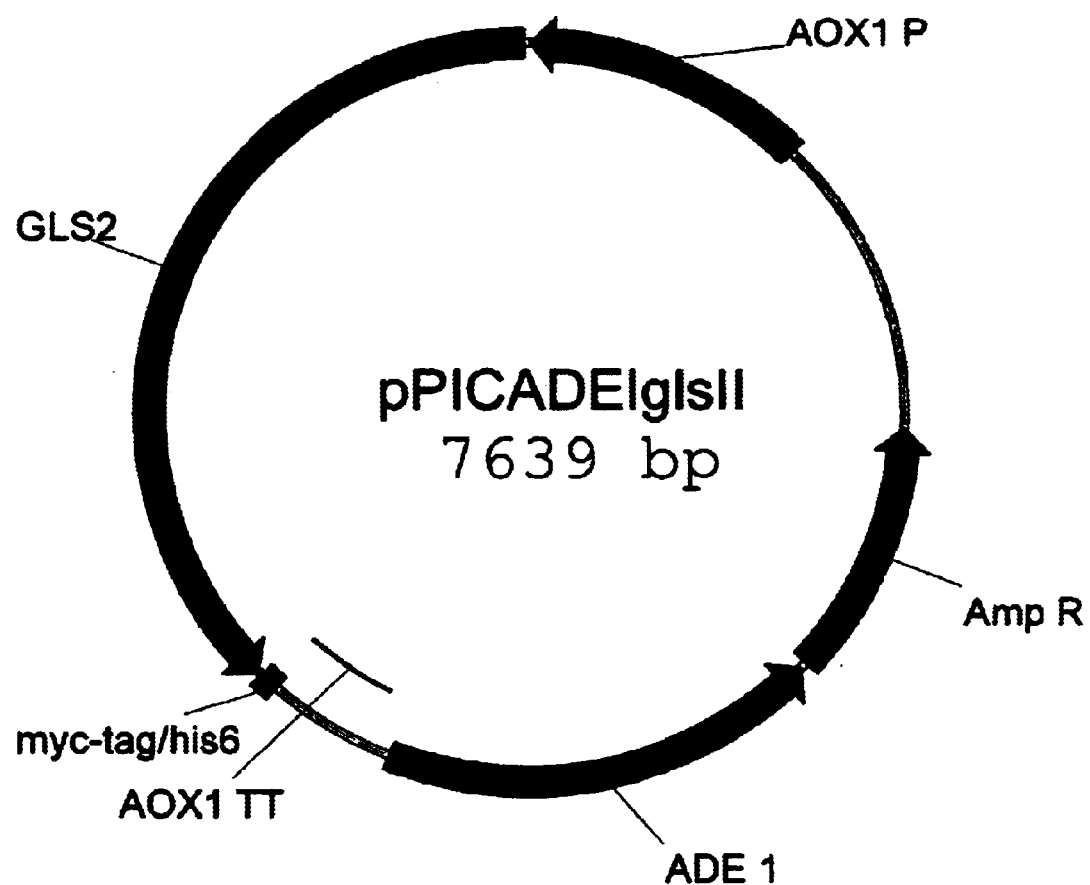
FIG. 18 depicts the expression vector pPICADE1glsII (SEQ ID NO: 21). Amp R: Ampillicin resistance marker gene. ADE1: *P. pastoris* ADE1 selection marker gene. AOX1 P: promotor of the *P. pastoris* AOX1 gene. GLS2: *S. cerevisiae* glucosidase II gene. AOX1 TT: transcription terminator of the *P. pastoris* AOX1 gene.
Figure 19:
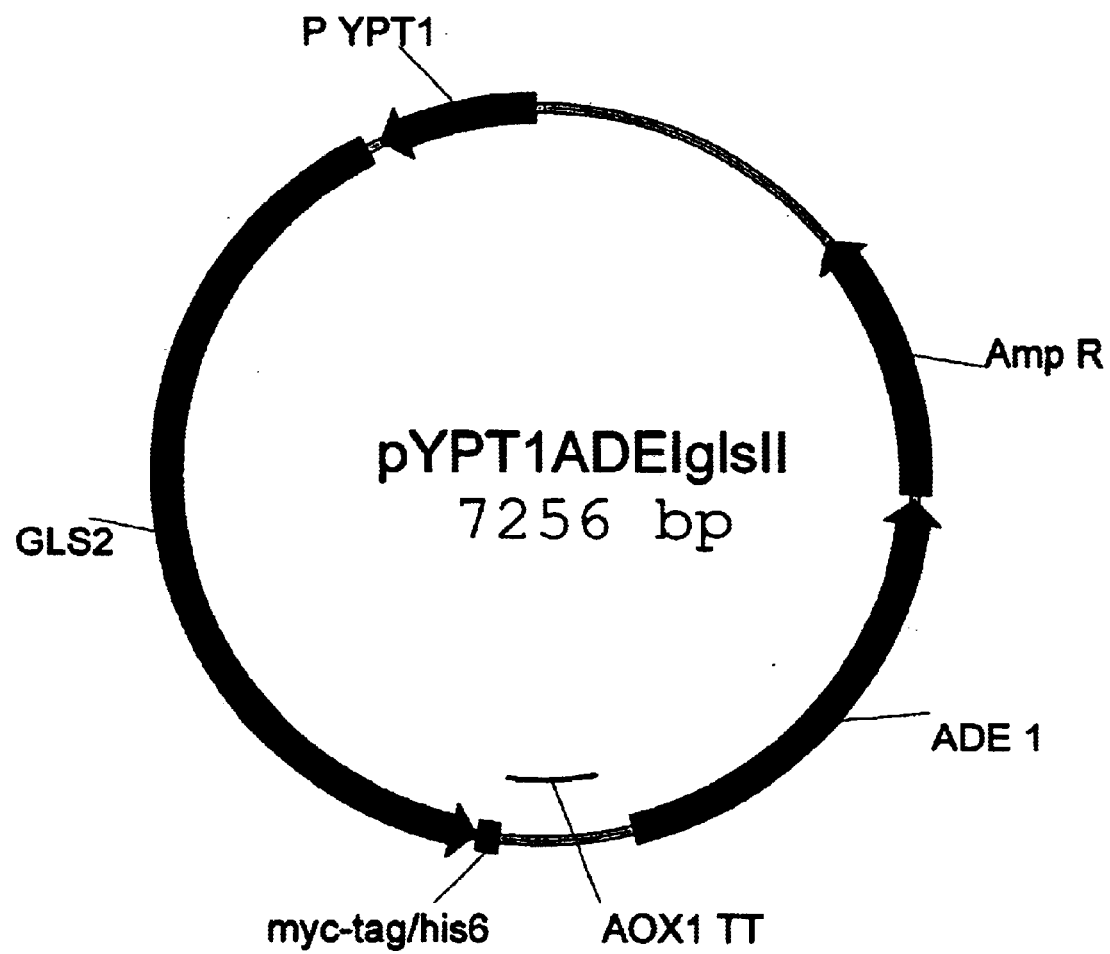
FIG. 19 depicts the expression vector pYPT1ADE1glsII (SEQ ID NO: 23). Amp R: Ampillicin resistance marker gene. ADE1:*P. pastoris* ADE1 selection marker gene. P YPT1: promotor of the *P. pastoris* YPT1 gene. GLS2: *S. cerevisiae* glucosidase II gene. AOX1 TT: transcription terminator of the *P. pastoris* AOX1 gene.

One of the OCH1-inactivated clones was also further transformed with pGAPZMFManHDEL to produce "supertransformants". Both the Och1-inactivated clone and three supertransformants also expressing the ManHDEL were evaluated in cell wall glycan analysis as follows. Yeast cells were grown in 10 ml YPD to an OD$_{600}$=2 and mannoproteins were prepared by autoclaving the yeast cells in 20 mM sodium citrate buffer pH7 for 90 min at 120° C. and recovery of the supernatant after centrifugation. Proteins were precipitated from this supernatant with 3 volumes of cold methanol. The protein preparation obtained in this way was used for N-glycan analysis using DSA-FACE as described by Callewaert et al. (2001) *Glycobiology* 11, 275–281. As shown in FIG. 10, there was an increased amount of Man8GlcNAc$_2$ glycan in the Och1-inactivanted clone as compared to parent strain yGC4, indicative of a reduced activity of the Och1 enzyme. In all three supertransformants which also expressed the HDEL (SEQ ID NO: 1)-tagged α-1,2 mannosidase, the production of Man$_5$GlcNAc$_2$ was observed. Furthermore, upon digestion of the same glycan mixtures with 3 mU/ml purified recombinant *Trichoderma reesei* α-1,2-mannosidase, more Man$_5$GlcNAc$_2$ was formed in the strain transformed with pBLURA5'PpOCH1 than in the parent strain (FIG. 11, compare panel 2 and 3).

These results confirmed that the lack of a production of Man$_5$ glycans on recombinantly produced proteins such as haemagglutinin from cells expressing α-1,2-mannosidase were due to the activity of the Och1 protein. These results further indicate that the production of glycoproteins with Man$_5$ glycans could be facilitated by the inactivation of the Och1 gene.

EXAMPLE 4

Expression of Glucosidase II in *Pichia pastoris*

4.1 Amplification of the GLSII Alpha Subunit ORF from *S. cerevisiae*.

Genomic DNA was prepared from the *S. cerevisiae* strain INVS (α, leu2-3, 112 his3Δ1, trp1-289, ura3-52), using the Nucleon kit (Amersham). A touch-down PCR reaction was performed using this genomic DNA as template and the LA TaKaRa polymerase (ImTec Diagnostics). The sequence of the PCR primers was based on the known sequence of the *S. cerevisiae* GLSII ORF:

```
Sense primer:     5' CCG CTC GAG ATG GTC CTT TTG AAA TGG CTC 3'   (SEQ ID NO:12)
                          Xho I Antisense primer: 5' CCG GGC CCA AAA ATA ACT TCC CAA TCT TCA G 3' (SEQ ID NO:13)
                         Apa I
```

4.2 Cloning of the *S. cerevisiae* glucosidase II ORF into *Pichia pastoris* Expression Vectors Construction of the glucosidase II expression vectors— The PCR fragment was digested with Xho I/Apa I and ligated into the pGAPZA vector (Invitrogen), thereby placing the ORF under the transcriptional control of the GAP promoter. Using this strategy, the myc and the His6 tag were placed in frame to the C-terminus of Glucosidase II, creating pGAPZAGLSII. The complete ORF of pGAPZAGLSII was then sequenced to ensure that no mutations were generated in the PCR reaction. The sequence of the vector pGAPZA-GLSII was set forth in SEQ ID NO: 18. The GLSII ORF from the pGAPZAGLSII vector was cloned into vector pPICZA (Invitrogen) to create pPICZAGLSII, thereby placing the ORF under the transcriptional control of the AOXI promoter. The GLSII ORF from the pGAPZAGLSII vector was cloned into vector pAOX2ZA, thereby placing the ORF under the transcriptional control of the AOX2 promoter. This vector was created by replacing the multi cloning site of vector pAOX2ZB with the multi cloning site of pPICZA. Vector pAOX2ZB was generated by replacing the AOX1 promotor of pPICZB by the AOX2 promotor region of the AOX2 gene (Martinet et al., Biotechnology Letters 21). The AOX2 promotor region was generated by PCR on Pichia genomic DNA with the sense primer 5'GAC-GAGATCTTTTTTTCAGACCATATGACCGG 3' (SEQ ID NO: 26) and the antisense primer 5'GCGGAATTCTTTTCT-CAGTTGATTTGTTTGT 3' (SEQ ID NO: 27). The GLSII ORF from the pGAPZGLSII vector was cloned into vector pYPT1ZA to create pYPT1ZAGLSII, thereby placing the ORF under the transcriptional control of the YPT1 promoter. Vector pYPTZA was created by replacing the AOX1 promoter of pPICZA by the YPT1 promoter present on the plasmid pIB3 (GenBank accession number AF027960) (Sears et al., Yeast 14, pg 783–790, 1998). All constructs contain the phleomycin resistance gene. The resulting final expression vectors (pGAPZAGLSII, pAOX2ZAGLSII, pPICZAGLSII and pYPT1ZAGLSII) are depicted in FIGS. 12–15.

Similar expression vectors were constructed, carrying the Ampicillin resistance marker and the Pichia ADE1 selection marker. In principle, the Zeocin resistance expression cassette of the plasmids pAOX2ZAGLSII, pGAPZAGLSII and pYPT1ZAGLSII was replaced by the Ampicillin and Pichia ADE1 cassette of the vector pBLADE IX (Cregg, J. M.) to result in the vectors pAOX2ADE1 glsII, pGAPADE1glsII and pYPT1ADE1glsII. Vector pPICADE1glsII was obtained by inserting the glucosidase II open reading frame into the multiple cloning site of the vector pBLADE IX (Cregg, J. M.). The resulting final expression vectors (pGAPADE1glsII, pAOX2ADE1glsII, pPICADE1glsII and pYPT1ADE1glsII) are depicted in FIGS. 16–20.

Adding the ER retention tag HDEL (SEQ ID NO: 1) to Glucosidase II expression vectors—The following primers were used to generate an HDEL (SEQ ID NO: 1)-containing PCR fragment:

```
Primer 1: 5'GCG GGT CGA C/CA C/GA C/GA A/CT G/TG A/GT TTT AGC CTT(SEQ ID NO:28)
              Sal I    H   D   E   L    stop
          AGA CAT GAC 3'

Primer 2: 5'CAG GAG CAAA GCT CGT ACG AG 3'              (SEQ ID NO:29)
                          Spl I
```

Figure 20:
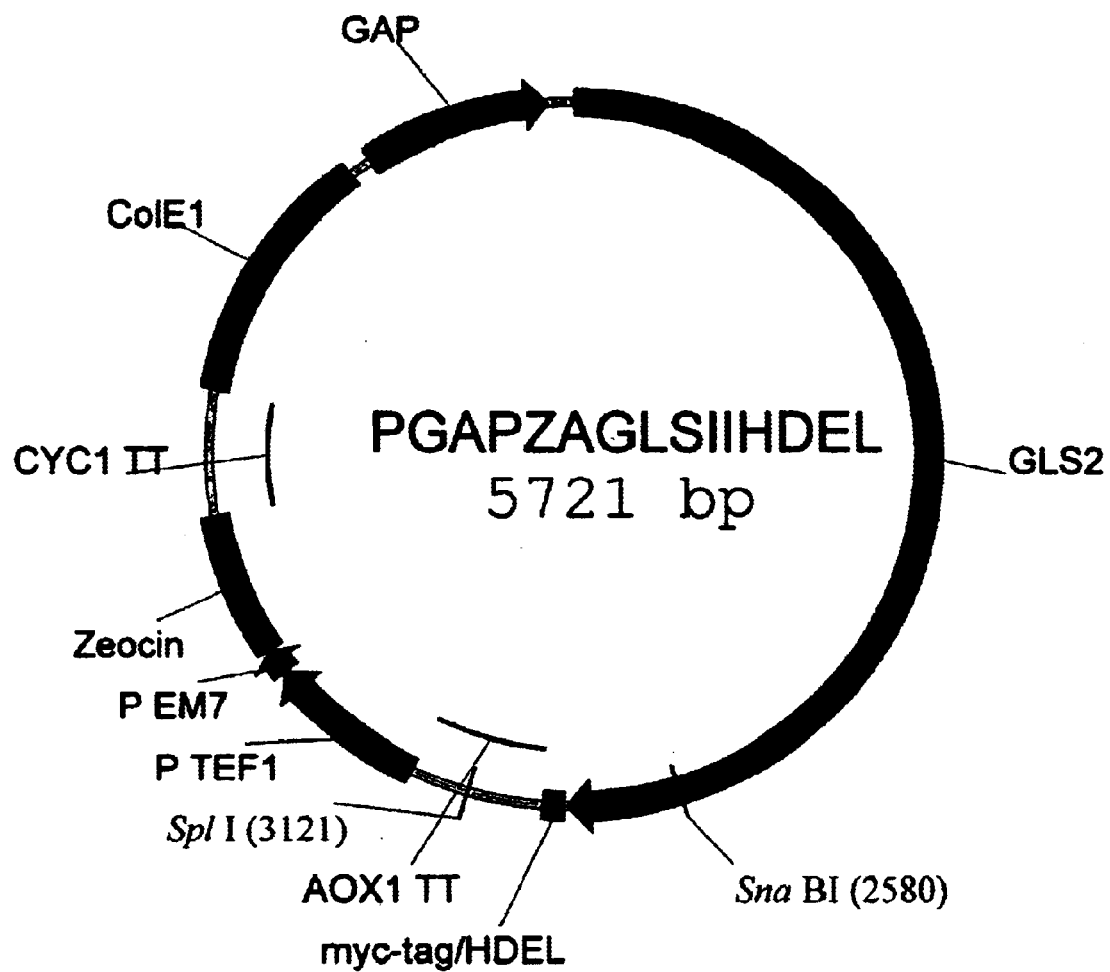
FIG. 20 depicts the expression vector pGAPZAglsIIHDEL (SEQ ID NO: 24). Amp R: Ampillicin resistance marker gene. ADE1: *P. pastoris* ADE1 selection marker gene. GAP: promotor of the *P. pastoris* GAP gene. GLS2: *S. cerevisiae* glucosidase II gene. AOX1 TT: transcription terminator of the *P. pastoris* AOX1 gene.
Figure 21:
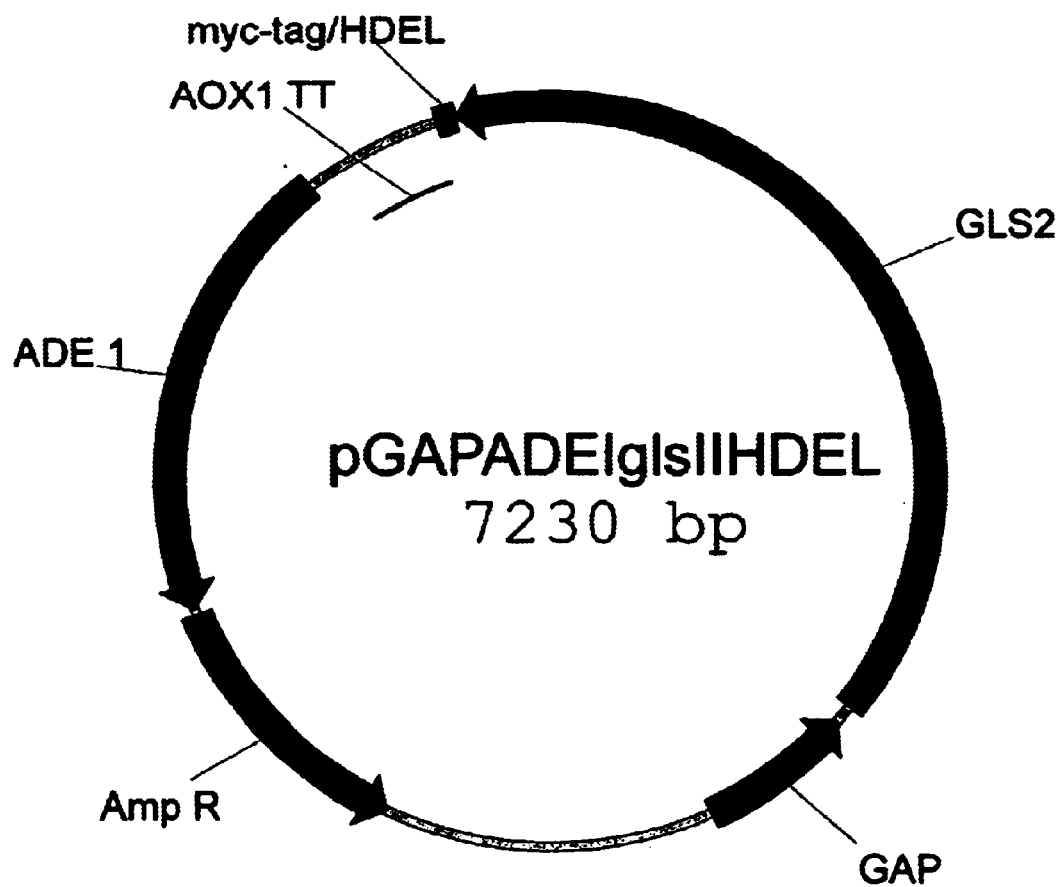
FIG. 21 depicts the expression vector pGAPADE1glsIIHDEL (SEQ ID NO: 25). P TEF1: promotor of *S. cerevisiae* transcription elongation factor gene. P Em7: synthetic prokaryotic promotor. Zeocin: zeocine resistance marker gene. CYC1 TT: transcription terminator of *S. cerevisiae* cytochrome C1 gene. Co1 E1: bacterial origin of replication. GAP: promotor of the *P. pastoris* GAP gene. GLS2: *S. cerevisiae* glucosidase II gene. AOX1 TT: transcription terminator of the *P. pastoris* AOX1 gene.

PCR was performed on pGAPZAGLSII with Taq pol., at 60° C. The PCR fragment of 225 bp was cut with Sal I/Spl I and ligated into the Sal I/Spl I opened pGAPZAGLSII vector, creating plasmid pGAPZAglsIIHDEL. The sequence of plasmid pGAPZAglsIIHDEL is set forth in SEQ ID NO: 24. The construction strategy and the resulting final expression vectors (pGAPZAglsIIHDEL and pGAPADE1glsIIHDEL) are depicted in FIGS. 20–21.

4.3 Transformation of a *Pichia pastoris* Strain

Transformation was performed using the conventional electroporation techniques, as described by Invitrogen. Cells of the *Pichia pastoris* strain PPY12-OH were transformed with pGAPZGLSII which had been cut with the single cutter Avr II. Transformants were selected based on their resistance to zeocin.

Genomic analysis of the transformants—Genomic DNA was prepared from some zeocin resistant Pichia transformants. A PCR reaction was performed on the genomic DNA in order to determine whether or not the glucosidase II gene was integrated into the yeast genome. PCR was performed using Taq DNA polymerase (Boehinger) (2.5 mM MgCl$_2$, 55° C. for annealing). The primers were the same as the ones we used for the amplification of the ORF on *S. cerevisiae* genomic DNA. pGAPZAGLSII transformants were confirmed by the presence of a specific PCR product indicative of the glucosidase II ORF.

4.4 Expression and Secretion of the *S. cerevisiae* Glucosidase II Alpha Subunit in *Pichia pastoris*

Analysis at the transcriptional level—RNA was prepared from the transformants which scored positive after the genomic analysis. RNA was prepared using acid phenol. From each sample, 15 µg of RNA was loaded on a formaldehyde agarose gel. After electrophoresis the RNA was blotted on a Hybond N membrane. The membrane was hybridizing using a radioactive probe, which consists of a 344 bp glucosidase II specific fragment, corresponding to the 3' region of the glucosidase II ORF. No signals were detected with non-transformed control strains, whereas clear signals were observed with transformants.

Analysis at the protein level using a double membrane assay—A nitrocellulose membrane was placed on a buffered dextrose medium (BMDY). On top of that nitrocellulose membrane, a cellulose acetate membrane was placed. Pichia transformants of pGAPZAGLSII were streaked on the cellulose acetate and grown for a few days. The yeast cells remained on the cellulose acetate, while the secreted proteins crossed this membrane. As such the secreted protein was captured onto the nitrocellulose membrane. After a few days the cellulose acetate, containing the yeast colonies, was removed. The nitrocellulose membrane was analyzed for the presence of glucosidase II using anti-myc antibody. Most of the transformants gave a clear signal as compared to a faint, hardly visible signal with the WT, non-transformed strain.

Extracellular expression—PPY12-OH transformants of the construct pGAPZAGLSII(mychis6) (strains 12, 14 and 18) and transformants of the construct pGAPZAGLSII(myc) HDEL (strains H1, H2 and H3) were grown for 2 days on 2×10 ml BMDY medium. These 6 transformants earlier scored positive both on the genomic level (PCR on gDNA) and on the RNA level (Northern blot). The culture medium was collected by centrifugation and concentrated with Vivaspin columns to about 1 ml. Proteins from this concentrate were precipitated with TCA, resuspended in Laemmli buffer and loaded for SDS-PAGE analysis. Proteins were blotted to nitrocellulose membrane. The blot was incubated overnight with anti-myc Ab. The secondary Ab was linked to peroxidase. Using the Renaissance luminiscence detection kit (NEN) and a light sensitive film (Kodak), a strong band at about 110 kDa was observed for the transformants 12, 14 and 18, indicating that GLSII was expressed and secreted from these transformants. No signal was obtained for the transformants H1-3, which indicate that the HDEL (SEQ ID NO: 1) tag, which was added C-terminally to the GLSII ORF, resulted in an ER localization of the protein, preventing GLSII to be secreted into the growth medium.

Intracellular expression—The 6 transformants and the WT strain were grown for 2 days in 500 ml BMDY. The cells were collected by centrifugation, washed, resuspended into a minimal volume (50 mM Tris.HCl pH 7.5, 5% glycerol) and broken using glass beads. The cell debris was removed through several centrifugation steps (low speed centrifugation (2000–3000 g)). Membranes were obtained from the supernatant through ultracentrifugation. The pellets were resuspended in Laemmli buffer and loaded for SDS-PAGE analysis. The proteins were blotted on a nitrocellulose membrane. The intracellular GLSII expression was checked using anti-myc Ab and peroxidase conjugated secondary Ab. Following the luminescence detection, a band at about 110 kDA was observed with the GLSIIHDEL tranformants (H1 and H3, faint signal for H2), but not with the WT and GLSII expression strains. These results clearly indicate the intracellular presence of the recombinant GLSII when expressed with a C-terminal HDEL (SEQ ID NO: 1) tag. No GLSII was detected intracellularly when this tag was not present.

4.5 Purification and Activity Assays of the Recombinant Glucosidase II Alpha Submit A GLSII assay was set up as follows and was tested using a commercially available yeast alpha-glucosidase (Sigma) as a positive control.

Figure 22:
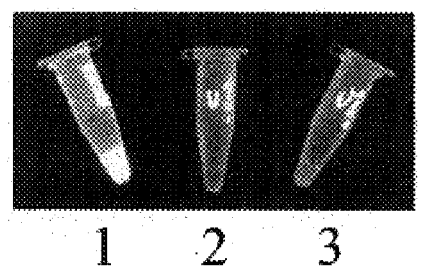
FIG. 22 depicts the test of the GLSII activity assay using a commercially available yeast alpha-glucosidase (Sigma: Cat. No. G-5003). The assay mixture contains phosphate-citrate buffer pH 6.8, mannose, 2-deoxy-D-glucose, the substrate 4-methylumbellyferyl-alpha-D-glucopyranoside and alpha-glucosidase from Sigma. 1: assay mixture illuminated with UV-light after overnight incubation at 37° C.; 2: same as 1, but this time, the assay mixture lacks the alpha-glucosidase; 3: same as 1, but this time, the assay mixture lacks the substrate.

Composition: 70 µl 80 mM phosphate-citrate buffer pH 6.8, 7 µl 250 mM mannose, 3.5 µl 250 mM 2-deoxy-D-glucose, 0.8 µl 4-MeUmbelliferyl-alpha-D-glucopyranoside (1 µM). Three assays were performed: one with 1 unit commercial enzyme, one without the enzyme and one with the enzyme but without the substrate. The assay mixture was incubated overnight at 30° C. When illuminated with UV, only the reaction mixture with both the enzyme and the substrate showed fluorescence (FIG. 22). This indicates that the assay was very specific in detecting the activity of the alpha-glucosidase.

Figure 23:
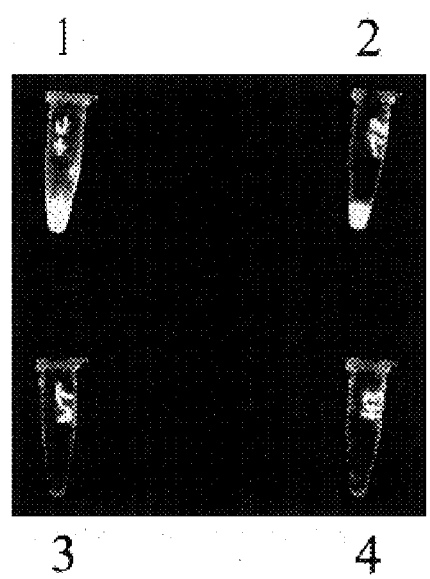
FIG. 23 depicts the results of the activity of recombinantly expressed GLSII from *Pichia pastoris*. All assay mixtures were incubated overnight at 37° C. and afterwards illuminated with UV-light. 1: assay with yeast alpha-glucosidase (Sigma: Cat. No. G-5003); 2: assay with the purified medium of strain 18 (PPY12-OH transformed with pGAPZAGLSII); 3: assay with purified medium of the WT PPY12-OH strain; 4: assay with the purified medium of strain H3 (PPY12-OH transformed with pGAPZAglsIIHDEL).

WT PPY12-OH, strain 18 and strain H3 were grown during 2 days in 2×10 ml growth medium. Cells were spun down and medium was adjusted to 300 mM NaCl and 10 mM imidazol and concentrated with Vivaspin columns to 0.5–1 ml. Medium was loaded onto a Ni-NTA spin column (Qiagen) and the purification was performed according to the manufactures recommendations. Protein was eluted from the column in 2×100 µl elution buffer (50 mM $NaH_2PO_4$, 300 mM NaCl, 250 mM imidazol pH 8.0). From each eluate, 20 µl was assayed for its glucosidase II activity. 0.33 units of the commercial enzyme diluted in 20 µl of the elution buffer was used as a positive control. Fluorescence was observed with the positive control and the elute of strain 18, the strain which secreted the enzyme into the growth medium. These results indicate that the recombinant S. cerevisiae GLSII alpha subunit, secreted by Pichia pastoris, was a functionally active enzyme. The activity was not seen in the WT (untransformed) strain, nor in strain H3 as the GLS II was expressed intracellularly (FIG. 23). These results also indicate that the beta subunit is not necessary for the functionality of the alpha part of the protein.

EXAMPLE 5

Creating Pichia Strains Expressing both Glucosidase II and Mannosidase

Strain GS115 was transformed with pGAPZGLSII and pGAPZglsIIHDEL. Transformants were selected on YPD-Szeo.

Strain yGC4 was transformed with the following constructs, respectively:

(1) pGAPADEglsII and pGAPADEglsIIHDEL, selection on synthetic sorbitol medium without adenine;

(2) pGAPZMFManHDEL: selection on YPDSzeo; and (3) pGAPZMFManHDEL/pGAPADEglsIIHDEL: selection on synthetic sorbitol medium without adenine and with zeocin.

Strain yGC4 with OCH1 knock-in and expressing MFmannosidaseHDEL was transformed with pGAPADEglsII and pGAPADEglsIIHDEL. Selection of transformants was done on synthetic sorbitol medium without adenine and uracil.

For all transformations, colonies were obtained. Transformants with the expression vector(s) integrated into the genome, determined by PCR, were obtained. Expression of GLSII from some of these transformants was observed.

---

We claim:

1. A genetically engineered methylotrophic yeast strain, wherein said strain is transformed with a vector capable of expressing an α-1,2-mannosidase or a functional part of said α-1,2-mannosidase in said methylotrophic yeast strain and a vector capable of expressing a glucosidase II or a functional part of said glucosidase II in said methylotrophic yeast strain, wherein said vector capable of expressing said α-1,2-mannosidase or said functional part of said α-1,2-mannosidase comprises a nucleotide sequence coding for said α-1,2-mannosidase or said functional part of said α-1,2-mannosidase, and said vector capable of expressing said glucosidase II or said functional part of said glucosidase II comprises a nucleotide sequence coding for said glucosidase II or said functional part of said glucosidase II.

2. A method of reducing glycosylation of a heterologous glycoprotein expressed from a methylotrophic yeast, comprising transforming cells of said methylotrophic yeast with a vector capable of expressing an α-1,2-mannosidase or a functional part of said α-1,2-mannosidase in said methylotrophic yeast, and with a vector capable of expressing a glucosidase II or a functional part of said glucosidase II in said methylotrophic yeast, wherein said vector capable of expressing said α-1,2-mannosidase or said functional part of said α-1,2-mannosidase comprises a nucleotide sequence coding for said α-1,2-mannosidase or said functional part of said α-1,2-mannosidase, and said vector capable of expressing said glucosidase II or said functional part of said glucosidase II comprises a nucleotide sequence coding for said glucosidase II or said functional part of said glucosidase II; and thereby reducing glycosylation of said heterologous glycoprotein.

3. A method of producing a glycoprotein with reduced glycosylation in a methylotrophic yeast, comprising transforming cells of said methylotrophic yeast with a nucleotide sequence capable of expressing said glycoprotein in said yeast, a vector capable of expressing an α-1,2-mannosidase or a functional part of said α-1,2-mannosidase, and a vector capable of expressing a glucosidase II or a functional part of said glucosidase II, wherein said vector capable of expressing said α-1,2-mannosidase or said functional part of said α-1,2-mannosidase comprises a nucleotide sequence coding for said α-1,2-mannosidase or said functional part of said α-1,2-mannosidase, and said vector capable of expressing said glucosidase II or said functional part of said glucosidase II comprises a nucleotide sequence coding for said glucosidase II or said functional part of said glucosidase II; and producing said glycoprotein in the transformed cells.

4. A kit comprising at least a vector capable of expressing an α-1,2-mannosidase or a functional part of said α-1,2-mannosidase in a methylotrophic yeast strain, and a vector capable of expressing a glucosidase II or a functional part of said glucosidase II in a methylotrophic yeast strain, wherein said vector capable of expressing said α-1,2-mannosidase or said functional part of said α-1,2-mannosidase comprises a nucleotide sequence coding for said α-1,2-mannosidase or said functional part of said α-1,2-mannosidase, and said vector capable of expressing said glucosidase II or said functional part of said glucosidase II comprises a nucleotide sequence coding for said glucosidase II or said functional part of said glucosidase II.

5. A genetically engineered Pichia strain, wherein said strain is transformed with a vector capable of expressing an α-1,2-mannosidase or a functional part of said α-1,2-mannosidase in said Pichia strain, a vector capable of expressing a glucosidase II or a functional part of said glucosidase II in said Pichia strain, and a vector comprising a portion of the *Pichia pastoris* Och1 gene operably linked to a selectable marker gene, wherein said vector capable of expressing said α-1,2-mannosidase or said functional part of said α-1,2-mannosidase comprises a nucleotide sequence coding for said α-1,2-mannosidase or said functional part of said α-1,2-mannosidase, said vector capable of expressing said glucosidase II or said functional part of said glucosidase II comprises a nucleotide sequence coding for said glucosidase II or said functional part of said glucosidase II, and said vector comprising said portion of the *Pichia pastoris* Och1 gene operably linked to said selectable marker gene effects the disruption of the genomic Och1 gene in said Pichia strain.

6. A method of reducing glycosylation of a heterologous glycoprotein expressed from a Pichia strain, comprising transforming cells of said Pichia strain with a vector capable of expressing an α-1,2-mannosidase or a functional part of said α-1,2-mannosidase in said Pichia strain, a vector capable of expressing a glucosidase II or a functional part of said glucosidase II in said Pichia strain, and a vector comprising a portion of the *Pichia pastoris* Och1 gene operably linked to a selectable marker gene, wherein said vector capable of expressing said α-1,2-mannosidase or said functional part of said α-1,2-mannosidase comprises a nucleotide sequence coding for said α-1,2-mannosidase or said functional part of said α-1,2-mannosidase, said vector capable of expressing said glucosidase II or said functional part of said glucosidase II comprises a nucleotide sequence coding for said glucosidase II or said functional part of said glucosidase II, and said vector comprising said portion of the *Pichia pastoris* Och1 gene operably linked to said selectable marker gene effects the disruption of the genomic Och1 gene in the transformed cells of said Pichia strain; and thereby reducing glycosylation of said heterologous glycoprotein.

7. A method of producing a glycoprotein with reduced glycosylation in a Pichia strain, comprising transforming cells of said Pichia strain with a nucleotide sequence capable of expressing said glycoprotein in the yeast cells, a vector capable of expressing an α-1,2-mannosidase or a functional part of said α-1,2-mannosidase in said Pichia strain, a vector capable of expressing a glucosidase II or a functional part of said glucosidase II in said Pichia strain, and a vector comprising a portion of the *Pichia pastoris* Och1 gene operably linked to a selectable marker gene, wherein said vector capable of expressing said α-1,2-mannosidase or said functional part of said α-1,2-mannosidase comprises a nucleotide sequence coding for said α-1,2-mannosidase or said functional part of said α-1,2-mannosidase, said vector capable of expressing said glucosidase II or said functional part of said glucosidase II comprises a nucleotide sequence coding for said glucosidase II or said functional part of said glucosidase II, and said vector comprising said portion of the *Pichia pastoris* Och1 gene operably linked to said selectable marker gene effects the disruption of the genomic Och1 gene in the transformed cells of said Pichia strain; and producing said glycoprotein from the transformed cells.

8. A kit comprising a vector capable of expressing an α-1,2-mannosidase or a functional part of said α-1,2-mannosidase in a Pichia strain, a vector capable of expressing a glucosidase II or a functional part of said glucosidase II in said Pichia strain and a vector comprising a portion of the *Pichia pastoris* Och1 gene and a selectable marker gene, wherein said vector capable of expressing said α-1,2-mannosidase or said functional part comprises a nucleotide sequence coding for said α-1,2-mannosidase or said functional part of said α-1,2-mannosidase, said vector capable of expressing said glucosidase II or said functional part of said glucosidase II comprises a nucleotide sequence coding for said glucosidase II or said functional part of said glucosidase II, and said vector comprising said portion of the Och1 gene and said selectable marker gene effects the disruption of the genomic Och1 gene in said Pichia strain.

9. The genetically engineered methylotrophic yeast strain of claim 1, wherein said α-1,2-mannosidase or said functional part of said α-1,2-mannosidase is genetically engineered to comprise an ER-retention signal.

10. The genetically engineered methylotrophic yeast strain of claim 9, wherein said ER-retention signal comprises peptide HDEL (SEQ ID NO: 1).

11. The method of claim 2, wherein said α-1,2-mannosidase or said functional part of said α-1,2-mannosidase is genetically engineered to comprise an ER-retention signal.

12. The method of claim 11, wherein said ER-retention signal comprises peptide HDEL (SEQ ID NO: 1).

13. The kit of claim 8, wherein said α-1,2-mannosidase or said functional part of said α-1,2-mannosidase is genetically engineered to commise an ER-retention signal.

14. The kit of claim 13, wherein said ER-retention signal comprises peptide HDEL (SEQ ID NO: 1).

15. The genetically engineered methylotrophic yeast strain of claim 1, wherein said glucosidase II or said functional part of said glucosidase II is genetically enaineered to comprise an ER-retention signal.

16. The genetically engineered methylotrophic yeast strain of claim 15, wherein said ER-retention signal comprises peptide HDEL (SEQ ID NO: 1).

17. The method of any one of claims 2, 3, or 6–7, wherein said glucosidase II or said functional part of said glucosidase II is genetically engineered to comprise an ER-retention signal.

18. The method of claim 17, wherein said ER-retention signal comprises peptide HDEL (SEQ ID NO: 1).

19. The kit of claim 4 or 8, wherein said glucosidase II or said functional part of said glucosidase II is genetically engineered to comprise an ER-retention signal.

20. The kit of claim 19, wherein said ER-retention signal comprises peptide HDEL (SEQ ID NO: 1).

21. The Pichia strain of claim 5, wherein said α-1,2-mannosidase or said functional part of said α-1,2-mannosidase is genetically engineered to comprise an ER-retention signal.

22. The Pichia strain of claim 21, wherein said ER-retention signal comprises peptide HDEL (SEQ ID NO: 1).

23. The Pichia strain of claim 5, wherein said glucosidase II or said functional part of said glucosidase II is genetically engineered to comprise an ER-retention signal.

24. The Pichia strain of claim 23, wherein said ER-retention signal comprises peptide HDEL (SEQ ID NO: 1).

25. The strain of claim 1 or 5, wherein said nucleotide sequence coding for said α-1,2-mannosidase or said functional part of said α-1,2-mannosidase and said nucleotide sequence coding for said glucosidase II or said functional part of said glucosidase II are on the same vector.

26. The method according to any one of claims 1, 3, or 6–7 wherein said nucleotide sequence coding for said α-1,2-mannosidase or said functional part of said α-1,2-mannosidase and said nucleotide sequence coding for said glucosidase II or said functional part of said glucosidase II are on the same vector.

27. The strain of claim 5, wherein said portion of the *Pichia pastoris* Och1 gene is on the same vector as either or both of the nucleotide sequence coding for said α-1,2-mannosidase or said functional part of said α-1,2-mannosidase, and the nucleotide sequence coding for said glucosidase II or said functional part of said glucosidase II.

28. The method according to claim 6 or 7, wherein said portion of the *Pichia pastoris* Och1 gene is on the same vector as either or both of the nucleotide sequence coding for said α-1,2-mannosidase or said functional part of said α-1,2-mannosidase, and the nucleotide sequence coding for said glucosidase II or said functional part of said glucosidase II.

* * * * *

SEQUENCE LISTING

<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:synthetic
      peptide representing the ER-retention signal.

<400> SEQUENCE: 1

His Asp Glu Leu
 1

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 2
gactggttcc aattgacaag c                                              21

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 3
agtctagatt acaactcgtc gtgagcaagg tggccgcccc gtcg     44

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 4
ccattgagga cgcatgccgc gcc     23

<210> SEQ ID NO 5
<211> LENGTH: 85
<212> TYPE: DNA
<213> ORGANISM: Artificial Sequence
<220> FEATURE:
<223> OTHER INFORMATION: Description of Artificial Sequence:primer

<400> SEQUENCE: 5
gtatctagat tacaactcgt cgtgcagatc ctcttctgag atgagttttt gttcagcaag     60
gtggccgccc cgtcgtgatg atgaa     85

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 6
aactcgagat ggactcttca aaacacaaac gc     32

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 7
ttgcggccgc ttacaactcg tcgtgtcgga cagcaggatt acctga     46

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 8
ccattgagga cgcatgccgc gcc     23

<210> SEQ ID NO 9
<211> LENGTH: 22
<212> TYPE: DNA
<213> ORGANISM: Artificial Sequence -continued

```
<220> FEATURE:
<223> OTHER INFORMATION: Description of Artificial Sequence:primer

<400> SEQUENCE: 9
gcaaatggca ttctgacatc ct                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 10
gtccctattt caatcaattg aa                                              22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 11
gactggttcc aattgacaag c                                               21

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 12
ccgctcgaga tggtcctttt gaaatggctc                                      30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 13
ccgggcccaa aaataacttc ccaatcttca g                                    31

<210> SEQ ID NO 14
<211> LENGTH: 1785
<212> TYPE: DNA
<213> ORGANISM: Artificial Sequence
<220> FEATURE:
<223> OTHER INFORMATION: Description of Artificial Sequence:The ORF
      sequence of the MFManHDEL fusion in
      pGAPZMFManHDEL.

<400> SEQUENCE: 14
atgagatttc cttcaatttt tactgctgtt ttattcgcag catcctccgc attagctgct     60
ccagtcaaca ctacaacaga agatgaaacg gcacaaattc cggctgaagc tgtcatcggt    120
tactcagatt tagaagggga tttcgatgtt gctgttttgc cattttccaa cagcacaaat    180
aacgggttat tgtttataaa tactactatt gccagcattg ctgctaaaga agaagggta    240 tctctcgaga aaagagaggc tgaagctgaa ttcgccacaa acgtggatc tcccaaccct    300 acgagggcgg cagcagtcaa ggccgcattc cagacgtcgt ggaacgctta ccaccatttt    360
```

```
gcctttcccc atgacgacct ccacccggtc agcaacagct ttgatgatga gagaaacggc      420
tggggctcgt cggcaatcga tggcttggac acggctatcc tcatggggga tgccgacatt      480
gtgaacacga tccttcagta tgtaccgcag atcaacttca ccacgactgc ggttgccaac      540
caaggatcct ccgtgttcga gaccaacatt cggtacctcg gtggcctgct ttctgcctat      600
gacctgttgc gaggtccttt cagctccttg gcgacaaacc agaccctggt aaacagcctt      660
ctgaggcagg ctcaaacact ggccaacggc ctcaaggttg cgttcaccac tcccagcggt      720
gtcccggacc ctaccgtctt cttcaaccct actgtccgga aagtggtgc atctagcaac       780 aacgtcgctg aaattggaag cctggtgctc gagtggacac ggttgagcga cctgacggga      840
aacccgcagt atgcccagct tgcgcagaag ggcgagtcgt atctcctgaa tccaaaggga      900
agcccggagg catggcctgg cctgattgga acgtttgtca gcacgagcaa cggtaccttt      960
caggatagca gcggcagctg gtccggcctc atggacagct tctacgagta cctgatcaag     1020
atgtacctgt acgacccggt tgcgtttgca cactacaagg atcgctgggt ccttggtgcc     1080
gactcgacca ttgggcatct cggctctcac ccgtcgacgc gcaaggactt gacctttttg     1140
tcttcgtaca acgacagtc tacgtcgcca aactcaggac atttggccag ttttggcggt      1200
ggcaacttca tcttgggagg cattctcctg aacgagcaaa agtacattga ctttggaatc     1260
aagcttgcca gctcgtactt tggcacgtac acccagacgg cttctggaat cggccccgaa     1320
ggcttcgcgt gggtggacag cgtgacgggc gccggcggct cgccgccctc gtcccagtcc     1380
gggttctact cgtcggcagg attctgggtg acggcaccgt attacatcct gcggccggag     1440
acgctggaga gcttgtacta cgcataccgc gtcacgggcg actccaagtg caggacctg      1500 gcgtgggaag cgttgagtgc cattgaggac gcatgccgcg ccggcagcgc gtactcgtcc     1560
atcaacgacg tgacgcaggc caacggcggg ggtgcctctg acgatatgga gagcttctgg     1620
tttgccgagg cgctcaagta tgcgtacctg atctttgcgg aggagtcgga tgtgcaggtg     1680
caggccaccg gcgggaacaa atttgtcttt aacacggagg cgcacccctt tagcatccgt     1740
tcatcatcac gacggggcgg ccaccttgct cacgacgagt tgtaa                     1785
```

<210> SEQ ID NO 15
<211> LENGTH: 2016
<212> TYPE: DNA
<213> ORGANISM: Artificial Sequence
<220> FEATURE:
<223> OTHER INFORMATION: Description of Artificial Sequence:The ORF
      sequence of the MFmManHDEL fusion in
      pGAPZMFmManHDEL.

<400> SEQUENCE: 15

```
atgagatttc cttcaatttt tactgctgtt ttattcgcag catcctccgc attagctgct       60
ccagtcaaca ctacaacaga agatgaaacg gcacaaattc cggctgaagc tgtcatcggt      120
tactcagatt tagaagggga tttcgatgtt gctgttttgc catttccaa cagcacaaat      180 aacgggttat tgtttataaa tactactatt gccagcattg ctgctaaaga agaaggggta      240
tctctcgaga tggactcttc aaaacacaaa cgctttgatc tgggcttaga agatgtgtta      300
attcctcacg tagatgccgg caaaggagct aaaaaccccg gcgtcttcct gatccatgga      360
cccgacgaac acagacacag ggaagaagaa gagcgtctga aaataagat tagagctgac      420 catgagaaag ccctggaaga agcaaaagaa aaattaagaa agtcaagaga ggaaatccgt      480
gcagaaattc agacagagaa aaacaaagta gcccaagcaa tgaagacaaa agagaccagg      540
gtactgccgc ctgtccctgt cccacaacgt gtaggggtca gtggtgggga tccagaagac      600
```

```
atggagatca agaagaaaag agacaaaatt aaagagatga tgaaacatgc ctgggataat      660
tacagaacat acggatgggg acataatgaa ctaaggccta ttgcaaggaa aggccattcc      720
actaacatat cggaagctc acagatgggt gccaccatag tggatgcttt ggatacccctt     780 tatatcatgg ggcttcatga tgaattcatg gatgggcaaa gatggattga agaaaacctt     840
gatttcagtg tgaattcaga agtgtctgtc tttgaagtta acattcgctt tattggaggg     900
ctcctcgctg catattacct gtcaggagag gaaatattca agactaaagc agtgcagttg     960
gctgagaaac tccttcctgc ctttaacaca cctactggga ttccctgggc aatggtgaac    1020
ctgaaaagtg gagtaggtcg aaactggggc tgggcgtctg caggcagcag catcctggct    1080
gagttcggca ccctgcacat ggagtttgtg cacctcagct acttgaccgg tgacttgact    1140
tactataata aggtcatgca cattcggaaa ctactgcaga aaatggaacg cccaaatggt    1200
ctttatccaa attatttaaa cccaagaaca gggcgctggg gtcagtatca cacatcagtt    1260
ggtggtctgg gagatagttt ttatgaatac ttactgaaag catggctgac gtcagataaa    1320
acagaccacg aggcaagaag gatgtatgac gatgctgttg aggctataga aaaacatctt    1380
attaagaagt cccgaggagg tctggttttt attggagaat ggaagaatgg acacttggaa    1440
aggaagatgg ggcacttggc ctgctttgct ggggaatgc ttgcccttgg agcagatggt    1500
tccagaaagg ataaagctgg ccactactta gaactagggg cagaaattgc acgaacatgt    1560
catgagtcat atgacagaac tgcattgaaa ctaggtccgg agtcattcaa gtttgatggt    1620
gcagtggaag ccgtggctgt gcggcaggct gaaaagtatt acatccttcg tccagaagta    1680
attgaaacct attggtatct atggcgattt acccacgacc caagatacag gcagtggggc    1740
tgggaagcag cactggctat tgagaagtcg tgccgggtca gcgtggggtt ttctggtgtc    1800
aaggatgtat acgccccgac ccctgtgcat gacgacgtgc agcagagctt ttctcttgct    1860
gaaacattaa aatacttgta cctgctgttc tctggcgatg accttctacc tttagaccac    1920
tgggtgttta acacagaggc gcaccctctg ccggtgttgc gcttagccaa cagcactctt    1980
tcaggtaatc ctgctgtccg acacgacgag ttgtaa                              2016
```

<210> SEQ ID NO 16
<211> LENGTH: 6757
<212> TYPE: DNA
<213> ORGANISM: Artificial Sequence
<220> FEATURE:
<223> OTHER INFORMATION: Description of Artificial Sequence:Sequence of
      plasmid pAOX2ZAGLSII.

<400> SEQUENCE: 16

```
catggccaag ttgaccagtg ccgttccggt gctcaccgcg cgcgacgtcg ccggagcggt       60
cgagttctgg accgaccggc tcgggttctc ccgggacttc gtggaggacg acttcgccgg      120
tgtggtccgg gacgacgtga ccctgttcat cagcgcggtc caggaccagg tggtgccgga      180
caacaccctg gcctgggtgt gggtgcgcgg cctggacgag ctgtacgccg agtggtcgga      240
ggtcgtgtcc acgaacttcc gggacgcctc cgggccggcc atgaccgaga tcggcgagca      300
gccgtggggg cggagttcg ccctgcgcga cccggccggc aactgcgtgc acttcgtggc      360
cgaggagcag gactgacacg tccgacgcg gcccacgggt cccaggcctc ggagatccgt      420 ccccctttttc ctttgtcgat atcatgtaat tagttatgtc acgcttacat tcacgccctc      480 ccccacatc cgctctaacc gaaaggaag gagttagaca acctgaagtc taggtcccta      540 tttattttt tatagttatg ttagtattaa gaacgttatt tatatttcaa attttttcttt      600
```

-continued

```
tttttctgta cagacgcgtg tacgcatgta acattatact gaaaaccttg cttgagaagg    660
ttttgggacg ctcgaaggct ttaatttgca agctggagac caacatgtga gcaaaaggcc    720
agcaaaaggc caggaaccgt aaaaaggccg cgttgctggc gttttttccat aggctccgcc    780
cccctgacga gcatcacaaa aatcgacgct caagtcagag gtggcgaaac ccgacaggac    840
tataaagata ccaggcgttt cccccctggaa gctccctcgt gcgctctcct gttccgaccc    900
tgccgcttac cggatacctg tccgcctttc tcccttcggg aagcgtggcg ctttctcaat    960
gctcacgctg taggtatctc agttcggtgt aggtcgttcg ctccaagctg ggctgtgtgc   1020
acgaaccccc cgttcagccc gaccgctgcg ccttatccgg taactatcgt cttgagtcca   1080
acccggtaag acacgactta tcgccactgg cagcagccac tggtaacagg attagcagag   1140
cgaggtatgt aggcggtgct acagagttct tgaagtggtg gcctaactac ggctacacta   1200
gaaggacagt atttggtatc tgcgctctgc tgaagccagt taccttcgga aaaagagttg   1260
gtagctcttg atccggcaaa caaaccaccg ctggtagcgg tggttttttt gtttgcaagc   1320
agcagattac gcgcagaaaa aaaggatctc aagaagatcc tttgatcttt tctacggggt   1380
ctgacgctca gtggaacgaa aactcacgtt aagggatttt ggtcatgaga tcagatcttt   1440
ttttcagacc atatgaccgg tccatcttct acgggggat tatctatgct ttgacctcta   1500
tcttgattct tttatgattc aaatcacttt tacgttattt attacttact ggttatttac   1560
ttagcgcctt ttctgaaaaa catttactaa aaatcataca tcggcactct caaacacgac   1620
agattgtgat caagaagcag agacaatcac cactaaggtt gcacatttga gccagtaggc   1680
tcctaataga ggttcgatac ttattttgat aatacgacat attgtcttac ctctgaatgt   1740
gtcaatactc tctcgttctt cgtctcgtca gctaaaaata taacacttcg agtaagatac   1800
gcccaattga aggctacgag ataccagact atcactagta gaactttgac atctgctaaa   1860
gcagatcaaa tatccattta tccagaatca attaccttcc tttagcttgt cgaaggcatg   1920
aaaaagctac atgaaaatcc ccatccttga agttttgtca gcttaaagga ctccatttcc   1980
taaaatttca agcagtcctc tcaactaaat tttttttccat tcctctgcac ccagccctct   2040
tcatcaaccg tccagccttc tcaaaagtcc aatgtaagta gcctgcaaat tcaggttaca   2100
acccctcaat tttccatcca agggcgatcc ttacaaagtt aatatcgaac agcagagact   2160
aagcgagtca tcatcaccac ccaacgatgg tgaaaaactt taagcataga ttgatggagg   2220
gtgtatggca cttggcggct gcattagagt ttgaaactat ggggtaatac atcacatccg   2280
gaactgatcc gactccgaga tcatatgcaa agcacgtgat gtaccccgta aactgctcgg   2340
attatcgttg caattcatcg tcttaaacag tacaagaaac tttattcatg ggtcattgga   2400
ctctgatgag gggcacattt ccccaatgat ttttgggaa agaaagccgt aagaggacag   2460
ttaagcgaaa gagacaagac aacgaacagc aaaagtgaca gctgtcagct acctagtgga   2520
cagttgggag tttccaattg gttggttttg aatttttacc catgttgagt tgtccttgct   2580
tctccttgca aacaatgcaa gttgataaga catcaccttc caagataggc tatttttgtc   2640
gcataaattt ttgtctcgga gtgaaaaccc cttttatgtg aacagattac agaagcgtcc   2700
taccccttcac cggttgagat gggagaaaaa ttaagcgatg aggagacgat tattggtata   2760
aagaagcaa ccaaaatccc ttattgtcct tttctgatca gcatcaaaga atattgtctt   2820
aaaacgggct tttaactaca ttgttcttac acattgcaaa cctcttcctt ctatttcgga   2880
tcaactgtat tgactacatt gatcttttt aacgaagttt acgacttact aaatccccac   2940
```

```
aaacaaatca actgagaaaa gaattcacgt ggcccagccg gccgtctcgg atcggtacct    3000
cgagatggtc cttttgaaat ggctcgtatg ccaattggtc ttctttaccg cttttttcgca   3060
tgcgtttacc gactatctat taaagaagtg tgcgcaatct gggttttgcc atagaaacag    3120
ggtttatgca gaaaatattg ccaaatctca tcactgctat tacaaagtgg acgccgagtc    3180
tattgcacac gatcctttag agaatgtgct tcatgctacc ataattaaaa ctataccaag    3240
attggagggc gatgatatag ccgttcagtt cccattctct ctctcttttt tacaggatca    3300
ctcagtaagg ttcactataa atgagaaaga gagaatgcca accaacagca gcggtttgtt    3360
gatctcttca caacggttca atgagacctg gaagtacgca ttcgacaaga aatttcaaga    3420
ggaggcgaac aggaccagta ttccacaatt ccacttcctt aagcaaaaac aaactgtgaa    3480
ctcattctgg tcgaaaatat cttcattttt gtcactttca aactccactg cagacacatt    3540
tcatcttcga aacggtgatg tatccgtaga atctttgct gaaccttttc aattgaaagt     3600
ttactggcaa aatgcgctga aacttattgt aaacgagcaa aatttcctga acattgaaca    3660
tcatagaact aagcaggaaa acttcgcaca cgtgctgcca aagaaacaa ctttcaacat     3720
gtttaaggac aatttcttgt attcaaagca tgactctatg cctttggggc ctgaatcggt    3780
tgcgctagat ttctctttca tgggttctac taatgtctac ggtataccgg aacatgcgac    3840
gtcgctaagg ctgatggaca cttcaggtgg aaaggaaccc tacaggcttt tcaacgttga    3900
tgtctttgag tacaacatcg gtaccagcca accaatgtac ggttcgatcc cattcatgtt    3960
ttcatcttcg tccacatcta tcttttgggt caatgcagct gacacttggg tagacataaa    4020
gtatgacacc agtaaaaata aaacgatgac tcattggatc tccgaaaatg gtgtcataga    4080
tgtagtcatg tccctggggc cagatattcc aactatcatt gacaaattta ccgatttgac    4140
tggtagaccc ttttttaccgc ccatttcctc tatagggtac catcaatgta gatggaatta   4200
taatgatgag atggacgttc tcacagtgga ctctcagatg gatgctcata tgattcctta    4260
cgattttatt tggttggact tggagtatac gaacgacaaa aaatatttta cttggaagca    4320
gcactccttt cccaatccaa aaaggctgtt atccaaatta aaaagttggg gtagaaatct    4380
tgtcgtacta atcgatcctc atttaaagaa agattatgaa atcagtgaca gggtaattaa    4440
tgaaaatgta gcagtcaagg atcacaatgg aaatgactat gtaggtcatt gctggccagg    4500
taattctata tggattgata ccataagcaa atatggccaa aagatttgga agtccttttt    4560
cgaacggttt atgatctgc cggctgattt aactaattta ttcatttgga atgatatgaa     4620
cgagccttcg attttcgatg gcccagagac cacagctcca aaagatttga ttcacgacaa    4680
ttacattgag gaaagatccg tccataacat atatggtcta tcagtgcatg aagctactta    4740
cgacgcaata aaatcgattt attccaccatc cgataagcgt cctttccttc taacaagggc    4800
tttttttgcc ggctctcaac gtactgctgc cacatggact ggtgacaatg tggccaattg    4860
ggattactta aagatttcca ttcctatggt tctgtcaaac aacattgctg gtatgccatt    4920
tataggagcc gacatagctg gctttgctga ggatcctaca cctgaattga ttgcacgttg    4980
gtaccaagcg ggcttatggt acccattttt tagagcacac gcccatatag acaccaagag    5040
aagagaacca tacttattca atgaaccttt gaagtcgata gtacgtgata ttatccaatt    5100
gagatatttc ctgctaccta ccttatacac catgtttcat aaatcaagtg tcactggatt    5160
tccgataatg aatccaatgt ttattgaaca ccctgaattt gctgaattgt atcatatcga    5220
taaccaattt tactggagta attcaggtct attagtcaaa cctgtcacgg agcctggtca    5280
atcagaaacg gaaatggttt tcccacccgg tatattctat gaattcgcat cttttacactc    5340
```

```
ttttataaac aatggtactg atttgataga aaagaatatt tctgcaccat tggataaaat    5400
tccattattt attgaaggcg gtcacattat cactatgaaa gataagtata aagatcttc     5460 aatgttaatg aaaacgatc catatgtaat agtatagcc cctgataccg agggacgagc      5520
cgttggagat ctttatgttg atgatggaga aacttttggc taccaaagag gtgagtacgt    5580
agaaactcag ttcattttcg aaaacaatac cttaaaaaat gttcgaagtc atattcccga    5640
gaatttgaca ggcattcacc acaatacttt gaggaatacc aatattgaaa aaatcattat    5700
cgcaaagaat aatttacaac acaacataac gttgaaagac agtattaaag tcaaaaaaaa    5760
tggcgaagaa agttcattgc cgactagatc gtcatatgag aatgataata agatcaccat    5820
tcttaaccta tcgcttgaca taactgaaga ttgggaagtt attttttgggc ccgaacaaaa   5880 actcatctca gaagaggatc tgaatagcgc cgtcgaccat catcatcatc atcattgagt    5940
tttagcctta gacatgactg ttcctcagtt caagttgggc acttacgaga agaccggtct    6000
tgctagattc taatcaagag gatgtcagaa tgccatttgc ctgagagatg caggcttcat    6060
ttttgatact ttttatttg taacctatat agtataggat ttttttttgtc attttgtttc    6120 ttctcgtacg agcttgctcc tgatcagcct atctcgcagc tgatgaatat cttgtggtag    6180
gggtttggga aaatcattcg agtttgatgt ttttcttggt atttcccact cctcttcaga    6240
gtacagaaga ttaagtgaga ccttcgtttg tgcggatccc ccacacacca tagcttcaaa    6300
atgtttctac tccttttta ctcttccaga ttttctcgga ctccgcgcat cgccgtacca    6360
cttcaaaaca cccaagcaca gcatactaaa ttttccctct ttcttcctct agggtgtcgt    6420
taattacccg tactaaaggt ttggaaaaga aaaagagac cgcctcgttt cttttttcttc    6480 gtcgaaaaag gcaataaaaa ttttttatcac gtttctttt cttgaaattt ttttttttag    6540 ttttttttctc tttcagtgac ctccattgat atttaagtta ataaacggtc ttcaatttct   6600
caagtttcag tttcattttt cttgttctat tacaacttttt tttacttctt gttcattaga   6660
aagaaagcat agcaatctaa tctaagggcg gtgttgacaa ttaatcatcg gcatagtata    6720
tcggcatagt ataatacgac aaggtgagga actaaac                             6757
```

<210> SEQ ID NO 17
<211> LENGTH: 8272
<212> TYPE: DNA
<213> ORGANISM: Artificial Sequence
<220> FEATURE:
<223> OTHER INFORMATION: Description of Artificial Sequence:Sequence of
      plasmid pAOX2ADE1glsII.

<400> SEQUENCE: 17

```
tcgaccggct gcattaatga atcggccaac gcgcggggag aggcggtttg cgtattgggc     60
gctcttccgc ttcctcgctc actgactcgc tgcgctcggt cgttcggctg cggcgagcgg    120
tatcagctca ctcaaaggcg gtaatacggt tatccacaga atcaggggat aacgcaggaa    180
agaacatgtg agcaaaaggc cagcaaaagg ccaggaaccg taaaaaggcc gcgttgctgg    240
cgttttccca taggctccgc cccctgacg agcatcacaa aaatcgacgc tcaagtcaga    300
ggtggcgaaa cccgacagga ctataaagat accaggcgtt tccccctgga agctccctcg    360
tgcgctctcc tgttccgacc ctgccgctta ccggatacct gtccgccttt ctcccttcgg    420
gaagcgtggc gctttctcat agctcacgct gtaggtatct cagttcggtg taggtcgttc    480
gctccaagct gggctgtgtg cacgaacccc ccgttcagcc cgaccgctgc gccttatccg    540
gtaactatcg tcttgagtcc aacccggtaa gacacgactt atcgccactg gcagcagcca    600
```

-continued

```
ctggtaacag gattagcaga gcgaggtatg taggcggtgc tacagagttc ttgaagtggt      660
ggcctaacta cggctacact agaaggacag tatttggtat ctgcgctctg ctgaagccag      720
ttaccttcgg aaaaagagtt ggtagctctt gatccggcaa acaaaccacc gctggtagcg      780
gtggtttttt tgtttgcaag cagcagatta cgcgcagaaa aaaggatctc aagaagatc       840
ctttgatctt ttctacgggg tctgacgctc agtggaacga aaactcacgt taagggattt      900
tggtcatgag attatcaaaa aggatcttca cctagatcct tttaaattaa aaatgaagtt     960
ttaaatcaat ctaaagtata tatgagtaaa cttggtctga cagttaccaa tgcttaatca    1020
gtgaggcacc tatctcagcg atctgtctat ttcgttcatc catagttgcc tgactccccg    1080
tcgtgtagat aactacgata cgggagggct taccatctgg ccccagtgct gcaatgatac    1140
cgcgagaccc acgctcaccg gctccagatt tatcagcaat aaaccagcca gccggaaggg    1200
ccgagcgcag aagtggtcct gcaactttat ccgcctccat ccagtctatt aattgttgcc    1260
gggaagctag agtaagtagt tcgccagtta atagtttgcg caacgttgtt gccattgcta    1320
caggcatcgt ggtgtcacgc tcgtcgtttg gtatggcttc attcagctcc ggttcccaac    1380
gatcaaggcg agttacatga tcccccatgt tgtgcaaaaa agcggttagc tccttcggtc    1440
ctccgatcgt tgtcagaagt aagttggccg cagtgttatc actcatggtt atggcagcac    1500
tgcataattc tcttactgtc atgccatccg taagatgctt ttctgtgact ggtgagtact    1560
caaccaagtc attctgagaa tagtgtatgc ggcgaccgag ttgctcttgc ccggcgtcaa    1620
tacgggataa taccgcgcca catagcagaa ctttaaaagt gctcatcatt ggaaaacgtt    1680
cttcggggcg aaaactctca aggatcttac cgctgttgag atccagttcg atgtaaccca    1740
ctcgtgcacc caactgatct tcagcatctt ttactttcac cagcgtttct gggtgagcaa    1800
aaacaggaag gcaaaatgcc gcaaaaaagg gaataagggc gacacggaaa tgttgaatac    1860
tcatactctt cctttttcaa tagctccaag gcaacaaatt gactactcag accgacattc    1920
attcgttatt gattttaaat caacgataaa cggaatggtt acttgaatga tttcactta    1980
tgatcattgt ttactaatta cctaaatagg attttatatg gaattggaag ataagggaa    2040
atttcagatg tctgaaaaag gcgaggaggg tactaatcat tcaagcccat tcttgccag    2100
taattgcttc ataagcttca atatacttt ctttactctt gatagcaatt tctgcatcca    2160
tggctacgcc ctctttgcca ttcaatccgt tggccgtcaa ccaatctctg agaaactgct    2220
tatcgtaact ctcttgcgat ttacccactt ggtaagtctt ttgattccaa aatctagaag    2280
aatctggagt taaaacttca tctactagta ccaattcatt gttttcgtcc agtccaaatt    2340
cgaatttcgt atcagcaata atgatcccct tcaaagggc gaagtttttt gcagcagaat    2400
acaactcgac cgccttgaca gcgaccttct cacaaatgtc tttacctaca atctcagcag    2460
cttgttcaat agagatgttt tcatcgtgtt cacgctgttc agctttcgtt gaaggtgtga    2520
aaatcggagt tggaaaggcg tcgctctctt gaaggttctc gttttcaacc ttgactccat    2580
ggacagtttt tgagttcttg tactctttcc atgcacttcc agtgatgtaa cctctgacaa    2640
tggcttccaa aggtatcagt ctgtgctttt ttactatcaa ggatcgtccc tctaattgag    2700
atttgtattt tcttcagac agttttgatg gtagtaaagc aaagacttcc ttgtcattag    2760
aagcaaccaa atgattcttt atgtagggtg ccaaaaaatc aaaccagaaa actgagagct    2820
gagtcaaaat ctttccctta tcaggaatac cgtttgtcat aatcacatcg taagcggaga    2880
tacggtcagt tgcgacgaac agcaagttgt tctcatcgac tgcataaatg tctctaaccct    2940
```

```
ttcctttggc gattaaaggt aggattccgt ccagatcagt gttcacaatg gacatacttg   3000
gaaggataca gcaaagtgtg ttggaagcga tgacacatgg aaaggaattt ttcgagtttc   3060
ctagagtagt atattggggc ggtgaaagtt cagatgttta atgcttaata ctcttatact   3120
cttcaaagcg cccaagtgtt tctgccaacc tgacttttt ctgaataatg aatcgttcaa    3180
gtggagtatt taaccatga ttaagttacg tgatttggca ctggataagg tcgaaaaata    3240
tccgtattca taaacgatta ttggtaaaag ttacaaaata ccactaatta cggagaagct   3300
tagtaacagt tatcatctct tggtcgatta acgcttacaa tttccattcg ccattcaggc   3360
tgcgcaactg ttgggaaggg cgatcggtgc gggcctcttc gctattacgc cagggcctcg   3420
aggcacaaac gaacgtctca cttaatcttc tgtactctga agaggagtgg gaaataccaa   3480
gaaaaacatc aaactcgaat gattttccca acccctacc acaagatatt catcagctgc    3540
gagataggct gatcaggagc aagctcgtac gagaagaaac aaaatgacaa aaaaaatcct   3600
atactatata ggttacaaat aaaaaagtat caaaaatgaa gcctgcatct ctcaggcaaa   3660
tggcattctg acatcctctt gattagaatc tagcaagacc ggtcttctcg taagtgccca   3720
acttgaactg aggaacagtc atgtctaagg ctaaaactca atgatgatga tgatgatggt   3780
cgacggcgct attcagatcc tcttctgaga tgagttttg ttcgggccca aaaataactt    3840
cccaatcttc agttatgtca agcgataggt aagaatggt gatcttatta tcattctcat    3900
atgacgatct agtcggcaat gaactttctt cgccattttt tttgacttta atactgtctt   3960
tcaacgttat gttgtgttgt aaattattct ttgcgataat gattttttca atattggtat   4020
tcctcaaagt attgtggtga atgcctgtca aattctcggg aatatgactt cgaacatttt   4080
ttaaggtatt gttttcgaaa atgaactgag tttctacgta ctcacctctt tggtagccaa   4140
aagtttctcc atcatcaaca taaagatctc caacggctcg tccctcggta tcagggggcta  4200 taactattac atatggatcg tttttcatta acattgaaga tcttctatac ttatctttca   4260
tagtgataat gtgaccgcct tcaataaata atggaatttt atccaatggt gcagaaatat   4320
tcttttctat caaatcagta ccattgttta taaagagtg taaagatgcg aattcataga    4380
atataccggg tgggaaaacc atttccgttt ctgattgacc aggctccgtg acaggtttga   4440
ctaatagacc tgaattactc cagtaaaatt ggttatcgat atgatacaat tcagcaaatt   4500
cagggtgttc aataaacatt ggattcatta tcggaaatcc agtgacactt gatttatgaa   4560
acatggtgta taaggtaggt agcaggaaat atctcaattg gataatatca cgtactatcg   4620
acttcaaagg ttcattgaat aagtatggtt ctcttctctt ggtgtctata tgggcgtgtg   4680
ctctaaaaaa tgggtaccat aagcccgctt ggtaccaacg tgcaatcaat tcaggtgtag   4740
gatcctcagc aaagccagct atgtcggctc ctataaatgg cataccagca atgttgtttg   4800
acagaaccat aggaatggaa atctttaagt aatcccaatt ggccacattg tcaccagtcc   4860
atgtggcagc agtacgttga gagccggcaa aaaaagccct tgttagaagg aaaggacgct   4920
tatcggatgg tgaataaatc gatttattg cgtcgtaagt agcttcatgc actgatagac    4980
catatatgtt atggacggat cttccctcaa tgtaattgtc gtgaatcaaa tcttttggag   5040
ctgtggtctc tgggccatcg aaaatcgaag gctcgttcat atcattccaa atgaataaat   5100
tagttaaatc agccggcaga tccataaacc gttcgaaaaa ggacttccaa atcttttggc   5160
catatttgct tatggtatca atccatatag aattacctgg ccagcaatga cctacatagt   5220
catttccatt gtgatccttg actgctacat tttcattaat taccctgtca ctgatttcat   5280
aatctttctt taaatgagga tcgattagta cgacaagatt tctacccaac tttttaatt    5340
```

-continued

```
tggataacag ccttttttgga ttgggaaagg agtgctgctt ccaagtaaaa tattttttgt    5400
cgttcgtata ctccaagtcc aaccaaataa aatcgtaagg aatcatatga gcatccatct    5460
gagagtccac tgtgagaacg tccatctcat cattataatt ccatctacat tgatggtacc    5520
ctatagagga aatgggcggt aaaaagggtc taccagtcaa atcggtaaat ttgtcaatga    5580
tagttggaat atctggcccc agggacatga ctacatctat gacaccattt tcggagatcc    5640
aatgagtcat cgttttattt ttactggtgt catactttat gtctacccaa gtgtcagctg    5700
cattgaccca aaagatagat gtggacgaag atgaaaacat gaatgggatc gaaccgtaca    5760
ttggttggct ggtaccgatg ttgtactcaa agacatcaac gttgaaaagc ctgtagggtt    5820
cctttccacc tgaagtgtcc atcagcctta gcgacgtcgc atgttccggt ataccgtaga    5880
cattagtaga acccatgaaa gagaaatcta gcgcaaccga ttcaggcccc aaaggcatag    5940
agtcatgctt tgaatacaag aaattgtcct taaacatgtt gaaagttgtt tcttctggca    6000
gcacgtgtgc gaagttttcc tgcttagttc tatgatgttc aatgttcagg aaattttgct    6060
cgtttacaat aagtttcagc gcattttgcc agtaaacttt caattgaaaa ggttcagcaa    6120
agatttctac ggatacatca ccgtttcgaa gatgaaatgt gtctgcagtg gagtttgaaa    6180
gtgacaaaaa tgaagatatt ttcgaccaga atgagttcac agtttgtttt tgcttaagga    6240
agtggaattg tggaatactg gtcctgttcg cctcctcttg aaatttcttg tcgaatgcgt    6300
acttccaggt ctcattgaac cgttgtgaag agatcaacaa accgctgctg ttggttggca    6360
ttctctcttt ctcattttata gtgaaccttta ctgagtgatc ctgtaaaaaa gagagagaga    6420
atgggaactg aacggctata tcatcgccct ccaatcttgg tatagtttta attatggtag    6480
catgaagcac attctctaaa ggatcgtgtg caatagactc ggcgtccact ttgtaatagc    6540
agtgatgaga tttggcaata ttttctgcat aaaccctgtt tctatggcaa acccagatt    6600 gcgcacactt ctttaataga tagtcggtaa acgcatgcga aaaagcggta aagaagacca    6660
attggcatac gagccatttc aaaaggacca tctcgaggta ccgatccgag acggccggct    6720
gggccacgtg aattcttttc tcagttgatt tgtttgtggg gatttagtaa gtcgtaaact    6780
tcgttaaaaa agatcaatgt agtcaataca gttgatccga aatagaagga agaggtttgc    6840
aatgtgtaag aacaatgtag ttaaaagccc gttttaagac aatattcttt gatgctgatc    6900
agaaaaggac aataagggat tttggttgct tcttttatac caataatcgt ctcctcatcg    6960
cttaattttc tccccatctc aaccggtgaa gggtaggacg cttctgtaat ctgttcacat    7020 aaaagggggtt ttcactccga gacaaaaatt tatgcgacaa aaatagccta tcttggaagg    7080
tgatgtctta tcaacttgca ttgtttgcaa ggagaagcaa ggacaactca acatgggtaa    7140
aaattcaaaa ccaaccaatt ggaaactccc aactgtccac taggtagctg acagctgtca    7200
cttttgctgt tcgttgtctt gtctcttttcg cttaactgtc ctcttacggc tttctttccc    7260
aaaaaatcat tggggaaatg tgcccctcat cagagtccaa tgacccatga ataaagtttc    7320
ttgtactgtt taagacgatg aattgcaacg ataatccgag cagtttacgg ggtacatcac    7380
gtgctttgca tatgatctcg gagtcggatc agttccggat gtgatgtatt accccatagt    7440
ttcaaactct aatgcagccg ccaagtgcca tacaccctcc atcaatctat gcttaaagtt    7500
tttcaccatc gttgggtggt gatgatgact cgcttagtct ctgctgttcg atattaactt    7560
tgtaaggatc gcccttggat ggaaaattga ggggttgtaa cctgaatttg caggctactt    7620
acattggact tttgagaagg ctggacggtt gatgaagagg gctgggtgca gaggaatgga    7680
```

-continued

| aaaaaattta | gttgagagga | ctgcttgaaa | ttttaggaaa | tggagtcctt | taagctgaca | 7740 |
| aaacttcaag | gatggggatt | ttcatgtagc | tttttcatgc | cttcgacaag | ctaaaggaag | 7800 |
| gtaattgatt | ctggataaat | ggatatttga | tctgctttag | cagatgtcaa | agttctacta | 7860 |
| gtgatagtct | ggtatctcgt | agccttcaat | tgggcgtatc | ttactcgaag | tgttatattt | 7920 |
| ttagctgacg | agacgaagaa | cgagagagta | ttgacacatt | cagaggtaag | acaatatgtc | 7980 |
| gtattatcaa | aataagtatc | gaacctctat | taggagccta | ctggctcaaa | tgtgcaacct | 8040 |
| tagtggtgat | tgtctctgct | tcttgatcac | aatctgtcgt | gtttgagagt | gccgatgtat | 8100 |
| gatttttagt | aaatgttttt | cagaaaaggc | gctaagtaaa | taaccagtaa | gtaataaata | 8160 |
| acgtaaaagt | gatttgaatc | ataaaagaat | caagatagag | gtcaaagcat | agataatccc | 8220 |
| cccgtagaag | atggaccggt | catatggtct | gaaaaaaga | tctgatctca | tg | 8272 |

<210> SEQ ID NO 18
<211> LENGTH: 5727
<212> TYPE: DNA
<213> ORGANISM: Artificial Sequence
<220> FEATURE:
<223> OTHER INFORMATION: Description of Artificial Sequence:Sequence of
      plasmid pGAPZAGLSII.

<400> SEQUENCE: 18

| tcgagatggt | ccttttgaaa | tggctcgtat | gccaattggt | cttctttacc | gcttttcgc | 60 |
| atgcgtttac | cgactatcta | ttaaagaagt | gtgcgcaatc | tgggttttgc | catagaaaca | 120 |
| gggtttatgc | agaaaatatt | gccaaatctc | atcactgcta | ttacaaagtg | gacgccgagt | 180 |
| ctattgcaca | cgatccttta | gagaatgtgc | ttcatgctac | cataattaaa | actataccaa | 240 |
| gattggaggg | cgatgatata | gccgttcagt | tcccattctc | tctctctttt | ttacaggatc | 300 |
| actcagtaag | gttcactata | aatgagaaag | agagaatgcc | aaccaacagc | agcggtttgt | 360 |
| tgatctcttc | acaacggttc | aatgagacct | ggaagtacgc | attcgacaag | aaatttcaag | 420 |
| aggaggcgaa | caggaccagt | attccacaat | tccacttcct | taagcaaaaa | caaactgtga | 480 |
| actcattctg | gtcgaaaata | tcttcatttt | tgtcactttc | aaactccact | gcagacacat | 540 |
| ttcatcttcg | aaacggtgat | gtatccgtag | aaatctttgc | tgaaccttt | caattgaaag | 600 |
| tttactggca | aaatgcgctg | aaacttattg | taaacgagca | aaatttcctg | aacattgaac | 660 |
| atcatagaac | taagcaggaa | aacttcgcac | acgtgctgcc | agaagaaaca | actttcaaca | 720 |
| tgtttaagga | caatttcttg | tattcaaagc | atgactctat | gcctttgggg | cctgaatcgg | 780 |
| ttgcgctaga | tttctctttc | atgggttcta | ctaatgtcta | cggtataccg | gaacatgcga | 840 |
| cgtcgctaag | gctgatggac | acttcaggtg | gaaaggaacc | ctacaggctt | tcaacgttg | 900 |
| atgtctttga | gtacaacatc | ggtaccagcc | aaccaatgta | cggttcgatc | ccattcatgt | 960 |
| tttcatcttc | gtccacatct | atcttttggg | tcaatgcagc | tgcacttgg | gtagacataa | 1020 |
| agtatgacac | cagtaaaaat | aaaacgatga | ctcattggat | ctccgaaaat | ggtgtcatag | 1080 |
| atgtagtcat | gtccctgggg | ccagatattc | caactatcat | tgcaaatttt | accgatttga | 1140 |
| ctggtagacc | cttttaccg | cccatttcct | ctatagggta | ccatcaatgt | agatggaatt | 1200 |
| ataatgatga | gatggacgtt | ctcacagtgg | actctcagat | ggatgctcat | atgattcctt | 1260 |
| acgattttat | ttggttggac | ttggagtata | cgaacgacaa | aaaatatttt | acttggaagc | 1320 |
| agcactcctt | tcccaatcca | aaaggctgt | tatccaaatt | aaaaaagttg | ggtagaaatc | 1380 |
| ttgtcgtact | aatcgatcct | catttaaaga | aagattatga | aatcagtgac | agggtaatta | 1440 |

-continued

```
atgaaaatgt agcagtcaag gatcacaatg gaaatgacta tgtaggtcat tgctggccag    1500
gtaattctat atggattgat accataagca aatatggcca aaagatttgg aagtccttt     1560 tcgaacggtt tatggatctg ccggctgatt taactaattt attcatttgg aatgatatga    1620
acgagccttc gattttcgat ggcccagaga ccacagctcc aaaagatttg attcacgaca    1680
attacattga ggaaagatcc gtccataaca tatatggtct atcagtgcat gaagctactt    1740
acgacgcaat aaaatcgatt tattcaccat ccgataagcg tcctttcctt ctaacaaggg    1800 cttttttttgc cggctctcaa cgtactgctg ccacatggac tggtgacaat gtggccaatt   1860
gggattactt aaagatttcc attcctatgg ttctgtcaaa caacattgct ggtatgccat    1920
ttataggagc cgacatagct ggctttgctg aggatcctac acctgaattg attgcacgtt    1980
ggtaccaagc gggcttatgg tacccatttt ttagagcaca cgcccatata gacaccaaga    2040
gaagagaacc atacttattc aatgaacctt tgaagtcgat agtacgtgat attatccaat    2100
tgagatattt cctgctacct accttataca ccatgtttca taaatcaagt gtcactggat    2160
ttccgataat gaatccaatg tttattgaac accctgaatt tgctgaattg tatcatatcg    2220
ataaccaatt ttactggagt aattcaggtc tattagtcaa acctgtcacg gagcctggtc    2280
aatcagaaac ggaaatggtt ttcccacccg gtatattcta tgaattcgca tctttacact    2340
cttttataaa caatggtact gatttgatag aaaagaatat ttctgcacca ttggataaaa    2400
ttccattatt tattgaaggc ggtcacatta tcactatgaa agataagtat agaagatctt    2460
caatgttaat gaaaacgat ccatatgtaa tagtttatagc ccctgatacc gagggacgag    2520
ccgttggaga tctttatgtt gatgatggag aaacttttgg ctaccaaaga ggtgagtacg    2580
tagaaactca gttcattttc gaaaacaata cctaaaaaaa tgttcgaagt catattcccg    2640
agaatttgac aggcattcac cacaatactt tgaggaatac caatattgaa aaaatcatta    2700
tcgcaaagaa taatttacaa cacaacataa cgttgaaaga cagtattaaa gtcaaaaaaa    2760
atggcgaaga aagttcattg ccgactagat cgtcatatga gaatgataat aagatcacca    2820
ttcttaacct atcgcttgac ataactgaag attgggaagt tattttttggg cccgaacaaa    2880 aactcatctc agaagaggat ctgaatagcg ccgtcgacca tcatcatcat catcattgag    2940 ttttagccctt agacatgact gttcctcagt tcaagttggg cacttacgag aagaccggtc    3000
ttgctagatt ctaatcaaga ggatgtcaga atgccatttg cctgagagat gcaggcttca    3060
tttttgatac tttttttattt gtaacctata tagtataggga tttttttttgt cattttgtt    3120 cttctcgtac gagcttgctc ctgatcagcc tatctcgcag ctgatgaata tcttgtggta    3180
ggggtttggg aaaatcattc gagtttgatg tttttcttgg tatttcccac tcctcttcag    3240
agtacagaag attaagtgag accttcgttt gtgcggatcc cccacacacc atagcttcaa    3300 aatgttttcta ctccttttt actcttccag attttctcgg actccgcgca tcgccgtacc    3360
acttcaaaac acccaagcac agcatactaa attttccctc tttcttcctc tagggtgtcg    3420
ttaattaccc gtactaaagg tttggaaaag aaaaagaga ccgcctcgtt tctttttctt     3480
cgtcgaaaaa ggcaataaaa attttttatca cgtttctttt tcttgaaatt ttttttttta    3540
gtttttttct ctttcagtga cctccattga tatttaagtt aataaacggt cttcaatttc    3600
tcaagtttca gtttcatttt tcttgttcta ttacaacttt ttttacttct tgttcattag    3660
aaagaaagca tagcaatcta atctaagggc ggtgttgaca attaatcatc ggcatagtat    3720
atcggcatag tataatacga caaggtgagg aactaaacca tggccaagtt gaccagtgcc    3780
gttccggtgc tcaccgcgcg cgacgtcgcc ggagcggtcg agttctggac cgaccggctc    3840
```

-continued

```
gggttctccc gggacttcgt ggaggacgac ttcgccggtg tggtccggga cgacgtgacc    3900
ctgttcatca gcgcggtcca ggaccaggtg gtgccggaca acaccctggc ctgggtgtgg    3960
gtgcgcggcc tggacgagct gtacgccgag tggtcggagg tcgtgtccac gaacttccgg    4020
gacgcctccg ggccggccat gaccgagatc ggcgagcagc cgtgggggcg ggagttcgcc    4080
ctgcgcgacc cggccggcaa ctgcgtgcac ttcgtggccg aggagcagga ctgacacgtc    4140
cgacggcggc ccacgggtcc caggcctcgg agatccgtcc cccttttcct tgtcgatat     4200 catgtaatta gttatgtcac gcttacattc acgccctccc cccacatccg ctctaaccga    4260
aaaggaagga gttagacaac ctgaagtcta ggtccctatt tattttttta tagttatgtt    4320
agtattaaga acgttattta tatttcaaat ttttcttttt tttctgtaca gacgcgtgta    4380
cgcatgtaac attatactga aaaccttgct tgagaaggtt ttgggacgct cgaaggcttt    4440
aatttgcaag ctggagacca acatgtgagc aaaaggccag caaaaggcca ggaaccgtaa    4500
aaaggccgcg ttgctggcgt ttttccatag gctccgcccc cctgacgagc atcacaaaaa    4560
tcgacgctca agtcagaggt ggcgaaaccc gacaggacta taaagatacc aggcgtttcc    4620
ccctggaagc tccctcgtgc gctctcctgt tccgaccctg ccgcttaccg gatacctgtc    4680
cgcctttctc ccttcgggaa gcgtggcgct ttctcaatgc tcacgctgta ggtatctcag    4740
ttcggtgtag gtcgttcgct ccaagctggg ctgtgtgcac gaaccccccg ttcagcccga    4800
ccgctgcgcc ttatccggta actatcgtct tgagtccaac ccggtaagac acgacttatc    4860
gccactggca gcagccactg gtaacaggat tagcagagcg aggtatgtag gcggtgctac    4920
agagttcttg aagtggtggc ctaactacgg ctacactaga aggacagtat ttggtatctg    4980
cgctctgctg aagccagtta ccttcggaaa agagttggt agctcttgat ccggcaaaca    5040
aaccaccgct ggtagcggtg ttttttttgt ttgcaagcag cagattacgc gcagaaaaaa    5100
aggatctcaa gaagatcctt tgatctttc tacgggtct gacgctcagt ggaacgaaaa     5160
ctcacgttaa gggattttgg tcatgcatga gatcagatct ttttgtaga aatgtcttgg     5220 tgtcctcgtc caatcaggta gccatctctg aaatatctgg ctccgttgca actccgaacg    5280
acctgctggc aacgtaaaat tctccggggt aaaacttaaa tgtggagtaa tggaaccaga    5340
aacgtctctt cccttctctc tccttccacc gcccgttacc gtcccctagga aattttactc    5400 tgctggagag cttcttctac ggccccttg cagcaatgct cttcccagca ttacgttgcg    5460
ggtaaaacgg aggtcgtgta cccgacctag cagcccaggg atggaaaagt cccggccgtc    5520
gctggcaata atagcgggcg gacgcatgtc atgagattat tggaaaccac cagaatcgaa    5580
tataaaaggc gaacaccttt cccaattttg gtttctcctg acccaaagac tttaaattta    5640
atttatttgt ccctatttca atcaattgaa caactatttc gaaacgagga attcacgtgg    5700
cccagccggc cgtctcggat cggtacc                                       5727
```

<210> SEQ ID NO 19
<211> LENGTH: 7236
<212> TYPE: DNA
<213> ORGANISM: Artificial Sequence
<220> FEATURE:
<223> OTHER INFORMATION: Description of Artificial Sequence:Sequence of plasmid pGAPADE1glsII.

<400> SEQUENCE: 19

```
tcgaccggct gcattaatga atcggccaac gcgcggggag aggcggtttg cgtattgggc      60
gctcttccgc ttcctcgctc actgactcgc tgcgctcggt cgttcggctg cggcgagcgg     120
```

-continued

```
tatcagctca ctcaaaggcg gtaatacggt tatccacaga atcaggggat aacgcaggaa    180
agaacatgtg agcaaaaggc cagcaaaagg ccaggaaccg taaaaaggcc gcgttgctgg    240
cgttttccca taggctccgc ccccctgacg agcatcacaa aaatcgacgc tcaagtcaga    300
ggtggcgaaa cccgacagga ctataaagat accaggcgtt tccccctgga agctccctcg    360
tgcgctctcc tgttccgacc ctgccgctta ccggatacct gtccgccttt ctcccttcgg    420
gaagcgtggc gctttctcat agctcacgct gtaggtatct cagttcggtg taggtcgttc    480
gctccaagct gggctgtgtg cacgaacccc ccgttcagcc cgaccgctgc gccttatccg    540
gtaactatcg tcttgagtcc aacccggtaa gacacgactt atcgccactg gcagcagcca    600
ctggtaacag gattagcaga gcgaggtatg taggcggtgc tacagagttc ttgaagtggt    660
ggcctaacta cggctacact agaaggacag tatttggtat ctgcgctctg ctgaagccag    720
ttaccttcgg aaaaagagtt ggtagctctt gatccggcaa acaaaccacc gctggtagcg    780
gtggtttttt tgtttgcaag cagcagatta cgcgcagaaa aaaggatctc aagaagatc    840
ctttgatctt ttctacgggg tctgacgctc agtggaacga aaactcacgt taagggattt    900
tggtcatgag attatcaaaa aggatcttca cctagatcct tttaaattaa aaatgaagtt    960
ttaaatcaat ctaaagtata tatgagtaaa cttggtctga cagttaccaa tgcttaatca   1020
gtgaggcacc tatctcagcg atctgtctat ttcgttcatc catagttgcc tgactccccg   1080
tcgtgtagat aactacgata cgggagggct taccatctgg ccccagtgct gcaatgatac   1140
cgcgagaccc acgctcaccg gctccagatt tatcagcaat aaaccagcca gccggaaggg   1200
ccgagcgcag aagtggtcct gcaactttat ccgcctccat ccagtctatt aattgttgcc   1260
gggaagctag agtaagtagt tcgccagtta atagtttgcg caacgttgtt gccattgcta   1320
caggcatcgt ggtgtcacgc tcgtcgtttg gtatggcttc attcagctcc ggttcccaac   1380
gatcaaggcg agttacatga tcccccatgt tgtgcaaaaa agcggttagc tccttcggtc   1440
ctccgatcgt tgtcagaagt aagttggccg cagtgttatc actcatggtt atggcagcac   1500
tgcataattc tcttactgtc atgccatccg taagatgctt ttctgtgact ggtgagtact   1560
caaccaagtc attctgagaa tagtgtatgc ggcgaccgag ttgctcttgc ccggcgtcaa   1620
tacgggataa taccgcgcca catagcagaa ctttaaaagt gctcatcatt ggaaaacgtt   1680
cttcggggcg aaaactctca aggatcttac cgctgttgag atccagttcg atgtaaccca   1740
ctcgtgcacc caactgatct tcagcatctt ttactttcac cagcgtttct gggtgagcaa   1800
aaacaggaag gcaaaatgcc gcaaaaaagg gaataagggc gacacggaaa tgttgaatac   1860
tcatactctt cctttttcaa tagctccaag gcaacaaatt gactactcag accgacattc   1920
attcgttatt gattttaaat caacgataaa cggaatggtt acttgaatga tttcacttta   1980
tgatcattgt ttactaatta cctaaatagg attttatatg gaattggaag aataagggaa   2040
atttcagatg tctgaaaaag gcgaggaggg tactaatcat tcaagcccat tcttgccag    2100
taattgcttc ataagcttca atatactttt ctttactctt gatagcaatt tctgcatcca   2160
tggctacgcc ctctttgcca ttcaatccgt tggccgtcaa ccaatctctg agaaactgct   2220
tatcgtaact ctcttgcgat ttacccactt ggtaagtctt ttgattccaa aatctagaag   2280
aatctggagt taaaacttca tctactagta ccaattcatt gttttcgtcc agtccaaatt   2340
cgaatttcgt atcagcaata atgatcccct tcaaagggc gaagttttttt gcagcagaat   2400
acaactcgac cgccttgaca gcgaccttct cacaaatgtc tttacctaca atctcagcag   2460
```

-continued

```
cttgttcaat agagatgttt tcatcgtgtt caccctgttc agctttcgtt gaaggtgtga    2520
aaatcggagt tggaaaggcg tcgctctctt gaaggttctc gttttcaacc ttgactccat    2580
ggacagtttt tgagttcttg tactctttcc atgcacttcc agtgatgtaa cctctgacaa    2640
tggcttccaa aggtatcagt ctgtgctttt ttactatcaa ggatcgtccc tctaattgag    2700
atttgtattt ttcttcagac agttttgatg gtagtaaagc aaagacttcc ttgtcattag    2760
aagcaaccaa atgattcttt atgtagggtg ccaaaaaatc aaaccagaaa actgagagct    2820
gagtcaaaat cttccccta tcaggaatac cgtttgtcat aatcacatcg taagcggaga    2880
tacggtcagt tgcgacgaac agcaagttgt tctcatcgac tgcataaatg tctctaacct    2940
ttcctttggc gattaaaggt aggattccgt ccagatcagt gttcacaatg gacatacttg    3000
gaaggataca gcaaagtgtg ttggaagcga tgacacatgg aaaggaattt ttcgagtttc    3060
ctagagtagt atattggggc ggtgaaagtt cagatgttta atgcttaata ctcttatact    3120
cttcaaagcg cccaagtgtt tctgccaacc tgactttttt ctgaataatg aatcgttcaa    3180
gtggagtatt taaaccatga ttaagttacg tgatttggca ctggataagg tcgaaaaata    3240
tccgtattca taaacgatta ttggtaaaag ttacaaaata ccactaatta cggagaagct    3300
tagtaacagt tatcatctct tggtcgatta acgcttacaa tttccattcg ccattcaggc    3360
tgcgcaactg ttgggaaggg cgatcggtgc gggcctcttc gctattacgc cagggcctcg    3420
aggcacaaac gaacgtctca cttaatcttc tgtactctga agaggagtgg gaaataccaa    3480
gaaaaacatc aaactcgaat gattttccca aaccccctacc acaagatatt catcagctgc    3540
gagataggct gatcaggagc aagctcgtac gagaagaaac aaaatgacaa aaaaaatcct    3600
atactatata ggttacaaat aaaaaagtat caaaaatgaa gcctgcatct ctcaggcaaa    3660
tggcattctg acatcctctt gattagaatc tagcaagacc ggtcttctcg taagtgccca    3720
acttgaactg aggaacagtc atgtctaagg ctaaaactca atgatgatga tgatgatggt    3780
cgacggcgct attcagatcc tcttctgaga tgagtttttg ttcgggccca aaaataactt    3840
cccaatcttc agttatgtca agcgataggt taagaatggt gatcttatta tcattctcat    3900
atgacgatct agtcggcaat gaactttctt cgccattttt tttgacttta atactgtctt    3960
tcaacgttat gttgtgttgt aaattattct ttgcgataat gatttttca atattggtat    4020 tcctcaaagt attgtggtga atgcctgtca aattctcggg aatatgactt cgaacatttt    4080
ttaaggtatt gttttcgaaa atgaactgag tttctacgta ctcacctctt tggtagccaa    4140
aagtttctcc atcatcaaca taaagatctc caacggctcg tccctcggta tcaggggcta    4200
taactattac atatggatcg ttttcatta acattgaaga tcttctatac ttatctttca    4260
tagtgataat gtgaccgcct tcaataaata atggaatttt atccaatggt gcagaaatat    4320
tcttttctat caaatcagta ccattgttta taaaagagtg taaagatgcg aattcataga    4380
atataccggg tgggaaaacc atttccgttt ctgattgacc aggctccgtg acaggtttga    4440
ctaatagacc tgaattactc cagtaaaatt ggttatcgat atgatacaat tcagcaaatt    4500
cagggtgttc aataaacatt ggattcatta tcggaaatcc agtgacactt gatttatgaa    4560
acatggtgta taggtaggt agcaggaaat atctcaattg gataatatca cgtactatcg    4620
acttcaaagg ttcattgaat aagtatggtt ctcttctctt ggtgtctata tgggcgtgtg    4680
ctctaaaaaa tgggtaccat aagcccgctt ggtaccaacg tgcaatcaat tcaggtgtag    4740
gatcctcagc aaagccagct atgtcggctc ctataaatgg cataccagca atgttgtttg    4800
acagaaccat aggaatggaa atctttaagt aatcccaatt ggccacattg tcaccagtcc    4860
```

-continued

```
atgtggcagc agtacgttga gagccggcaa aaaaagccct tgttagaagg aaaggacgct    4920
tatcggatgg tgaataaatc gattttattg cgtcgtaagt agcttcatgc actgatagac    4980
catatatgtt atggacggat cttcctcaa tgtaattgtc gtgaatcaaa tcttttggag     5040
ctgtggtctc tgggccatcg aaaatcgaag gctcgttcat atcattccaa atgaataaat    5100
tagttaaatc agccggcaga tccataaacc gttcgaaaaa ggacttccaa atcttttggc    5160
catatttgct tatggtatca atccatatag aattacctgg ccagcaatga cctacatagt    5220
catttccatt gtgatccttg actgctacat tttcattaat taccctgtca ctgatttcat    5280
aatctttctt taaatgagga tcgattagta cgacaagatt tctacccaac ttttttaatt    5340
tggataacag cctttttgga ttgggaaagg agtgctgctt ccaagtaaaa tattttttgt    5400
cgttcgtata ctccaagtcc aaccaaataa aatcgtaagg aatcatatga gcatccatct    5460
gagagtccac tgtgagaacg tccatctcat cattataatt ccatctacat tgatggtacc    5520
ctatagagga aatgggcggt aaaaagggtc taccagtcaa atcggtaaat ttgtcaatga    5580
tagttggaat atctgcccc agggacatga ctacatctat gacaccattt tcggagatcc     5640
aatgagtcat cgtttatttt ttactggtgt catactttat gtctacccaa gtgtcagctg    5700
cattgaccca aaagatagat gtggacgaag atgaaaacat gaatgggatc gaaccgtaca    5760
ttggttggct ggtaccgatg ttgtactcaa agacatcaac gttgaaaagc ctgtagggtt    5820
cctttccacc tgaagtgtcc atcagcctta gcgacgtcgc atgttccggt ataccgtaga    5880
cattagtaga acccatgaaa gagaaatcta gcgcaaccga ttcaggcccc aaaggcatag    5940
agtcatgctt tgaatacaag aaattgtcct taaacatgtt gaaagttgtt tcttctggca    6000
gcacgtgtgc gaagttttcc tgcttagttc tatgatgttc aatgttcagg aaattttgct    6060
cgtttacaat aagtttcagc gcattttgcc agtaaacttt caattgaaaa ggttcagcaa    6120
agatttctac ggatacatca ccgtttcgaa gatgaaatgt gtctgcagtg gagtttgaaa    6180
gtgacaaaaa tgaagatatt tcgaccagaa tgagttcac agtttgtttt tgcttaagga    6240
agtggaattg tggaatactg gtcctgttcg cctcctcttg aaatttcttg tcgaatgcgt    6300
acttccaggt ctcattgaac cgttgtgaag agatcaacaa accgctgctg ttggttggca    6360
ttctctcttt ctcatttata gtgaacctta ctgagtgatc ctgtaaaaaa gagagagaga    6420
atgggaactg aacggctata tcatcgccct ccaatcttgg tatagtttta attatggtag    6480
catgaagcac attctctaaa ggatcgtgtg caatagactc ggcgtccact ttgtaatagc    6540
agtgatgaga tttggcaata ttttctgcat aaaccctgtt tctatggcaa aacccagatt    6600
gcgcacactc ctttaataga tagtcggtaa acgcatgcga aaaagcggta aagaagacca    6660
attggcatac gagccatttc aaaaggacca tctcgaggta ccgatccgag acggccggct    6720
gggccacgtg aattcctcgt ttcgaaatag ttgttcaatt gattgaaata gggacaaata    6780
aattaaattt aaagtctttg ggtcaggaga aaccaaaatt gggaaaggtg ttcgccttt     6840 atattcgatt ctggtggttt ccaataatct catgacatgc gtccgcccgc tattattgcc    6900
agcgacggcc gggacttttc catccctggg ctgctaggtc gggtacacga cctccgtttt    6960
acccgcaacg taatgctggg aagagcattg ctgcaagggg gccgtagaag aagctctcca    7020
gcagagtaaa atttcctagg gacggtaacg ggcggtggaa ggagagagaa gggaagagac    7080
gtttctggtt ccattactcc acatttaagt tttaccccgg agaatttac gttgccagca     7140 ggtcgttcgg agttgcaacg gagccagata tttcagagat ggctacctga ttggacgagg    7200
```

-continued

| | |
|---|---|
| acaccaagac atttctacaa aaaagatctg atctca | 7236 |

<210> SEQ ID NO 20
<211> LENGTH: 6173
<212> TYPE: DNA
<213> ORGANISM: Artificial Sequence
<220> FEATURE:
<223> OTHER INFORMATION: Description of Artificial Sequence:Sequence of plasmid pPICZAGLSII.

<400> SEQUENCE: 20

| | |
|---|---|
| cgaacaaaaa ctcatctcag aagaggatct gaatagcgcc gtcgaccatc atcatcatca | 60 |
| tcattgagtt tgtagcctta gacatgactg ttcctcagtt caagttgggc acttacgaga | 120 |
| agaccggtct tgctagattc taatcaagag gatgtcagaa tgccatttgc ctgagagatg | 180 |
| caggcttcat ttttgatact tttttatttg taacctatat agtataggat tttttttgtc | 240 |
| attttgtttc ttctcgtacg agcttgctcc tgatcagcct atctcgcagc tgatgaatat | 300 |
| cttgtggtag gggtttggga aaatcattcg agtttgatgt ttttcttggt atttcccact | 360 |
| cctcttcaga gtacagaaga ttaagtgaga ccttcgtttg tgcggatccc ccacacacca | 420 |
| tagcttcaaa atgtttctac tccttttta ctcttccaga ttttctcgga ctccgcgcat | 480 |
| cgccgtacca cttcaaaaca cccaagcaca gcatactaaa ttttccctct ttcttcctct | 540 |
| agggtgtcgt taattacccg tactaaaggt ttggaaaaga aaaagagac cgcctcgttt | 600 |
| cttttttcttc gtcgaaaaag gcaataaaaa ttttttatcac gtttctttt cttgaaattt | 660 |
| ttttttttag ttttttttctc tttcagtgac ctccattgat atttaagtta ataaacggtc | 720 |
| ttcaatttct caagtttcag tttcatttt cttgttctat tacaacttt tttacttctt | 780 |
| gttcattaga aagaaagcat agcaatctaa tctaagggc ggtgttgaca attaatcatc | 840 |
| ggcatagtat atcggcatag tataatacga caaggtgagg aactaaacca tggccaagtt | 900 |
| gaccagtgcc gttccggtgc tcaccgcgcg cgacgtcgcc ggagcggtcg agttctggac | 960 |
| cgaccggctc gggttctccc gggacttcgt ggaggacgac ttcgccggtg tggtccggga | 1020 |
| cgacgtgacc ctgttcatca gcgcggtcca ggaccaggtg gtgccggaca cacccctggc | 1080 |
| ctgggtgtgg gtgcgcggcc tggacgagct gtacgccgag tggtcggagg tcgtgtccac | 1140 |
| gaacttccgg gacgcctccg ggccggccat gaccgagatc ggcgagcagc cgtgggggcg | 1200 |
| ggagttcgcc ctgcgcgacc cggccggcaa ctgcgtgcac ttcgtggccg aggagcagga | 1260 |
| ctgacacgtc cgacggcggc ccacgggtcc caggcctcgg agatccgtcc ccttttcct | 1320 |
| ttgtcgatat catgtaatta gttatgtcac gcttacattc acgccctccc cccacatccg | 1380 |
| ctctaaccga aaaggaagga gttagacaac ctgaagtcta ggtccctatt tatttttta | 1440 |
| tagttatgtt agtattaaga acgttattta tatttcaaat ttttctttt tttctgtaca | 1500 |
| gacgcgtgta cgcatgtaac attatactga aaaccttgct tgagaaggtt ttgggacgct | 1560 |
| cgaaggcttt aatttgcaag ctggagacca acatgtgagc aaaaggccag caaaaggcca | 1620 |
| ggaaccgtaa aaaggccgcg ttgctggcgt ttttccatag gctccgcccc cctgacgagc | 1680 |
| atcacaaaaa tcgacgctca agtcagaggt ggcgaaaccc gacaggacta taaagatacc | 1740 |
| aggcgtttcc ccctggaagc tccctcgtgc gctctcctgt tccgaccctg ccgcttaccg | 1800 |
| gatacctgtc cgcctttctc ccttcgggaa gcgtggcgct ttctcaatgc tcacgctgta | 1860 |
| ggtatctcag ttcggtgtag gtcgttcgct ccaagctggg ctgtgtgcac gaaccccccg | 1920 |
| ttcagcccga ccgctgcgcc ttatccggta actatcgtct tgagtccaac ccggtaagac | 1980 |

-continued

```
acgacttatc gccactggca gcagccactg gtaacaggat tagcagagcg aggtatgtag    2040
gcggtgctac agagttcttg aagtggtggc ctaactacgg ctacactaga aggacagtat    2100
ttggtatctg cgctctgctg aagccagtta ccttcggaaa aagagttggt agctcttgat    2160
ccggcaaaca aaccaccgct ggtagcggtg gttttttttgt ttgcaagcag cagattacgc    2220
gcagaaaaaa aggatctcaa gaagatcctt tgatcttttc tacggggtct gacgctcagt    2280
ggaacgaaaa ctcacgttaa gggattttgg tcatgagatc agatctaaca tccaaagacg    2340
aaaggttgaa tgaaaccttt ttgccatccg acatccacag gtccattctc acacataagt    2400
gccaaacgca acaggagggg atacactagc agcagaccgt tgcaaacgca ggacctccac    2460
tcctcttctc ctcaacaccc acttttgcca tcgaaaaacc agcccagtta ttgggcttga    2520
ttggagctcg ctcattccaa ttccttctat taggctacta acaccatgac tttattagcc    2580
tgtctatcct ggcccccctg gcgaggttca tgtttgttta tttccgaatg caacaagctc    2640
cgcattacac ccgaacatca ctccagatga gggcttctg agtgtggggt caaatagttt    2700
catgttcccc aaatggccca aaactgacag tttaaacgct gtcttggaac ctaatatgac    2760
aaaagcgtga tctcatccaa gatgaactaa gtttggttcg ttgaaatgct aacggccagt    2820
tggtcaaaaa gaaacttcca aaagtcggca taccgtttgt cttgtttggt attgattgac    2880
gaatgctcaa aaataatctc attaatgctt agcgcagtct ctctatcgct tctgaacccc    2940
ggtgcacctg tgccgaaacg caaatgggga acacccgct ttttggatga ttatgcattg    3000
tctccacatt gtatgcttcc aagattctgg tgggaatact gctgatagcc taacgttcat    3060
gatcaaaatt taactgttct aacccctact tgacagcaat atataaacag aaggaagctg    3120
ccctgtctta aacctttttt tttatcatca ttattagctt actttcataa ttgcgactgg    3180
ttccaattga caagcttttg attttaacga cttttaacga caacttgaga agatcaaaaa    3240
acaactaatt attcgaaacg aggaattcac gtggcccagc cggccgtctc ggatcggtac    3300
ctcgagatgg tccttttgaa atggctcgta tgccaattgg tcttctttac cgcttttttcg    3360 catgcgttta ccgactatct attaaagaag tgtgcgcaat ctgggttttg ccatagaaac    3420
agggtttatg cagaaaatat tgccaaatct catcactgct attacaaagt ggacgccgag    3480
tctattgcac acgatccttt agagaatgtg cttcatgcta ccataattaa aactatacca    3540
agattggagg gcgatgatat agccgttcag ttcccattct ctctctcttt tttacaggat    3600
cactcagtaa ggttcactat aaatgagaaa gagagaatgc caaccaacag cagcggtttg    3660
ttgatctctt cacaacggtt caatgagacc tggaagtacg cattcgacaa gaaatttcaa    3720
gaggaggcga acaggaccag tattccacaa ttccacttcc ttaagcaaaa acaaactgtg    3780
aactcattct ggtcgaaaat atcttcattt ttgtcacttt caaactccac tgcagacaca    3840
tttcatcttc gaaacggtga tgtatccgta gaaatctttg ctgaaccttt tcaattgaaa    3900
gtttactggc aaaatgcgct gaaacttatt gtaaacgagc aaaatttcct gaacattgaa    3960
catcatagaa ctaagcagga aaacttcgca cacgtgctgc cagaagaaac aactttcaac    4020
atgtttaagg acaatttctt gtattcaaag catgactcta tgcctttggg gcctgaatcg    4080
gttgcgctag atttctcttt catgggttct actaatgtct acggtatacc ggaacatgcg    4140
acgtcgctaa ggctgatgga cacttcaggt ggaaaggaac cctacaggct tttcaacgtt    4200
gatgtctttg agtacaacat cggtaccagc caaccaatgt acggttcgat cccattcatg    4260
ttttcatctt cgtccacatc tatctttttgg gtcaatgcag ctgacacttg ggtagacata    4320
aagtatgaca ccagtaaaaa taaaacgatg actcattgga tctccgaaaa tggtgtcata    4380
```

```
gatgtagtca tgtccctggg gccagatatt ccaactatca ttgacaaatt taccgatttg    4440
actggtagac ccttttttacc gcccatttcc tctataggt accatcaatg tagatggaat    4500
tataatgatg agatggacgt tctcacagtg gactctcaga tggatgctca tatgattcct    4560
tacgatttta tttggttgga cttggagtat acgaacgaca aaaatatttt tacttggaag    4620
cagcactcct ttcccaatcc aaaaaggctg ttatccaaat taaaaaagtt gggtagaaat    4680
cttgtcgtac taatcgatcc tcatttaaag aaagattatg aaatcagtga cagggtaatt    4740
aatgaaaatg tagcagtcaa ggatcacaat ggaaatgact atgtaggtca ttgctggcca    4800
ggtaattcta tatggattga taccataagc aaatatggcc aaaagatttg aagtcctttt    4860
ttcgaacggt ttatggatct gccggctgat ttaactaatt tattcatttg gaatgatatg    4920
aacgagcctt cgattttcga tggcccagag accacagctc caaaagatttt gattcacgac    4980 aattacattg aggaaagatc cgtccataac atatatggtc tatcagtgca tgaagctact    5040
tacgacgcaa taaaatcgat ttattcacca tccgataagc gtcctttcct tctaacaagg    5100 gcttttttttg ccggctctca acgtactgct gccacatgga ctggtgacaa tgtggccaat    5160
tgggattact taaagatttc cattcctatg gttctgtcaa acaacattgc tggtatgcca    5220
tttataggag ccgacatagc tggctttgct gaggatccta cacctgaatt gattgcacgt    5280
tggtaccaag cgggcttatg gtacccatttt tttagagcac acgcccatat agacaccaag    5340
agaagagaac catacttatt caatgaacct tgaagtcga tagtacgtga tattatccaa    5400
ttgagatatt tcctgctacc taccttatac accatgtttc ataaatcaag tgtcactgga    5460
tttccgataa tgaatccaat gtttattgaa caccctgaat ttgctgaatt gtatcatatc    5520
gataaccaat tttactggag taattcaggt ctattagtca aacctgtcac ggagcctggt    5580
caatcagaaa cggaaatggt tttcccaccc ggtatattct atgaattcgc atctttacac    5640
tcttttataa acaatggtac tgatttgata gaaaagaata tttctgcacc attggataaa    5700
attccattat ttattgaagg cggtcacatt atcactatga agataagta tagaagatct    5760 tcaatgttaa tgaaaaacga tccatatgta atagttatag cccctgatac cgagggacga    5820
gccgttggag atctttatgt tgatgatgga gaaacttttg gctaccaaag aggtgagtac    5880
gtagaaactc agttcatttt cgaaaacaat accttaaaaa atgttcgaag tcatattccc    5940
gagaatttga caggcattca ccacaatact ttgaggaata ccaatattga aaaaatcatt    6000
atcgcaaaga ataatttaca acacaacata acgttgaaag acagtattaa agtcaaaaaa    6060
aatggcgaag aaagttcatt gccgactaga tcgtcatatg agaatgataa taagatcacc    6120
attcttaacc tatcgcttga cataactgaa gattgggaag ttattttttgg gcc          6173

<210> SEQ ID NO 21
<211> LENGTH: 7639
<212> TYPE: DNA
<213> ORGANISM: Artificial Sequence
<220> FEATURE:
<223> OTHER INFORMATION: Description of Artificial Sequence:Sequence of
      plasmid pPICADE1glsII.

<400> SEQUENCE: 21
aaattcctcg tttcgaataa ttagttgttt tttgatcttc tcaagttgtc gttaaaagtc      60
gttaaaatca aagcttgtc aattggaacc agtcgcaatt atgaaagtaa gctaataatg     120
atgataaaaa aaaaggttta agacagggca gcttccttct gtttatatat tgctgtcaag    180 tagggttag aacagttaaa ttttgatcat gaacgttagg ctatcagcag tattcccacc    240
```

-continued

```
agaatcttgg aagcatacaa tgtggagaca atgcataatc atccaaaaag cgggtgtttc    300
cccatttgcg tttcggcaca ggtgcaccgg ggttcagaag cgatagagag actgcgctaa    360
gcattaatga gattattttt gagcattcgt caatcaatac caaacaagac aaacggtatg    420
ccgactttg  gaagtttctt tttgaccaac tggccgttag catttcaacg aaccaaactt    480
agttcatctt ggatgagatc acgcttttgt catattaggt tccaagacag cgtttaaact    540
gtcagttttg ggccatttgg ggaacatgaa actatttgac cccacactca gaaagccctc    600
atctggagtg atgttcgggt gtaatgcgga gcttgttgca ttcggaaata acaaacatg     660
aacctcgcca gggggggccag gatagacagg ctaataaagt catggtgtta gtagcctaat    720
agaaggaatt ggaatgagcg agctccaatc aagcccaata actgggctgg tttttcgatg    780
gcaaaagtgg gtgttgagga aagaggagt  ggaggtcctg cgtttgcaac ggtctgctgc    840
tagtgtatcc cctcctgttg cgtttggcac ttatgtgtga aatgga cct  gtggatgtcg    900
gatggcaaaa aggtttcatt caacctttcg tctttggatg ttgtcgaccg gctgcattaa    960
tgaatcggcc aacgcgcggg gagaggcggt ttgcgtattg ggcgctcttc cgcttcctcg   1020
ctcactgact cgctgcgctc ggtcgttcgg ctgcggcgag cggtatcagc tcactcaaag   1080
gcggtaatac ggttatccac agaatcaggg gataacgcag gaaagaacat gtgagcaaaa   1140
ggccagcaaa aggccaggaa ccgtaaaaag gccgcgttgc tggcgttttt ccataggctc   1200
cgcccccctg acgagcatca caaaaatcga cgctcaagtc agaggtggcg aaacccgaca   1260
ggactataaa gataccaggc gtttccccct ggaagctccc tcgtgcgctc tcctgttccg   1320
accctgccgc ttaccggata cctgtccgcc tttctccctt cgggaagcgt ggcgctttct   1380
catagctcac gctgtaggta tctcagttcg gtgtaggtcg ttcgctccaa gctgggctgt   1440
gtgcacgaac cccccgttca gcccgaccgc tgcgccttat ccggtaacta tcgtcttgag   1500
tccaacccgg taagacacga cttatcgcca ctggcagcag ccactggtaa caggattagc   1560
agagcgaggt atgtaggcgg tgctacagag ttcttgaagt ggtggcctaa ctacggctac   1620
actagaagga cagtatttgg tatctgcgct ctgctgaagc cagttacctt cggaaaaaga   1680
gttggtagct cttgatccgg caaacaaacc accgctggta gcggtggttt ttttgtttgc   1740
aagcagcaga ttacgcgcag aaaaaaagga tctcaagaag atcctttgat cttttctacg   1800
gggtctgacg ctcagtggaa cgaaaactca cgttaaggga ttttggtcat gagattatca   1860
aaaaggatct tcacctagat ccttttaaat taaaaatgaa gttttaaatc aatctaaagt   1920
atatatgagt aaacttggtc tgacagttac caatgcttaa tcagtgaggc acctatctca   1980
gcgatctgtc tatttcgttc atccatagtt gcctgactcc ccgtcgtgta taactacg    2040
atacgggagg gcttaccatc tggccccagt gctgcaatga taccgcgaga cccacgctca   2100
ccggctccag atttatcagc aataaaccag ccagccggaa gggccgagcg cagaagtggt   2160
cctgcaactt tatccgcctc catccagtct attaattgtt gccgggaagc tagagtaagt   2220
agttcgccag ttaatagttt cgcaacgtt  gttgccattg ctacaggcat cgtggtgtca   2280
cgctcgtcgt ttggtatggc ttcattcagc tccggttccc aacgatcaag gcgagttaca   2340
tgatccccca tgttgtgcaa aaaagcggtt agctccttcg gtcctccgat cgttgtcaga   2400
agtaagttgg ccgcagtgtt atcactcatg gttatggcag cactgcataa ttctcttact   2460
gtcatgccat ccgtaagatg cttttctgtg actggtgagt actcaaccaa gtcattctga   2520
gaatagtgta tgcggcgacc gagttgctct tgcccggcgt caatacggga taataccgcg   2580
```

```
ccacatagca gaactttaaa agtgctcatc attggaaaac gttcttcggg gcgaaaactc    2640
tcaaggatct taccgctgtt gagatccagt tcgatgtaac ccactcgtgc acccaactga    2700
tcttcagcat cttttacttt caccagcgtt tctgggtgag caaaaacagg aaggcaaaat    2760
gccgcaaaaa agggaataag ggcgacacgg aaatgttgaa tactcatact cttccttttt    2820
caatagctcc aagcaacaa attgactact cagaccgaca ttcattcgtt attgatttta    2880
aatcaacgat aaacggaatg gttacttgaa tgatttcact ttatgatcat tgtttactaa    2940
ttacctaaat aggattttat atggaattgg aagaataagg gaaatttcag atgtctgaaa    3000
aaggcgagga gggtactaat cattcaagcc catttcttgc cagtaattgc ttcataagct    3060
tcaatatact tttctttact cttgatagca atttctgcat ccatggctac gccctctttg    3120
ccattcaatc cgttggccgt caaccaatct ctgagaaact gcttatcgta actctcttgc    3180
gatttaccca cttggtaagt cttttgattc caaaatctag aagaatctgg agttaaaact    3240
tcatctacta gtaccaattc attgttttcg tccagtccaa attcgaattt cgtatcagca    3300
ataatgatcc ccttcaaaag ggcgaagttt tttgcagcag aatacaactc gaccgccttg    3360
acagcgacct tctcacaaat gtctttacct acaatctcag cagcttgttc aatagagatg    3420
ttttcatcgt gttcaccctg ttcagctttc gttgaaggtg tgaaaatcgg agttggaaag    3480
gcgtcgctct cttgaaggtt ctcgttttca accttgactc catggacagt ttttgagttc    3540
ttgtactctt tccatgcact tccagtgatg taacctctga caatggcttc caaaggtatc    3600
agtctgtgct tttttactat caaggatcgt ccctctaatt gagatttgta tttttcttca    3660
gacagttttg atggtagtaa agcaaagact tccttgtcat tagaagcaac caaatgattc    3720
tttatgtagg gtgccaaaaa atcaaaccag aaaactgaga gctgagtcaa aatctttccc    3780
ttatcaggaa taccgtttgt cataatcaca tcgtaagcgg agatacggtc agttgcgacg    3840
aacagcaagt tgttctcatc gactgcataa atgtctctaa cctttccttt ggcgattaaa    3900
ggtaggattc cgtccagatc agtgttcaca atggacatac ttggaaggat acagcaaagt    3960
gtgttggaag cgatgacaca tggaaaggaa ttttcgagt ttcctagagt agtatattgg    4020
ggcggtgaaa gttcagatgt ttaatgctta atactcttat actcttcaaa gcgcccaagt    4080
gtttctgcca acctgacttt tttctgaata atgaatcgtt caagtggagt atttaaacca    4140
tgattaagtt acgtgatttg gcactggata aggtcgaaaa atatccgtat tcataaacga    4200
ttattggtaa aagttacaaa ataccactaa ttacggagaa gcttagtaac agttatcatc    4260
tcttggtcga ttaacgctta caatttccat tcgccattca ggctgcgcaa ctgttgggaa    4320
gggcgatcgg tgcgggcctc ttcgctatta cgccagggcc tcgaggcaca acgaacgtc    4380 tcacttaatc ttctgtactc tgaagaggag tgggaaatac caagaaaaac atcaaactcg    4440
aatgattttc ccaaacccct accacaagat attcatcagc tgcgagatag gctgatcagg    4500
agcaagctcg tacgagaaga aacaaaatga caaaaaaaat cctatactat ataggttaca    4560
aataaaaaag tatcaaaaat gaagcctgca tctctcaggc aaatggcatt ctgacatcct    4620
cttgattaga atctagcaag accggtcttc tcgtaagtgc ccaacttgaa ctgaggaaca    4680
gtcatgtcta aggctacaaa ctcaatgatg atgatgatga tggtcgacgg cgctattcag    4740
atcctcttct gagatgagtt tttgttcggg cccaaaaata acttcccaat cttcagttat    4800
gtcaagcgat aggttaagaa tggtgatctt attatcattc tcatatgacg atctagtcgg    4860
caatgaactt tcttcgccat tttttttgac tttaatactg tctttcaacg ttatgttgtg    4920
ttgtaaatta ttctttgcga taatgatttt ttcaatattg gtattcctca aagtattgtg    4980
```

-continued

```
gtgaatgcct gtcaaattct cgggaatatg acttcgaaca ttttttaagg tattgttttc    5040
gaaaatgaac tgagtttcta cgtactcacc tctttggtag ccaaaagttt ctccatcatc    5100
aacataaaga tctccaacgg ctcgtccctc ggtatcaggg gctataacta ttacatatgg    5160 atcgttttc attaacattg aagatcttct atacttatct ttcatagtga taatgtgacc    5220
gccttcaata aataatggaa ttttatccaa tggtgcagaa atattctttt ctatcaaatc    5280
agtaccattg tttataaaag agtgtaaaga tgcgaattca tagaatatac cgggtgggaa    5340
aaccatttcc gtttctgatt gaccaggctc cgtgacaggg ttgactaata gacctgaatt    5400
actccagtaa aattggttat cgatatgata caattcagca aattcagggt gttcaataaa    5460
cattggattc attatcggaa atccagtgac acttgattta tgaaacatgg tgtataaggt    5520
aggtagcagg aaatatctca attggataat atcacgtact atcgacttca aaggttcatt    5580
gaataagtat ggttctcttc tcttggtgtc tatatgggcg tgtgctctaa aaaatgggta    5640
ccataagccc gcttggtacc aacgtgcaat caattcaggt gtaggatcct cagcaaagcc    5700
agctatgtcg gctcctataa atggcatacc agcaatgttg tttgacagaa ccataggaat    5760
ggaaatcttt aagtaatccc aattggccac attgtcacca gtccatgtgg cagcagtacg    5820
ttgagagccg gcaaaaaaag cccttgttag aaggaaagga cgcttatcgg atggtgaata    5880
aatcgatttt attgcgtcgt aagtagcttc atgcactgat agaccatata tgttatggac    5940
ggatctttcc tcaatgtaat tgtcgtgaat caaatctttt ggagctgtgg tctctgggcc    6000
atcgaaaatc gaaggctcgt tcatatcatt ccaaatgaat aaattagtta aatcagccgg    6060
cagatccata aaccgttcga aaaggactt ccaaatctttt tggccatatt tgcttatggt    6120
atcaatccat atagaattac ctggccagca atgacctaca tagtcatttc cattgtgatc    6180
cttgactgct acattttcat taattaccct gtcactgatt tcataatctt tctttaaatg    6240
aggatcgatt agtacgacaa gatttctacc caacttttt aatttggata acagccttt    6300 tggattggga aaggagtgct gcttccaagt aaaatatttt ttgtcgttcg tatactccaa    6360
gtccaaccaa ataaaatcgt aaggaatcat atgagcatcc atctgagagt ccactgtgag    6420
aacgtccatc tcatcattat aattccatct acattgatgg taccctatag aggaaatggg    6480
cggtaaaaag ggtctaccag tcaaatcggt aaatttgtca atgatagttg gaatatctgg    6540
ccccagggac atgactacat ctatgacacc attttcggag atccaatgag tcatcgtttt    6600
atttttactg gtgtcatact ttatgtctac ccaagtgtca gctgcattga cccaaaagat    6660
agatgtggac gaagatgaaa acatgaatgg gatcgaaccg tacattggtt ggctggtacc    6720
gatgttgtac tcaaagacat caacgttgaa aagcctgtag ggttcctttc cacctgaagt    6780
gtccatcagc cttagcgacg tcgcatgttc cggtataccg tagacattag tagaacccat    6840
gaaagagaaa tctagcgcaa ccgattcagg ccccaaaggc atagagtcat gctttgaata    6900
caagaaattg tccttaaaca tgttgaaagt tgtttcttct ggcagcacgt gtgcgaagtt    6960
ttcctgctta gttctatgat gttcaatgtt caggaaattt tgctcgttta caataagttt    7020
cagcgcattt tgccagtaaa ctttcaattg aaaaggttca gcaaagattt ctacggatac    7080
atcaccgttt cgaagatgaa atgtgtctgc agtggagttt gaaagtgaca aaaatgaaga    7140
tattttcgac cagaatgagt tcacagtttg tttttgctta aggaagtgga attgtggaat    7200
actggtcctg ttcgcctcct cttgaaattt cttgtcgaat gcgtacttcc aggtctcatt    7260
gaaccgttgt gaagagatca acaaaccgct gctgttggtt ggcattctct ctttctcatt    7320
```

```
tatagtgaac cttactgagt gatcctgtaa aaaagagaga gagaatggga actgaacggc    7380
tatatcatcg ccctccaatc ttggtatagt tttaattatg gtagcatgaa gcacattctc    7440
taaaggatcg tgtgcaatag actcggcgtc cactttgtaa tagcagtgat gagatttggc    7500
aatattttct gcataaaccc tgtttctatg gcaaaaccca gattgcgcac acttctttaa    7560
tagatagtcg gtaaacgcat gcgaaaaagc ggtaaagaag accaattggc atacgagcca    7620
tttcaaaagg accatctcg                                                  7639
```

<210> SEQ ID NO 22
<211> LENGTH: 5742
<212> TYPE: DNA
<213> ORGANISM: Artificial Sequence
<220> FEATURE:
<223> OTHER INFORMATION: Description of Artificial Sequence:Sequence of plasmid pYPTIZAGLSII.

<400> SEQUENCE: 22

```
cgaacaaaaa ctcatctcag aagaggatct gaatagcgcc gtcgaccatc atcatcatca      60
tcattgagtt tgtagcctta gacatgactg ttcctcagtt caagttgggc acttacgaga     120
agaccggtct tgctagattc taatcaagag gatgtcagaa tgccatttgc ctgagagatg     180
caggcttcat ttttgatact tttttatttg taacctatat agtataggat tttttttgtc     240
attttgtttc ttctcgtacg agcttgctcc tgatcagcct atctcgcagc tgatgaatat     300
cttgtggtag gggtttggga aaatcattcg agtttgatgt ttttcttggt atttcccact     360
cctcttcaga gtacagaaga ttaagtgaga ccttcgtttg tgcggatccc ccacacacca     420
tagcttcaaa atgtttctac tccttttta ctcttccaga ttttctcgga ctccgcgcat      480
cgccgtacca cttcaaaaca cccaagcaca gcatactaaa ttttccctct tcttcctct      540 agggtgtcgt taattacccg tactaaaggt ttggaaaaga aaaagagac cgcctcgttt      600 ctttttcttc gtcgaaaaag gcaataaaaa tttttatcac gtttctttt cttgaaattt      660 tttttttag ttttttttctc tttcagtgac ctccattgat atttaagtta ataaacggtc     720
ttcaatttct caagtttcag tttcattttt cttgttctat tacaactttt tttacttctt     780
gttcattaga aagaaagcat agcaatctaa tctaagggc ggtgttgaca attaatcatc      840
ggcatagtat atcggcatag tataatacga caaggtgagg aactaaacca tggccaagtt    900
gaccagtgcc gttccggtgc tcaccgcgcg cgacgtcgcc ggagcggtcg agttctggac    960
cgaccggctc gggttctccc gggacttcgt ggaggacgac ttcgccggtg tggtccggga    1020
cgacgtgacc ctgttcatca gcgcggtcca ggaccaggtg gtgccggaca caccctggc    1080 ctgggtgtgg gtgcgcggcc tggacgagct gtacgccgag tggtcggagg tcgtgtccac    1140
gaacttccgg gacgcctccg ggccggccat gaccgagatc ggcgagcagc gtgggggcg    1200 ggagttcgcc ctgcgcgacc cggccggcaa ctgcgtgcac ttcgtggccg aggagcagga    1260
ctgacacgtc cgacggcggc ccacgggtcc caggcctcgg agatccgtcc ccttttcct    1320 ttgtcgatat catgtaatta gttatgtcac gcttacattc acgccctccc ccacatccg    1380 ctctaaccga aaggaagga gttagacaac ctgaagtcta ggtccctatt tatttttta    1440 tagttatgtt agtattaaga acgttattta tatttcaaat ttttcttttt tttctgtaca    1500
gacgcgtgta cgcatgtaac attatactga aaaccttgct tgagaaggtt ttgggacgct    1560
cgaaggcttt aatttgcaag ctggagacca acatgtgagc aaaaggccag caaaaggcca    1620
ggaaccgtaa aaaggccgcg ttgctggcgt ttttccatag gctccgcccc cctgacgagc    1680
```

```
atcacaaaaa tcgacgctca agtcagaggt ggcgaaaccc gacaggacta taaagatacc    1740
aggcgttttc ccctggaagc tccctcgtgc gctctcctgt tccgaccctg ccgcttaccg    1800 gataccgtgtc cgccttctc ccttcgggaa gcgtggcgct ttctcaatgc tcacgctgta    1860
ggtatctcag ttcggtgtag gtcgttcgct ccaagctggg ctgtgtgcac gaaccccccg    1920
ttcagcccga ccgctgcgcc ttatccggta actatcgtct tgagtccaac ccggtaagac    1980
acgacttatc gccactggca gcagccactg gtaacaggat tagcagagcg aggtatgtag    2040
gcggtgctac agagttcttg aagtggtggc ctaactacgg ctacactaga aggacagtat    2100
ttggtatctg cgctctgctg aagccagtta ccttcggaaa aagagttggt agctcttgat    2160
ccggcaaaca aaccaccgct ggtagcggtg gtttttttgt ttgcaagcag cagattacgc    2220
gcagaaaaaa aggatctcaa gaagatcctt tgatctttc tacggggtct gacgctcagt    2280
ggaacgaaaa ctcacgttaa gggattttgg tcatgagatc agatctatga tgagtcacaa    2340
tctgcttcca cagacgagta caaggacagg caaaaggaat tggaagaagt tgctaaccca    2400
ataatgagca agttctatgg agctgctggt ggagctcctg gtggagctcc tggtggcttc    2460
cctggaggtt tccctggcgg agctggcgca gctggcggtg ccccaggtgg tgctgcccca    2520
ggcggagaca gcggaccaac cgtggaagaa gtcgattaag caattcaacg gataaattct    2580
ggttaatata tataacgtga ataggaaatt aaggaaattt tggatctaat aatgtgctgt    2640
atgccgacat cggcatcgt agattgtata gtatcgctga cactataata agccagccaa    2700 aaccctaaa ccagttgccc tccactaatt agtgtactac ccaatcttgc ctcttcgggt    2760 gtctttata aggacagatt cacaagctct tgttgcccaa tacacacata cacacagaga    2820
taatagcagt cgaattcacg tggcccagcc ggccgtctcg gatcggtacc tcgagatggt    2880 cctttgaaa tggctcgtat gccaattggt cttctttacc gcttttcgc atgcgtttac    2940 cgactatcta ttaaagaagt gtgcgcaatc tgggttttgc catagaaaca gggtttatgc    3000
agaaaatatt gccaaatctc atcactgcta ttacaaagtg gacgccgagt ctattgcaca    3060 cgatcccttta gagaatgtgc ttcatgctac cataattaaa actataccaa gattggaggg    3120
cgatgatata gccgttcagt tcccattctc tctctctttt ttacaggatc actcagtaag    3180
gttcactata aatgagaaag agagaatgcc aaccaacagc agcggtttgt tgatctcttc    3240
acaacggttc aatgagacct ggaagtacgc attcgacaag aaatttcaag aggaggcgaa    3300
caggaccagt attccacaat tccacttcct taagcaaaaa caaactgtga actcattctg    3360
gtcgaaaata tcttcatttt tgtcactttc aaactccact gcagacacat ttcatcttcg    3420
aaacggtgat gtatccgtag aaatctttgc tgaacctttt caattgaaag tttactggca    3480
aaatgcgctg aaacttattg taaacgagca aaatttcctg aacattgaac atcatagaac    3540
taagcaggaa aacttcgcac acgtgctgcc agaagaaaca actttcaaca tgtttaagga    3600
caatttcttg tattcaaagc atgactctat gcctttgggg cctgaatcgg ttgcgctaga    3660
tttctctttc atgggttcta ctaatgtcta cggtataccg gaacatgcga cgtcgctaag    3720
gctgatggac acttcaggtg gaaaggaacc ctacaggctt ttcaacgttg atgtctttga    3780
gtacaacatc ggtaccagcc aaccaatgta cggttcgatc ccattcatgt tttcatcttc    3840
gtccacatct atcttttggg tcaatgcagc tgacacttgg gtagacataa agtatgacac    3900
cagtaaaaat aaaacgatga ctcattggat ctccgaaaat ggtgtcatag atgtagtcat    3960
gtccctgggg ccagatattc caactatcat tgacaaattt accgatttga ctggtagacc    4020
ctttttaccg cccatttcct ctatagggta ccatcaatgt agatggaatt ataatgatga    4080
```

-continued

```
gatggacgtt ctcacagtgg actctcagat ggatgctcat atgattcctt acgattttat    4140
ttggttggac ttggagtata cgaacgacaa aaatatttt acttggaagc agcactcctt     4200
tcccaatcca aaaggctgt tatccaaatt aaaaagttg ggtagaaatc ttgtcgtact      4260
aatcgatcct catttaaaga aagattatga aatcagtgac agggtaatta atgaaaatgt    4320
agcagtcaag gatcacaatg gaaatgacta tgtaggtcat tgctggccag gtaattctat   4380
atggattgat accataagca aatatggcca aaagatttgg aagtccttt tcgaacggtt    4440
tatgatctg ccggctgatt taactaattt attcatttgg aatgatatga acgagccttc    4500
gattttcgat ggcccagaga ccacagctcc aaaagatttg attcacgaca attacattga   4560
ggaaagatcc gtccataaca tatatggtct atcagtgcat gaagctactt acgacgcaat   4620
aaaatcgatt tattcaccat ccgataagcg tcctttcctt ctaacaaggg cttttttgc    4680
cggctctcaa cgtactgctg ccacatggac tggtgacaat gtggccaatt gggattactt   4740
aaagatttcc attcctatgg ttctgtcaaa caacattgct ggtatgccat ttataggagc   4800
cgacatagct ggctttgctg aggatcctac acctgaattg attgcacgtt ggtaccaagc   4860
gggcttatgg tacccatttt ttagagcaca cgcccatata gacaccaaga aagagaacc    4920
atacttattc aatgaaccttt tgaagtcgat agtacgtgat attatccaat tgagatattt   4980
cctgctacct accttataca ccatgtttca taaatcaagt gtcactggat ttccgataat    5040
gaatccaatg tttattgaac ccctgaatt tgctgaattg tatcatatcg ataaccaatt     5100
ttactggagt aattcaggtc tattagtcaa acctgtcacg gagcctggtc aatcagaaac    5160
ggaaatggtt ttcccacccg gtatattcta tgaattcgca tctttacact cttttataaa   5220
caatggtact gatttgatag aaaagaatat ttctgcacca ttggataaaa ttccattatt    5280
tattgaaggc ggtcacatta tcactatgaa agataagtat agaagatctt caatgttaat   5340
gaaaaacgat ccatatgtaa tagttatagc ccctgatacc gagggacgag ccgttggaga    5400
tctttatgtt gatgatggag aaacttttgg ctaccaaaga ggtgagtacg tagaaactca    5460
gttcattttc gaaaacaata ccttaaaaaa tgttcgaagt catattcccg agaatttgac    5520
aggcattcac cacaatactt tgaggaatac caatattgaa aaaatcatta tcgcaaagaa   5580
taatttacaa cacaacataa cgttgaaaga cagtattaaa gtcaaaaaaa atggcgaaga   5640
aagttcattg ccgactagat cgtcatatga gaatgataat aagatcacca ttcttaaccct   5700
atcgcttgac ataactgaag attgggaagt tatttttggg cc                       5742
```

<210> SEQ ID NO 23
<211> LENGTH: 7256
<212> TYPE: DNA
<213> ORGANISM: Artificial Sequence
<220> FEATURE:
<223> OTHER INFORMATION: Description of Artificial Sequence:Sequence of
      plasmid pYPT1ADE1glsII.

<400> SEQUENCE: 23

```
gtcgaccggc tgcattaatg aatcggccaa cgcgcgggga gaggcggttt gcgtattggg     60
cgctcttccg cttcctcgct cactgactcg ctgcgctcgg tcgttcggct gcggcgagcg    120
gtatcagctc actcaaaggc ggtaatacgg ttatccacag aatcagggga taacgcagga   180
agaacatgt gagcaaaagg ccagcaaaag gccaggaacc gtaaaaaggc cgcgttgctg    240
gcgtttttcc ataggctccg ccccctgac gagcatcaca aaaatcgacg ctcaagtcag    300
aggtggcgaa acccgacagg actataaaga taccaggcgt ttccccctgg aagctccctc   360
```

-continued

| | |
|---|---|
| gtgcgctctc ctgttccgac cctgccgctt accggatacc tgtccgcctt tctcccttcg | 420 |
| ggaagcgtgg cgctttctca tagctcacgc tgtaggtatc tcagttcggt gtaggtcgtt | 480 |
| cgctccaagc tgggctgtgt gcacgaaccc cccgttcagc ccgaccgctg cgccttatcc | 540 |
| ggtaactatc gtcttgagtc caacccggta agacacgact tatcgccact ggcagcagcc | 600 |
| actggtaaca ggattagcag agcgaggtat gtaggcggtg ctacagagtt cttgaagtgg | 660 |
| tggcctaact acggctacac tagaaggaca gtatttggta tctgcgctct gctgaagcca | 720 |
| gttaccttcg gaaaaagagt tggtagctct tgatccggca acaaaccac cgctggtagc | 780 |
| ggtggttttt ttgtttgcaa gcagcagatt acgcgcagaa aaaaggatc tcaagaagat | 840 |
| cctttgatct tttctacggg gtctgacgct cagtggaacg aaaactcacg ttaagggatt | 900 |
| ttggtcatga gattatcaaa aaggatcttc acctagatcc ttttaaatta aaaatgaagt | 960 |
| tttaaatcaa tctaaagtat atatgagtaa acttggtctg acagttacca atgcttaatc | 1020 |
| agtgaggcac ctatctcagc gatctgtcta tttcgttcat ccatagttgc ctgactcccc | 1080 |
| gtcgtgtaga taactacgat acgggagggc ttaccatctg gccccagtgc tgcaatgata | 1140 |
| ccgcgagacc cacgctcacc ggctccagat ttatcagcaa taaaccagcc agccggaagg | 1200 |
| gccgagcgca gaagtggtcc tgcaacttta tccgcctcca tccagtctat taattgttgc | 1260 |
| cgggaagcta gagtaagtag ttcgccagtt aatagtttgc gcaacgttgt tgccattgct | 1320 |
| acaggcatcg tggtgtcacg ctcgtcgttt ggtatggctt cattcagctc cggttcccaa | 1380 |
| cgatcaaggc gagttacatg atcccccatg ttgtgcaaaa aagcggttag ctccttcggt | 1440 |
| cctccgatcg ttgtcagaag taagttggcc gcagtgttat cactcatggt tatggcagca | 1500 |
| ctgcataatt ctcttactgt catgccatcc gtaagatgct tttctgtgac tggtgagtac | 1560 |
| tcaaccaagt cattctgaga atagtgtatg cggcgaccga gttgctcttg cccggcgtca | 1620 |
| atacgggata taccgcgcc acatagcaga actttaaaag tgctcatcat ggaaaacgt | 1680 |
| tcttcgggc gaaaactctc aaggatctta ccgctgttga atccagttc gatgtaaccc | 1740 |
| actcgtgcac ccaactgatc ttcagcatct tttactttca ccagcgtttc tgggtgagca | 1800 |
| aaaacaggaa ggcaaaatgc cgcaaaaaag ggaataaggg cgacacggaa atgttgaata | 1860 |
| ctcatactct tccttttca atagctccaa ggcaacaaat tgactactca gaccgacatt | 1920 |
| cattcgttat tgatttttaaa tcaacgataa acggaatggt tacttgaatg atttcacttt | 1980 |
| atgatcattg tttactaatt acctaaatag gattttatat ggaattggaa gaataaggga | 2040 |
| aatttcagat gtctgaaaaa ggcgaggagg gtactaatca ttcaagccca tttcttgcca | 2100 |
| gtaattgctt cataagcttc aatatacttt tctttactct tgatagcaat ttctgcatcc | 2160 |
| atggctacgc cctctttgcc attcaatccg ttggccgtca accaatctct gagaaactgc | 2220 |
| ttatcgtaac tctcttgcga tttacccact tggtaagtct tttgattcca aaatctagaa | 2280 |
| gaatctggag ttaaaacttc atctactagt accaattcat tgttttcgtc cagtccaaat | 2340 |
| tcgaatttcg tatcagcaat aatgatcccc ttcaaagggg cgaagttttt tgcagcagaa | 2400 |
| tacaactcga ccgccttgac agcgaccttc tcacaaatgt ctttacctac aatctcagca | 2460 |
| gcttgttcaa tagagatgtt ttcatcgtgt tcaccctgtt cagctttcgt tgaaggtgtg | 2520 |
| aaaatcggag ttggaaaggc gtcgctctct tgaaggttct cgttttcaac cttgactcca | 2580 |
| tggacagttt ttgagttctt gtactctttc catgcacttc cagtgatgta acctctgaca | 2640 |
| atggcttcca aaggtatcag tctgtgcttt tttactatca aggatcgtcc ctctaattga | 2700 |

```
gatttgtatt tttcttcaga cagttttgat ggtagtaaag caaagacttc cttgtcatta    2760
gaagcaacca aatgattctt tatgtagggt gccaaaaaat caaaccagaa aactgagagc    2820
tgagtcaaaa tctttccctt atcaggaata ccgtttgtca taatcacatc gtaagcggag    2880
atacggtcag ttgcgacgaa cagcaagttg ttctcatcga ctgcataaat gtctctaacc    2940
tttcctttgg cgattaaagg taggattccg tccagatcag tgttcacaat ggacatactt    3000
ggaaggatac agcaaagtgt gttggaagcg atgacacatg gaaaggaatt tttcgagttt    3060
cctagagtag tatattgggg cggtgaaagt tcagatgttt aatgcttaat actcttatac    3120
tcttcaaagc gcccaagtgt ttctgccaac ctgacttttt tctgaataat gaatcgttca    3180
agtggagtat ttaaaccatg attaagttac gtgatttggc actggataag gtcgaaaaat    3240
atccgtattc ataaacgatt attggtaaaa gttacaaaat accactaatt acggagaagc    3300
ttagtaacag ttatcatctc ttggtcgatt aacgcttaca atttccattc gccattcagg    3360
ctgcgcaact gttgggaagg gcgatcggtg cgggcctctt cgctattacg ccagggcctc    3420
gaggcacaaa cgaacgtctc acttaatctt ctgtactctg aagaggagtg ggaaatacca    3480
agaaaaacat caaactcgaa tgattttccc aaacccctac cacaagatat tcatcagctg    3540
cgagataggc tgatcaggag caagctcgta cgagaagaaa caaaatgaca aaaaaaatcc    3600
tatactatat aggttacaaa taaaaaagta tcaaaaatga agcctgcatc tctcaggcaa    3660
atggcattct gacatcctct tgattagaat ctagcaagac cggtcttctc gtaagtgccc    3720
aacttgaact gaggaacagt catgtctaag gctacaaact caatgatgat gatgatgatg    3780
gtcgacggcg ctattcagat cctcttctga gatgagtttt tgttcgggcc caaaaataac    3840
ttcccaatct tcagttatgt caagcgatag gttaagaatg gtgatcttat tatcattctc    3900
atatgacgat ctagtcggca atgaactttc ttcgccattt ttttgactt taatactgtc     3960 tttcaacgtt atgttgtgtt gtaaattatt ctttgcgata atgatttttt caatattggt    4020
attcctcaaa gtattgtggt gaatgcctgt caaattctcg ggaatatgac ttcgaacatt    4080
ttttaaggta ttgttttcga aaatgaactg agtttctacg tactcacctc tttggtagcc    4140
aaaagtttct ccatcatcaa cataaagatc tccaacggct cgtccctcgg tatcaggggc    4200
tataactatt acatatggat cgttttttcat taacattgaa gatcttctat acttatcttt    4260
catagtgata atgtgaccgc cttcaataaa taatggaatt ttatccaatg gtgcagaaat    4320
attcttttct atcaaatcag taccattgtt tataaaagag tgtaaagatg cgaattcata    4380
gaatataccg ggtgggaaaa ccatttccgt ttctgattga ccaggctccg tgacaggttt    4440
gactaataga cctgaattac tccagtaaaa ttggttatcg atatgataca attcagcaaa    4500
ttcagggtgt tcaataaaca ttggattcat tatcggaaat ccagtgacac ttgatttatg    4560
aaacatggtg tataaggtag gtagcaggaa atatctcaat tggataatat cacgtactat    4620
cgacttcaaa ggttcattga ataagtatgg ttctcttctc ttggtgtcta tatgggcgtg    4680
tgctctaaaa aatgggtacc ataagcccgc ttggtaccaa cgtgcaatca attcaggtgt    4740
aggatcctca gcaaagccag ctatgtcggc tcctataaat ggcataccag caatgttgtt    4800
tgacagaacc ataggaatgg aaatctttaa gtaatcccaa ttggccacat tgtcaccagt    4860
ccatgtggca gcagtacgtt gagagccggc aaaaaaagcc cttgttagaa ggaaaggacg    4920
cttatcggat ggtgaataaa tcgattttat tgcgtcgtaa gtagcttcat gcactgatag    4980
accatatatg ttatggacgg atcttttcctc aatgtaattg tcgtgaatca aatcttttgg    5040
agctgtggtc tctgggccat cgaaaatcga aggctcgttc atatcattcc aaatgaataa    5100
```

```
attagttaaa tcagccggca gatccataaa ccgttcgaaa aaggacttcc aaatcttttg    5160
gccatatttg cttatggtat caatccatat agaattacct ggccagcaat gacctacata    5220
gtcatttcca ttgtgatcct tgactgctac attttcatta attaccctgt cactgatttc    5280
ataatctttc tttaaatgag gatcgattag tacgacaaga tttctaccca acttttttaa    5340
tttggataac agccttttg gattgggaaa ggagtgctgc ttccaagtaa aatatttttt     5400
gtcgttcgta tactccaagt ccaaccaaat aaaatcgtaa ggaatcatat gagcatccat    5460
ctgagagtcc actgtgagaa cgtccatctc atcattataa ttccatctac attgatggta    5520
ccctatagag gaaatgggcg gtaaaaaggg tctaccagtc aaatcggtaa atttgtcaat    5580
gatagttgga atatctggcc ccagggacat gactacatct atgacaccat tttcggagat    5640
ccaatgagtc atcgttttat ttttactggt gtcatacttt atgtctaccc aagtgtcagc    5700
tgcattgacc caaagatag atgtggacga agatgaaaac atgaatggga tcgaaccgta    5760
cattggttgg ctggtaccga tgttgtactc aaagacatca acgttgaaaa gcctgtaggg    5820
ttcctttcca cctgaagtgt ccatcagcct tagcgacgtc gcatgttccg gtataccgta    5880
gacattagta gaacccatga aagagaaatc tagcgcaacc gattcaggcc ccaaaggcat    5940
agagtcatgc tttgaataca agaaattgtc cttaaacatg ttgaaagttg tttcttctgg    6000
cagcacgtgt gcgaagtttt cctgcttagt tctatgatgt tcaatgttca ggaaattttg    6060
ctcgtttaca ataagtttca gcgcattttg ccagtaaact ttcaattgaa aaggttcagc    6120
aaagatttct acggatacat caccgtttcg aagatgaaat gtgtctgcag tggagtttga    6180
aagtgacaaa aatgaagata ttttcgacca gaatgagttc acagtttgtt tttgcttaag    6240
gaagtggaat tgtggaatac tggtcctgtt cgcctcctct tgaaatttct tgtcgaatgc    6300
gtacttccag gtctcattga accgttgtga agagatcaac aaaccgctgc tgttggttgg    6360
cattctctct ttctcattta tagtgaacct tactgagtga tcctgtaaaa aagagagaga    6420
gaatgggaac tgaacggcta tatcatcgcc ctccaatctt ggtatagttt taattatggt    6480
agcatgaagc acattctcta aaggatcgtg tgcaatagac tcggcgtcca ctttgtaata    6540
gcagtgatga gatttggcaa tattttctgc ataaaccctg tttctatggc aaaacccaga    6600
ttgcgcacac ttcttaaata gatagtcggt aaacgcatgc gaaaagcgg taagaagac     6660 caattggcat acgagccatt tcaaaaggac catctcgagg taccgatccg agacggccgg    6720
ctgggccacg tgaattcgac tgctattatc tctgtgtgta tgtgtgtatt gggcaacaag    6780
agcttgtgaa tctgtcctta taaaagacac ccgaagaggc aagattgggt agtacactaa    6840
ttagtggagg gcaactggtt tagggttttt ggctggctta ttatagtgtc agcgatacta    6900
tacaatctac gatgcccgat gtcggcatac agcacattat tagatccaaa atttccttaa    6960
tttcctattc acgttatata tattaaccag aatttatccg ttgaattgct taatcgactt    7020
cttccacggt tggtccgctg tctccgcctg gggcagcacc acctggggca ccgccagctg    7080
cgccagctcc gccagggaaa cctccaggga agccaccagg agctccacca ggagctccac    7140
cagcagctcc atagaacttg ctcattattg ggttagcaac ttcttccaat tcctttgcc    7200 tgtccttgta ctcgtctgtg gaagcagatt gtgactcatc atagatctga tctcat        7256
```

<210> SEQ ID NO 24
<211> LENGTH: 5721
<212> TYPE: DNA
<213> ORGANISM: Artificial Sequence
<220> FEATURE:

-continued

<223> OTHER INFORMATION: Description of Artificial Sequence:Sequence of
      plasmid pGAPZAglsIIHDEL.

<400> SEQUENCE: 24

| | | | | | |
|---|---|---|---|---|---|
| tcgagatggt | cctttttgaaa | tggctcgtat | gccaattggt | cttctttacc | gcttttcgc | 60 |
| atgcgtttac | cgactatcta | ttaaagaagt | gtgcgcaatc | tgggttttgc | catagaaaca | 120 |
| gggtttatgc | agaaaatatt | gccaaatctc | atcactgcta | ttacaaagtg | gacgccgagt | 180 |
| ctattgcaca | cgatccttta | gagaatgtgc | ttcatgctac | cataattaaa | actataccaa | 240 |
| gattggaggg | cgatgatata | gccgttcagt | tcccattctc | tctctctttt | ttacaggatc | 300 |
| actcagtaag | gttcactata | aatgagaaag | agagaatgcc | aaccaacagc | agcggtttgt | 360 |
| tgatctcttc | acaacggttc | aatgagacct | ggaagtacgc | attcgacaag | aaatttcaag | 420 |
| aggaggcgaa | caggaccagt | attccacaat | tccacttcct | taagcaaaaa | caaactgtga | 480 |
| actcattctg | gtcgaaaata | tcttcatttt | tgtcactttc | aaactccact | gcagacacat | 540 |
| ttcatcttcg | aaacggtgat | gtatccgtag | aaatctttgc | tgaacctttt | caattgaaag | 600 |
| tttactggca | aaatgcgctg | aaacttattg | taaacgagca | aaatttcctg | aacattgaac | 660 |
| atcatagaac | taagcaggaa | aacttcgcac | acgtgctgcc | agaagaaaca | actttcaaca | 720 |
| tgtttaagga | caatttcttg | tattcaaagc | atgactctat | gcctttgggg | cctgaatcgg | 780 |
| ttgcgctaga | tttctctttc | atgggttcta | ctaatgtcta | cggtataccg | aacatgcga | 840 |
| cgtcgctaag | gctgatggac | acttcaggtg | gaaaggaacc | ctacaggctt | ttcaacgttg | 900 |
| atgtctttga | gtacaacatc | ggtaccagcc | aaccaatgta | cggttcgatc | ccattcatgt | 960 |
| tttcatcttc | gtccacatct | atctttttggg | tcaatgcagc | tgacacttgg | gtagacataa | 1020 |
| agtatgacac | cagtaaaaat | aaaacgatga | ctcattggat | ctccgaaaat | ggtgtcatag | 1080 |
| atgtagtcat | gtccctgggg | ccagatattc | caactatcat | tgacaaattt | accgatttga | 1140 |
| ctggtagacc | cttttttaccg | cccatttcct | ctatagggta | ccatcaatgt | agatggaatt | 1200 |
| ataatgatga | gatggacgtt | ctcacagtgg | actctcagat | ggatgctcat | atgattcctt | 1260 |
| acgattttat | ttggttggac | ttggagtata | cgaacgacaa | aaaatatttt | acttggaagc | 1320 |
| agcactcctt | tcccaatcca | aaaaggctgt | tatccaaatt | aaaaaagttg | ggtagaaatc | 1380 |
| ttgtcgtact | aatcgatcct | catttaaaga | aagattatga | aatcagtgac | agggtaatta | 1440 |
| atgaaaatgt | agcagtcaag | gatcacaatg | gaaatgacta | tgtaggtcat | gctggccag | 1500 |
| gtaattctat | atggattgat | accataagca | aatatggcca | aaagatttgg | aagtcctttt | 1560 |
| tcgaacggtt | tatggatctg | ccggctgatt | taactaattt | attcatttgg | aatgatatga | 1620 |
| acgagccttc | gattttcgat | ggcccagaga | ccacagctcc | aaaagatttg | attcacgaca | 1680 |
| attacattga | ggaaagatcc | gtccataaca | tatatggtct | atcagtgcat | gaagctactt | 1740 |
| acgacgcaat | aaaatcgatt | tattcaccat | ccgataagcg | tccttttccttt | ctaacaaggg | 1800 |
| ctttttttttgc | cggctctcaa | cgtactgctg | ccacatggac | tggtgacaat | gtggccaatt | 1860 |
| gggattactt | aaagatttcc | attcctatgg | ttctgtcaaa | caacattgct | ggtatgccat | 1920 |
| ttataggagc | cgacatagct | ggctttgctg | aggatcctac | acctgaattg | attgcacgtt | 1980 |
| ggtaccaagc | gggcttatgg | tacccattttt | ttagagcaca | cgcccatata | gacaccaaga | 2040 |
| gaagagaacc | atacttattc | aatgaacctt | tgaagtcgat | agtacgtgat | attatccaat | 2100 |
| tgagatattt | cctgctacct | acctatacaa | ccatgtttca | taaatcaagt | gtcactggat | 2160 |
| ttccgataat | gaatccaatg | tttattgaac | accctgaatt | tgctgaattg | tatcatatcg | 2220 |

```
ataaccaatt ttactggagt aattcaggtc tattagtcaa acctgtcacg gagcctggtc    2280
aatcagaaac ggaaatggtt ttcccacccg gtatattcta tgaattcgca tctttacact    2340
cttttataaa caatggtact gatttgatag aaaagaatat ttctgcacca ttggataaaa    2400
ttccattatt tattgaaggc ggtcacatta tcactatgaa agataagtat agaagatctt    2460
caatgttaat gaaaaacgat ccatatgtaa tagttatagc ccctgatacc gagggacgag    2520
ccgttggaga tctttatgtt gatgatggag aaacttttgg ctaccaaaga ggtgagtacg    2580
tagaaactca gttcattttc gaaacaata ccttaaaaaa tgttcgaagt catattcccg    2640
agaatttgac aggcattcac cacaatactt tgaggaatac caatattgaa aaatcatta    2700 tcgcaaagaa taatttacaa cacaacataa cgttgaaaga cagtattaaa gtcaaaaaaa    2760
atggcgaaga aagttcattg ccgactagat cgtcatatga gaatgataat aagatcacca    2820
ttcttaacct atcgcttgac ataactgaag attgggaagt tattttttggg cccgaacaaa    2880 aactcatctc agaagaggat ctgaatagcc ccgtcgacca cgacgaactg tgagttttag    2940
ccttagacat gactgttcct cagttcaagt tgggcactta cgagaagacc ggtcttgcta    3000
gattctaatc aagaggatgt cagaatgcca tttgcctgag agatgcaggc ttcattttg    3060 atacttttt atttgtaacc tatatagtat aggattttt ttgtcatttt gtttcttctc    3120
gtacgagctt gctcctgatc agcctatctc gcagctgatg aatatcttgt ggtaggggtt    3180
tgggaaaatc attcgagttt gatgttttc ttggtatttc ccactcctct tcagagtaca    3240
gaagattaag tgagaccttc gtttgtgcgg atcccccaca caccatagct tcaaaatgtt    3300
tctactcctt ttttactctt ccagatttt tcggactccg cgcatcgccg taccacttca    3360
aaacacccaa gcacagcata ctaaattttc cctctttctt cctctagggt gtcgttaatt    3420
acccgtacta aaggtttgga aaagaaaaaa gagaccgcct cgtttctttt tcttcgtcga    3480
aaaaggcaat aaaaattttt atcacgtttc tttttcttga aatttttttt tttagttttt    3540
ttctctttca gtgacctcca ttgatattta agttaataaa cggtcttcaa tttctcaagt    3600
ttcagtttca tttttcttgt tctattacaa cttttttac ttcttgttca ttagaaagaa    3660
agcatagcaa tctaatctaa gggcggtgtt gacaattaat catcggcata gtatatcggc    3720
atagtataat acgacaaggt gaggaactaa accatggcca agttgaccag tgccgttccg    3780
gtgctcaccg cgcgcgacgt cgccggagcg gtcgagttct ggaccgaccg gctcgggttc    3840
tcccgggact tcgtggagga cgacttcgcc ggtgtggtcc gggacgacgt gaccctgttc    3900
atcagcgcgg tccaggacca ggtggtgccg gacaacaccc tggcctgggt gtgggtcgcg    3960
ggcctggacg agctgtacgc cgagtggtcg gaggtcgtgt ccacgaactt ccgggacgcc    4020
tccgggccgg ccatgaccga gatcggcgag cagccgtggg ggcggagtt cgccctgcgc    4080 gacccggccg gcaactgcgt gcacttcgtg gccgaggagc aggactgaca cgtccgacgg    4140
cggcccacgg gtcccaggcc tcggagatcc gtcccccttt tcctttgtcg atatcatgta    4200
attagttatg tcacgcttac attcacgccc tcccccaca tccgctctaa ccgaaaagga    4260
aggagttaga caacctgaag tctaggtccc tatttatttt tttatagtta tgttagtatt    4320
aagaacgtta tttatatttc aaattttct ttttttctg tacagacgcg tgtacgcatg    4380
taacattata ctgaaaacct tgcttgagaa ggttttggga cgctcgaagg ctttaatttg    4440
caagctggag accaacatgt gagcaaaagg ccagcaaaag gccaggaacc gtaaaaaggc    4500
cgcgttgctg gcgttttcc ataggctccg ccccctgac gagcatcaca aaaatcgacg    4560
ctcaagtcag aggtggcgaa acccgacagg actataaaga taccaggcgt ttccccctgg    4620
```

```
aagctccctc gtgcgctctc ctgttccgac cctgccgctt accggatacc tgtccgcctt    4680
tctcccttcg ggaagcgtgg cgctttctca atgctcacgc tgtaggtatc tcagttcggt    4740
gtaggtcgtt cgctccaagc tgggctgtgt gcacgaaccc cccgttcagc ccgaccgctg    4800
cgccttatcc ggtaactatc gtcttgagtc caacccggta agacacgact tatcgccact    4860
ggcagcagcc actggtaaca ggattagcag agcgaggtat gtaggcggtg ctacagagtt    4920
cttgaagtgg tggcctaact acggctacac tagaaggaca gtatttggta tctgcgctct    4980
gctgaagcca gttaccttcg gaaaaagagt tggtagctct tgatccggca acaaaccac     5040 cgctggtagc ggtggttttt tgtttgcaa gcagcagatt acgcgcagaa aaaaggatc      5100 tcaagaagat cctttgatct tttctacggg gtctgacgct cagtggaacg aaaactcacg    5160
ttaagggatt ttggtcatgc atgagatcag atctttttg tagaaatgtc ttggtgtcct     5220
cgtccaatca ggtagccatc tctgaaatat ctggctccgt tgcaactccg aacgacctgc    5280
tggcaacgta aaattctccg ggtaaaact taaatgtgga gtaatggaac cagaaacgtc     5340
tcttcccttc tctctccttc caccgcccgt taccgtccct aggaaatttt actctgctgg    5400
agagcttctt ctacggcccc cttgcagcaa tgctcttccc agcattacgt tgcgggtaaa    5460
acggaggtcg tgtacccgac ctagcagccc agggatggaa aagtcccggc cgtcgctggc    5520
aataatagcg ggcggacgca tgtcatgaga ttattggaaa ccaccagaat cgaatataaa    5580
aggcgaacac ctttcccaat tttggtttct cctgacccaa agactttaaa tttaatttat    5640
ttgtccctat ttcaatcaat tgaacaacta tttcgaaacg aggaattcac gtggcccagc    5700
cggccgtctc ggatcggtac c                                              5721
```

<210> SEQ ID NO 25
<211> LENGTH: 7230
<212> TYPE: DNA
<213> ORGANISM: Artificial Sequence
<220> FEATURE:
<223> OTHER INFORMATION: Description of Artificial Sequence:Sequence of
      plasmid pGAPADE1glsIIHDEL.

<400> SEQUENCE: 25

```
cgtactcacc tctttggtag ccaaaagttt ctccatcatc aacataaaga tctccaacgg     60
ctcgtccctc ggtatcaggg gctataacta ttacatatgg atcgtttttc attaacattg    120
aagatcttct atacttatct ttcatagtga taatgtgacc gccttcaata aataatggaa    180
ttttatccaa tggtgcagaa atattctttt ctatcaaatc agtaccattg tttataaaag    240
agtgtaaaga tgcgaattca tagaatatac cgggtgggaa aaccatttcc gtttctgatt    300
gaccaggctc cgtgacaggt ttgactaata gacctgaatt actccagtaa aattggttat    360
cgatatgata caattcagca aattcagggt gttcaataaa cattggattc attatcggaa    420
atccagtgac acttgattta tgaaacatgg tgtataaggt aggtagcagg aaatatctca    480
attggataat atcacgtact atcgacttca aaggttcatt gaataagtat ggttctcttc    540
tcttggtgtc tatatgggcg tgtgctctaa aaaatgggta ccataagccc gcttggtacc    600
aacgtgcaat caattcaggt gtaggatcct cagcaaagcc agctatgtcg gctcctataa    660
atggcatacc agcaatgttg tttgacagaa ccataggaat ggaaatcttt aagtaatccc    720
aattggccac attgtcacca gtccatgtgg cagcagtacg ttgagagccg gcaaaaaaag    780
cccttgttag aaggaaagga cgcttatcgg atggtaata atcgattttt attgcgtcgt     840
aagtagcttc atgcactgat agaccatata tgttatggac ggatctttcc tcaatgtaat    900
```

-continued

```
tgtcgtgaat caaatctttt ggagctgtgg tctctgggcc atcgaaaatc gaaggctcgt      960
tcatatcatt ccaaatgaat aaattagtta atcagccgg cagatcccata aaccgttcga     1020
aaaaggactt ccaaatcttt tggccatatt tgcttatggt atcaatccat atagaattac     1080
ctggccagca atgacctaca tagtcatttc cattgtgatc cttgactgct acattttcat     1140
taattaccct gtcactgatt tcataatctt tcttaaatg aggatcgatt agtacgacaa      1200
gatttctacc caacttttt aatttggata acagccttt tggattggga aggagtgct       1260
gcttccaagt aaaatatttt ttgtcgttcg tatactccaa gtccaaccaa ataaaatcgt     1320
aaggaatcat atgagcatcc atctgagagt ccactgtgag aacgtccatc tcatcattat     1380
aattccatct acattgatgg taccctatag aggaaatggg cggtaaaaag ggtctaccag     1440
tcaaatcggt aaatttgtca atgatagttg aatatctgg ccccagggac atgactacat      1500
ctatgacacc attttcggag atccaatgag tcatcgtttt attttactg gtgtcatact      1560
ttatgtctac ccaagtgtca gctgcattga cccaaaagat agatgtggac gaagatgaaa     1620
acatgaatgg gatcgaaccg tacattggtt ggctggtacc gatgttgtac tcaaagacat     1680
caacgttgaa aagcctgtag ggttcctttc cacctgaagt gtccatcagc cttagcgacg     1740
tcgcatgttc cggtataccg tagacattag tagaacccat gaaagagaaa tctagcgcaa     1800
ccgattcagg ccccaaaggc atagagtcat gctttgaata caagaaattg tccttaaaca     1860
tgttgaaagt tgtttcttct ggcagcacgt gtgcgaagtt ttcctgctta gttctatgat     1920
gttcaatgtt caggaaattt tgctcgttta caataagttt cagcgcattt tgccagtaaa     1980
ctttcaattg aaaaggttca gcaaagattt ctacggatac atcaccgttt cgaagatgaa     2040
atgtgtctgc agtggagttt gaaagtgaca aaaatgaaga tattttcgac cagaatgagt     2100
tcacagtttg ttttttgctta aggaagtgga attgtggaat actggtcctg ttcgcctcct    2160
cttgaaattt cttgtcgaat gcgtacttcc aggtctcatt gaaccgttgt gaagagatca    2220
acaaaccgct gctgttggtt ggcattctct cttttctcatt tatagtgaac cttactgagt    2280
gatcctgtaa aaaagagaga gagaatggga actgaacggc tatatcatcg ccctccaatc    2340
ttggtatagt tttaattatg gtagcatgaa gcacattctc taaaggatcg tgtgcaatag    2400
actcggcgtc cactttgtaa tagcagtgat gagatttggc aatatttct gcataaaccc      2460
tgtttctatg gcaaaaccca gattgcgcac acttctttaa tagatagtcg gtaaacgcat    2520
gcgaaaaagc ggtaaagaag accaattggc atacgagcca tttcaaaagg accatctcga    2580
ggtaccgatc cgagacggcc ggctgggcca cgtgaattcc tcgtttcgaa atagttgttc    2640
aattgattga aataggggaca aataaattaa atttaaagtc tttgggtcag gagaaaccaa    2700
aattgggaaa ggtgttcgcc ttttatattc gattctggtg gtttccaata atctcatgac   2760
atgcgtccgc ccgctattat tgccagcgac ggccgggact tttccatccc tgggctgcta   2820
ggtcgggtac acgacctccg ttttacccgc aacgtaatgc tgggaagagc attgctgcaa   2880
gggggccgta gaagaagctc tccagcagag taaaatttcc tagggacggt aacgggcggt   2940
ggaaggagag agaagggaag agacgtttct ggttccatta ctccacattt aagttttacc   3000
ccggagaatt ttacgttgcc agcaggtcgt tcggagttgc aacggagcca gatatttcag   3060
agatggctac ctgattggac gaggacacca agacatttct acaaaaaaga tctgatctca   3120
tcgaccggct gcattaatga atcggccaac gcgcggggag aggcggtttg cgtattgggc   3180
gctcttccgc ttcctcgctc actgactcgc tgcgctcggt cgttcggctg cggcgagcgg   3240
```

```
tatcagctca ctcaaaggcg gtaatacggt tatccacaga atcagggat  aacgcaggaa   3300 agaacatgtg agcaaaaggc cagcaaaagg ccaggaaccg taaaaaggcc gcgttgctgg   3360
cgttttccca taggctccgc cccctgacg  agcatcacaa aaatcgacgc tcaagtcaga   3420
ggtggcgaaa cccgacagga ctataaagat accaggcgtt tccccctgga agctccctcg   3480
tgcgctctcc tgttccgacc ctgccgctta ccggatacct gtccgccttt ctcccttcgg   3540
gaagcgtggc gctttctcat agctcacgct gtaggtatct cagttcggtg taggtcgttc   3600
gctccaagct gggctgtgtg cacgaacccc ccgttcagcc cgaccgctgc gccttatccg   3660
gtaactatcg tcttgagtcc aacccggtaa gacacgactt atcgccactg gcagcagcca   3720
ctggtaacag gattagcaga gcgaggtatg taggcggtgc tacagagttc ttgaagtggt   3780
ggcctaacta cggctacact agaaggacag tatttggtat ctgcgctctg ctgaagccag   3840
ttaccttcgg aaaaagagtt ggtagctctt gatccggcaa acaaaccacc gctggtagcg   3900
gtggtttttt tgtttgcaag cagcagatta cgcgcagaaa aaaggatct  caagaagatc   3960 ctttgatctt ttctacgggg tctgacgctc agtggaacga aaactcacgt taagggattt   4020
tggtcatgag attatcaaaa aggatcttca cctagatcct tttaaattaa aaatgaagtt   4080
ttaaatcaat ctaaagtata tatgagtaaa cttggtctga cagttaccaa tgcttaatca   4140
gtgaggcacc tatctcagcg atctgtctat ttcgttcatc catagttgcc tgactccccg   4200
tcgtgtagat aactacgata cgggagggct taccatctgg ccccagtgct gcaatgatac   4260
cgcgagaccc acgctcaccg gctccagatt tatcagcaat aaaccagcca gccggaaggg   4320
ccgagcgcag aagtggtcct gcaactttat ccgcctccat ccagtctatt aattgttgcc   4380
gggaagctag agtaagtagt tcgccagtta atagtttgcg caacgttgtt gccattgcta   4440
caggcatcgt ggtgtcacgc tcgtcgtttg gtatggcttc attcagctcc ggttcccaac   4500
gatcaaggcg agttacatga tcccccatgt tgtgcaaaaa agcggttagc tccttcggtc   4560
ctccgatcgt tgtcagaagt aagttggccg cagtgttatc actcatggtt atggcagcac   4620
tgcataattc tcttactgtc atgccatccg taagatgctt ttctgtgact ggtgagtact   4680
caaccaagtc attctgagaa tagtgtatgc ggcgaccgag ttgctcttgc ccggcgtcaa   4740
tacgggataa taccgcgcca catagcagaa ctttaaaagt gctcatcatt ggaaaacgtt   4800
cttcggggcg aaaactctca aggatcttac cgctgttgag atccagttcg atgtaaccca   4860
ctcgtgcacc caactgatct tcagcatctt ttactttcac cagcgtttct gggtgagcaa   4920
aaacaggaag gcaaaatgcc gcaaaaaagg gaataagggc gacacggaaa tgttgaatac   4980
tcatactctt ccttttcaa  tagctccaag gcaacaaatt gactactcag accgacattc   5040
attcgttatt gattttaaat caacgataaa cggaatggtt acttgaatga tttcacttta   5100
tgatcattgt ttactaatta cctaaatagg attttatatg gaattggaag aataagggaa   5160
atttcagatg tctgaaaaag gcgaggaggg tactaatcat tcaagcccat tcttgccag    5220 taattgcttc ataagcttca atatactttt ctttactctt gatagcaatt tctgcatcca   5280
tggctacgcc ctctttgcca ttcaatccgt tggccgtcaa ccaatctctg agaaactgct   5340
tatcgtaact ctcttgcgat ttacccactt ggtaagtctt ttgattccaa aatctagaag   5400
aatctggagt taaaacttca tctactagta ccaattcatt gttttcgtcc agtccaaatt   5460
cgaatttcgt atcagcaata atgatcccct tcaaagggc  gaagtttttt gcagcagaat   5520
acaactcgac cgccttgaca gcgacttct  cacaaatgtc tttacctaca atctcagcag   5580
cttgttcaat agagatgttt tcatcgtgtt cacctgttc  agctttcgtt gaaggtgtga   5640
```

```
aaatcggagt tggaaaggcg tcgctctctt gaaggttctc gttttcaacc ttgactccat    5700
ggacagtttt tgagttcttg tactcttttcc atgcacttcc agtgatgtaa cctctgacaa    5760
tggcttccaa aggtatcagt ctgtgctttt ttactatcaa ggatcgtccc tctaattgag    5820
atttgtattt ttcttcagac agttttgatg gtagtaaagc aaagacttcc ttgtcattag    5880
aagcaaccaa atgattcttt atgtagggtg ccaaaaaatc aaaccagaaa actgagagct    5940
gagtcaaaat ctttccctta tcaggaatac cgtttgtcat aatcacatcg taagcggaga    6000
tacggtcagt tgcgacgaac agcaagttgt tctcatcgac tgcataaatg tctctaacct    6060
ttcctttggc gattaaaggt aggattccgt ccagatcagt gttcacaatg gacatacttg    6120
gaaggataca gcaaagtgtg ttggaagcga tgacacatgg aaaggaattt ttcgagtttc    6180
ctagagtagt atattggggc ggtgaaagtt cagatgttta atgcttaata ctcttatact    6240
cttcaaagcg cccaagtgtt tctgccaacc tgacttttt ctgaataatg aatcgttcaa    6300
gtggagtatt taaccatga ttaagttacg tgatttggca ctggataagg tcgaaaaata    6360
tccgtattca taaacgatta ttggtaaaag ttacaaaata ccactaatta cggagaagct    6420
tagtaacagt tatcatctct tggtcgatta acgcttacaa tttccattcg ccattcaggc    6480
tgcgcaactg ttgggaaggg cgatcggtgc gggcctcttc gctattacgc cagggcctcg    6540
aggcacaaac gaacgtctca cttaatcttc tgtactctga agaggagtgg gaaataccaa    6600 gaaaacatc aaactcgaat gattttccca acccctacc acaagatatt catcagctgc    6660
gagataggct gatcaggagc aagctcgtac gagaagaaac aaaatgacaa aaaaaatcct    6720
atactatata ggttacaaat aaaaaagtat caaaaatgaa gcctgcatct ctcaggcaaa    6780
tggcattctg acatcctctt gattagaatc tagcaagacc ggtcttctcg taagtgccca    6840
acttgaactg aggaacagtc atgtctaagg ctaaaactca cagttcgtcg tggtcgacgg    6900
cgctattcag atcctcttct gagatgagtt tttgttcggg cccaaaaata acttcccaat    6960
cttcagttat gtcaagcgat aggttaagaa tggtgatctt attatcattc tcatatgacg    7020
atctagtcgg caatgaactt tcttcgccat tttttttgac tttaatactg tctttcaacg    7080
ttatgttgtg ttgtaaatta ttctttgcga taatgatttt ttcaatattg gtattcctca    7140
aagtattgtg gtgaatgcct gtcaaattct cggaatatg acttcgaaca ttttttaagg    7200
tattgttttc gaaaatgaac tgagtttcta                                    7230
```

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 26
gacgagatct ttttttcaga ccatatgacc gg                                   32

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 27
gcggaattct ttctcagtt gatttgtttg t                                    31

```
<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence:primer

<400> SEQUENCE: 28
gcgggtcgac cacgacgaac tgtgagtttt agccttagac atgac          45

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 29
caggagcaaa gctcgtacga g                                    21
```